United States Patent
Loupis et al.

(10) Patent No.: US 10,881,736 B2
(45) Date of Patent: *Jan. 5, 2021

(54) BIOPHOTONIC COMPOSITIONS COMPRISING A CHROMOPHORE AND A GELLING AGENT FOR TREATING WOUNDS

(71) Applicant: KLOX Technologies Inc., Laval (CA)

(72) Inventors: Nikolaos Loupis, Athens (GR); Remigio Piergallini, A.P. (IT); Shipra Rastogi, Laval (CA)

(73) Assignee: KLOX TECHNOLOGIES INC., Laval (CA)

( * ) Notice: Subject to any disclaimer, the term of this patent is extended or adjusted under 35 U.S.C. 154(b) by 25 days.

This patent is subject to a terminal disclaimer.

(21) Appl. No.: 14/901,246

(22) PCT Filed: Jul. 2, 2014

(86) PCT No.: PCT/CA2014/000536
§ 371 (c)(1),
(2) Date: Dec. 28, 2015

(87) PCT Pub. No.: WO2015/000058
PCT Pub. Date: Jan. 8, 2015

(65) Prior Publication Data
US 2016/0193338 A1    Jul. 7, 2016

Related U.S. Application Data

(60) Provisional application No. 61/904,204, filed on Nov. 14, 2013, provisional application No. 61/842,433, filed on Jul. 3, 2013.

(51) Int. Cl.
| | | |
|---|---|---|
| *A61K 8/04* | (2006.01) | |
| *A61K 8/22* | (2006.01) | |
| *A61K 8/49* | (2006.01) | |
| *A61N 5/06* | (2006.01) | |
| *A61Q 19/00* | (2006.01) | |
| *A61K 41/00* | (2020.01) | |
| *C09K 11/06* | (2006.01) | |
| *A61L 26/00* | (2006.01) | |
| *A61K 8/81* | (2006.01) | |
| *A61Q 19/02* | (2006.01) | |
| *A61Q 19/08* | (2006.01) | |

(52) U.S. Cl.
CPC ...... *A61K 41/0057* (2013.01); *A61K 41/0038* (2013.01); *A61L 26/0066* (2013.01); *A61N 5/062* (2013.01); *C09K 11/06* (2013.01); *A61N 2005/0662* (2013.01); *C09K 2211/1011* (2013.01); *C09K 2211/1088* (2013.01)

(58) Field of Classification Search
CPC ............ A61K 41/0057; A61K 41/0038; A61N 5/062; A61N 2005/0662; A61L 26/0066; C09K 11/06; C09K 2211/1088; C09K 2211/1011

See application file for complete search history.

(56) References Cited

U.S. PATENT DOCUMENTS

| | | |
|---|---|---|
| 2,877,221 A | 3/1959 | Lanbach |
| 3,141,321 A | 7/1964 | Nicholas |
| 3,293,127 A | 12/1966 | Name |
| 3,309,274 A | 3/1967 | Brilliant |
| 3,372,125 A | 3/1968 | Hill |
| 3,595,798 A | 7/1971 | Smith et al. |
| 3,597,362 A | 8/1971 | Rauhut |
| 3,652,420 A | 3/1972 | Hill |
| 3,671,450 A | 6/1972 | Rauhut et al. |
| 3,728,446 A | 4/1973 | Roberts et al. |
| 4,320,140 A | 3/1982 | Crounse et al. |
| 4,402,959 A | 9/1983 | Dybas et al. |
| 4,430,381 A | 2/1984 | Harvey et al. |
| 4,533,435 A | 8/1985 | Intili |
| 4,574,097 A | 3/1986 | Honeycutt |
| 4,625,026 A | 11/1986 | Kim |
| 4,647,578 A | 3/1987 | Crounse et al. |
| 4,736,467 A | 4/1988 | Schwarze et al. |
| 4,855,139 A | 8/1989 | Srinivasan |
| 4,891,211 A | 1/1990 | Winston |
| 4,992,256 A | 2/1991 | Skaggs et al. |
| 5,069,907 A | 12/1991 | Mixon et al. |
| 5,091,102 A | 2/1992 | Sheridan |
| 5,292,362 A | 3/1994 | Bass et al. |

(Continued)

FOREIGN PATENT DOCUMENTS

| | | |
|---|---|---|
| CA | 2166527 | 7/1996 |
| CA | 2222027 A1 | 6/1998 |

(Continued)

OTHER PUBLICATIONS

PCT International Search Report Serial No. PCTCA2014000536, dated Oct. 16, 2014 (7 pages).
Gonzales et al., "Photodynamic inactivation of microorganisms as an innovative approach to kill mucocutaneous and skin microorganisms," Giornale Italiano Di Dermatologia e Venereologia, 145, pp. 477-489 (2010).
Lins, et al., "Enhancement of Antimicrobial Action of Photodynamic Therapy in the Presence of Hydrogen Peroxide," in Microbial Pathogens and Strategies for Combating Them: Science, Technology and Education, Edition: Microbiology Book Series #4, Editor: A. Mendez-Vilas, pp. 367-371 (2013) (acquired from: https://www.researchgate.net/publication/283644315_Enhancement_of_Antimicrobial_Action_of_Photodynamic_Therapy_in_the_Presence_of Hydrogen_Peroxide).

(Continued)

*Primary Examiner* — Boniface N Nganga
(74) *Attorney, Agent, or Firm* — BCF LLP

(57) ABSTRACT

The present disclosure provides biophotonic compositions, kits and their uses. In particular, the biophotonic compositions of the present disclosure are substantially resistant to leaching such that low amounts of chromophores present in the biophotonic composition leach out of the composition. The biophotonic compositions and their uses are useful for promoting repair of non-healing wounds.

21 Claims, 26 Drawing Sheets

(56) References Cited

U.S. PATENT DOCUMENTS

| | | | |
|---|---|---|---|
| 5,611,793 A | 3/1997 | Wilson et al. |
| 5,639,464 A | 6/1997 | Terry et al. |
| 5,658,148 A | 8/1997 | Neuberger et al. |
| 5,723,148 A | 3/1998 | Love |
| 5,749,968 A | 5/1998 | Melanson et al. |
| 5,785,527 A | 7/1998 | Jensen et al. |
| 5,844,016 A | 12/1998 | Sawhney et al. |
| 5,853,883 A | 12/1998 | Nohr et al. |
| 5,854,147 A | 12/1998 | Nohr et al. |
| 5,858,332 A | 1/1999 | Jensen et al. |
| 5,885,557 A | 3/1999 | Lentini |
| 5,894,042 A | 4/1999 | Ferralli |
| 5,919,554 A | 7/1999 | Watterson et al. |
| 5,922,331 A | 7/1999 | Mausner |
| 6,107,466 A | 8/2000 | Hasan et al. |
| 6,121,341 A | 9/2000 | Sawhney et al. |
| 6,149,895 A | 11/2000 | Kutsch |
| 6,444,725 B1 | 9/2002 | Trom et al. |
| 6,485,709 B2 | 11/2002 | Banerjee et al. |
| 6,541,460 B2 | 4/2003 | Petito |
| 6,905,672 B2 | 6/2005 | Rajaiah et al. |
| 7,066,941 B2 | 6/2006 | Perricone |
| 7,081,128 B2 | 7/2006 | Hart et al. |
| 7,083,610 B1 | 8/2006 | Murray et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,182,473 B2 | 5/2012 | Altshuler et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 | 3/2015 | Piergallini et al. |
| 8,986,719 B2 | 3/2015 | Piergallini et al. |
| 8,986,745 B2 | 3/2015 | Piergallini et al. |
| 8,986,746 B2 | 3/2015 | Piergallini et al. |
| 9,345,648 B2 | 5/2016 | Piergallini et al. |
| 9,375,466 B2 | 6/2016 | Piergallini et al. |
| 10,376,455 B2 * | 8/2019 | Piergallini | A61Q 19/00 |
| 2001/0022970 A1 | 9/2001 | Dees et al. |
| 2002/0029071 A1 | 3/2002 | Whitehurst |
| 2003/0004499 A1 | 1/2003 | McDaniel |
| 2003/0198605 A1 | 10/2003 | Montgomery |
| 2004/0009227 A1 | 1/2004 | Yao |
| 2004/0010299 A1 | 1/2004 | Tolkoff et al. |
| 2004/0136971 A1 | 7/2004 | Scharp et al. |
| 2004/0147984 A1 | 7/2004 | Altshuler et al. |
| 2004/0191330 A1 | 9/2004 | Keefe et al. |
| 2004/0193234 A1 | 9/2004 | Butler |
| 2004/0262569 A1 | 12/2004 | Cho et al. |
| 2005/0026298 A1 | 2/2005 | Bickett et al. |
| 2005/0042712 A1 | 2/2005 | Huth et al. |
| 2005/0059731 A1 | 3/2005 | Albrecht et al. |
| 2005/0098766 A1 | 5/2005 | Watson et al. |
| 2005/0118156 A1 * | 6/2005 | Woolverton | A61K 38/363 |
| | | | 424/94.6 |
| 2005/0123588 A1 | 6/2005 | Zhu et al. |
| 2005/0261750 A1 * | 11/2005 | McDaniel | A61B 18/203 |
| | | | 607/86 |
| 2006/0199242 A1 | 9/2006 | Cheung et al. |
| 2006/0217690 A1 | 9/2006 | Bastin et al. |
| 2006/0228320 A1 | 10/2006 | Minami et al. |
| 2006/0251687 A1 | 11/2006 | Lapidot et al. |
| 2007/0021807 A1 * | 1/2007 | Kurtz | A61N 5/0616 |
| | | | 607/88 |
| 2007/0092469 A1 | 4/2007 | Jacobs |
| 2007/0128132 A1 | 6/2007 | Piergallini et al. |
| 2007/0142762 A1 | 6/2007 | Kaplan et al. |
| 2007/0166369 A1 | 7/2007 | Neuberger et al. |
| 2007/0191249 A1 | 8/2007 | Lant |
| 2007/0244195 A1 | 10/2007 | Burkhart et al. |
| 2007/0286824 A1 | 12/2007 | Rabe et al. |
| 2008/0058689 A1 | 3/2008 | Holloway et al. |
| 2008/0091250 A1 | 4/2008 | Powell |
| 2008/0096857 A1 | 4/2008 | Curaudeau et al. |
| 2008/0108681 A1 | 5/2008 | Scimeca et al. |
| 2008/0113037 A1 | 5/2008 | Green et al. |
| 2008/0118578 A1 | 5/2008 | Dees |
| 2008/0138289 A1 | 6/2008 | Goronkin et al. |
| 2008/0206159 A1 | 8/2008 | Tamarkin |
| 2008/0255498 A1 | 10/2008 | Houle |
| 2008/0305101 A1 | 12/2008 | Ruoslahti et al. |
| 2009/0088824 A1 | 4/2009 | Baird et al. |
| 2009/0130030 A1 | 5/2009 | Ribi |
| 2009/0131499 A1 | 5/2009 | Castro et al. |
| 2009/0226506 A1 | 9/2009 | Masters et al. |
| 2009/0286886 A1 | 11/2009 | Fisher et al. |
| 2010/0227799 A1 | 9/2010 | Trudel |
| 2010/0255045 A1 | 10/2010 | Eymard Du Vernet |
| 2010/0266989 A1 | 10/2010 | Piergallini et al. |
| 2010/0277105 A1 | 11/2010 | Oyama |
| 2011/0008153 A1 | 1/2011 | Kato et al. |
| 2011/0171310 A1 | 7/2011 | Gousse et al. |
| 2011/0319808 A1 | 12/2011 | Bowler et al. |
| 2012/0171641 A1 | 7/2012 | Piergallini et al. |
| 2013/0122467 A1 | 5/2013 | Piergallini et al. |
| 2013/0281913 A1 | 10/2013 | Piergallini et al. |
| 2014/0105832 A1 | 4/2014 | Loupis et al. |
| 2014/0276354 A1 | 9/2014 | Piergallini et al. |
| 2014/0303547 A1 | 10/2014 | Loupis et al. |
| 2015/0065453 A1 | 3/2015 | Piergallini et al. |
| 2015/0119788 A1 | 4/2015 | Louipis et al. |
| 2015/0246127 A1 | 9/2015 | Louipis |
| 2015/0290103 A1 | 10/2015 | Piergallini et al. |
| 2015/0290320 A1 | 10/2015 | Piergallini et al. |
| 2015/0306131 A1 | 10/2015 | Piergallini et al. |
| 2015/0360047 A1 | 12/2015 | Loupis et al. |
| 2016/0136075 A1 | 5/2016 | Loupis et al. |

FOREIGN PATENT DOCUMENTS

| | | |
|---|---|---|
| CA | 2360202 A1 | 7/2000 |
| CA | 2457590 A1 | 3/2003 |
| CA | 2551613 | 12/2005 |
| CA | 2580381 A1 | 1/2006 |
| CA | 2706808 A1 | 8/2009 |
| CA | 2742942 A1 | 5/2010 |
| CA | 2742943 A1 | 5/2010 |
| CA | 2745059 | 6/2010 |
| CA | 2809405 | 1/2012 |
| CA | 2868893 A1 | 10/2013 |
| CA | 2883717 A1 | 3/2014 |
| CN | 1423549 A | 6/2003 |
| CN | 102133208 A | 7/2011 |
| CN | 102256591 A | 11/2011 |
| CN | 102300587 A | 12/2011 |
| CN | 102711831 A | 10/2012 |
| DE | 2935450 A1 | 3/1981 |
| DE | 3834130 A1 | 4/1990 |
| EP | 0380157 A1 | 8/1990 |
| EP | 0704539 A2 | 4/1996 |
| EP | 1235543 A1 | 9/2002 |
| EP | 1235544 A1 | 9/2002 |
| EP | 1749532 | 2/2007 |
| EP | 1779891 A1 | 5/2007 |
| EP | 1951184 | 8/2008 |
| EP | 2338465 | 6/2011 |
| JP | 01-279838 | 11/1989 |
| JP | H03169805 A | 7/1991 |
| JP | 04-219756 | 8/1992 |
| JP | H092925 A | 1/1997 |
| JP | H10182390 A | 7/1998 |
| JP | H10330235 | 12/1998 |
| JP | 2001-511137 A | 8/2001 |
| JP | 2002-502864 | 1/2002 |
| JP | 2002-226349 A | 8/2002 |
| JP | 2002233612 A | 8/2002 |
| JP | 2002-293747 A | 10/2002 |
| JP | 2003-231347 A | 8/2003 |
| JP | 2003-339875 A | 12/2003 |
| JP | 2005520606 A | 7/2005 |
| JP | 2008-231010 A | 10/2008 |
| JP | 200913132 A | 1/2009 |

(56) References Cited

FOREIGN PATENT DOCUMENTS

| | | |
|---|---|---|
| JP | 2012-508190 A | 4/2012 |
| JP | 2015-514724 A | 5/2015 |
| KR | 102007001729 | 2/2007 |
| MX | 2014012631 A | 1/2015 |
| RU | 2005134239 A | 5/2006 |
| WO | WO-1981000513 A1 | 3/1981 |
| WO | WO-1990009779 A1 | 9/1990 |
| WO | WO-1991002530 A1 | 3/1991 |
| WO | WO1993021992 | 11/1993 |
| WO | WO-1998010738 A1 | 3/1998 |
| WO | WO-1998011827 A1 | 3/1998 |
| WO | WO-1998030169 A1 | 7/1998 |
| WO | WO-1999039238 A1 | 8/1999 |
| WO | WO-1999049823 | 10/1999 |
| WO | WO-1999063900 A1 | 12/1999 |
| WO | WO-2000040266 | 7/2000 |
| WO | WO-2001000190 | 1/2001 |
| WO | WO-2001012181 | 2/2001 |
| WO | WO 0135906 A2 * | 5/2001 ........... A61K 8/0208 |
| WO | 2002011539 A1 | 2/2002 |
| WO | WO2002015539 | 2/2002 |
| WO | WO-2003000215 | 1/2003 |
| WO | WO-2003017824 | 3/2003 |
| WO | WO-2003061696 A2 | 7/2003 |
| WO | WO-2003086215 | 10/2003 |
| WO | WO-2003099247 | 12/2003 |
| WO | WO-2004028498 | 4/2004 |
| WO | WO2004081222 | 9/2004 |
| WO | WO-2005009604 A1 | 2/2005 |
| WO | WO-2005051305 A2 | 6/2005 |
| WO | WO-2006014597 A1 | 2/2006 |
| WO | WO-2006032847 A1 | 3/2006 |
| WO | 2006/048634 A1 | 5/2006 |
| WO | WO-2006047868 A1 | 5/2006 |
| WO | WO-2006072243 A1 | 7/2006 |
| WO | WO-2006118835 A2 | 11/2006 |
| WO | WO-2006125650 A1 | 11/2006 |
| WO | WO-2006135344 A1 | 12/2006 |
| WO | WO-2007087259 | 2/2007 |
| WO | WO-2007025244 A2 | 3/2007 |
| WO | WO-2007080453 A2 | 7/2007 |
| WO | WO-2007127172 | 11/2007 |
| WO | WO-2008011707 A1 | 1/2008 |
| WO | WO-2008013962 A2 | 1/2008 |
| WO | WO-2008052081 A2 | 5/2008 |
| WO | WO-2008139601 A1 | 11/2008 |
| WO | WO-2009089346 A2 | 7/2009 |
| WO | WO-2010051636 | 5/2010 |
| WO | WO2010051636 | 5/2010 |
| WO | WO2010051641 | 5/2010 |
| WO | WO-2010070292 A1 | 6/2010 |
| WO | WO2011006263 | 1/2011 |
| WO | WO-2011058448 A2 | 5/2011 |
| WO | WO-2011134087 A1 | 11/2011 |
| WO | WO-2012011875 A1 | 1/2012 |
| WO | WO-2012072980 | 6/2012 |
| WO | WO-2012110178 A1 | 8/2012 |
| WO | WO-2012119131 A1 | 9/2012 |
| WO | WO2013155620 | 10/2013 |
| WO | WO-2014040176 A1 | 3/2014 |
| WO | WO-2014138930 | 9/2014 |
| WO | WO-2016065488 A1 | 5/2016 |
| WO | WO-2017201615 A1 | 11/2017 |

OTHER PUBLICATIONS

Mintel, "Active Plus Deep Cleaning Tablets," Database GNPD [Online], May 2007, XP002769877, Database accession No. 707777 *Ingredients*.

Mintel, "Effervescent Tablets," Database GNPD [Online], May 2009, XP002769876, Database accession No. 1089966 *Ingredients*.

Alster, et al., "Photodynamic therapy: practical cosmetic applications," Journal of Drugs in Dermatology, 5(8):764-768 (2006).

Antunes, et al., "Evaluation of the clastogenicity and anticlastongenicity of the carotenoid bixin in human lymphocyte cultures," Mutation Research, 585(1-2):113-9 (2005).

Ariizumi et al., "Clinical evaluation of a Topical Applicant TSG-88 for periodontal disease," Dental Drug Therapy, 10(2):157-168 (1991) (English Abstract included).

Berneburg, et al., "Phototherapy with narrowband UVB," Acta Dermato-Venereologica, 85:1-11 (2005).

Chen et al., "Study of the chemiluminescent characteristics of some xanthone dyes," Analytica Chimica Acta, 292(1-2):159-167 (1994).

Clark, et al, "Eosin-Phloxine alcoholic solution", Mitt. Zool. Stat. Neapel, Jan. 1, 1981 (Jan. 1, 1981), pp. 170-186, XP055224968, Retrieved from the Internet: URL:http://tunic.ro/fise/tehnice/05-10020L.pdf* abstract * (1 page).

Colman, et al., "The healing of wounds in the skin of piglets treated with benzoyl peroxide," The Journal of Dermatologic Surgery and Oncology, 4(9):705-707 (1978).

Darzynkiewicz, et al., "Photosensitizing effects of the tricyclic heteroaromatic cationic dyes Pyronin Y and Toluidine Blue O (tolonium chloride)," Cancer Research, 48(5):1295-1299 (1988).

De, et al., "Environmental effects on the aggregation of some xanthene dyes used in lasers," Spectrochimica Acta Part A: Molecular and Biomolecular Spectroscopy, 61(8):1821-1833 (2005).

Decraene et al., "Cellulose acetate containing Toluidine Blue and Rose Bengal is an effective antimicrobial coating when exposed to white light," Applied and Env. Microbiology, 72:6(4436-4439) (Jun. 2006).

European Supplementary Search Report, Application No. EP09824320, dated Mar. 28, 2012 (12 pages).

FDA, Color Additive Status List, http://www.cfsanJda.gov/-dms/opa-appc.html, downloaded Jun. 18, 2008 (13 pages).

FDA, Product Classification Database Search, http://www.accessdata.fda.gov/scripts/cdrh/cfdocs/cfpcd/classificiation/c.f?ID-3964, Device: Eosin y: database, downloaded Jun. 18, 2008 (2 pages).

Fisher Scientific, "Material Safety Data Sheet: Sodium acetate buffer," https://fscimagef.fishersci.com/msds/91502.htm (ACC # 91502) (Apr. 13, 2000) (5 pages).

Goldberg, "Photodynamic therapy in skin rejuvenation," Clinics in Dermatology, 26(6):608-613 (2008).

Jankowski, et al., "The action of photosensitizers and serum in a bactericidal process. II. The effects of dyes: Hypericin, Eosin Y and Saphranine O," Polish Journal of Microbiology, 54(4):323-330 (2005).

Kelly, et al., "Combined photodynamic and photothermal induced injury enhances damage to in vivo model blood vessels," Lasers in Surgery and Medicine, 34(5):407-413 (2004).

Korb, et al, "An evaluation of the efficacy of Fluorescein, Rose Bengal, Lissamine Green, and a new dye mixture for ocular surface staining," Eye Contact Lens, Jan. 2008;34(1) 61-64. Jan. 1, 2008 (Jan. 1, 2008), XP055224976, Retrieved from the Internet: URL:http://www.ncbi.nlm.nih.gov/pubmed/181 80687 [retrieved on Nov. 2, 2015] * abstract * (1 page).

McCullach, et al., "Photosensitized destruction of Chlorella vulgaris by Methylene Blue or Nuclear Fast Red combined with hydrogen peroxide under visible light irradiation," Environmental Science and Technology, 40(7):2421-2425 (2006).

Meisel, et al., "Photodynamic therapy for periodontal diseases: state of the art," Journal of Photochemistry and Photobiology B: Biology, 79:159-170 (2005).

Mintel, "Gel Blush," http://gnpd.com; Jun. 2009 (4 pages).

Mintel, "Gold Bear Gums," http://gnpd.com, Feb. 2008 (3 pages).

Mintel, "Teens Braces Cleaner," http://gnpd.com, Jan. 2004 (2 pages).

Mintel, "Velvet Gloss Lip Pencil," http://gnpd.com; Feb. 2011 (4 pages).

Montenegro, et al., "Model studies on the photosensitized isomerization of bixin," Journal of Agriculture and Food Chemistry, 52(2): 367-73 (2004).

Nolan et al., "The efficacy of topical hyaluronic acid in the management of oral lichen planus," Journal of Oral Pathology and Medicine, 38(3):299-303 (2006).

(56) References Cited

OTHER PUBLICATIONS

Olympus America Inc., "Special characteristics of common biological stains," http://micro.magnet.fsu.edu/primer/photomicrography/bwstainchart.html, Apr. 30, 2000 (3 pages).
PCT International Preliminary Report on Patentability and Written Opinion for International Serial No. PCT/CA2013/000787, dated Nov. 27, 2013 (9 pages).
PCT International Search Report for International Application No. PCT/CA2010/001134 dated Oct. 8, 2010 (3 pages).
PCT International Search Report for International Application No. PCT/CA2013/000786, dated Jan. 8, 2014 (16 pages).
PCT International Search Report and Written Opinion for International Application No. PCT/CA2014/000161, dated May 30, 2014 (12 pages).
PCT International Search Report and Written Opinion for International Application No. PCT/CA2015/000407, dated Sep. 23, 2015 (13 pages).
PCT International Search Report Corrected for International Application No. PCT/CA2014/000261, dated Jul. 23, 2014 (7 pages).
PCT International Search Report for International Application No. PCT/CA2009/001615, dated Feb. 9, 2010 (9 pages).
PCT International Search Report for International Application No. PCT/CA2013/000395, dated Jul. 15, 2013 (12 pages).
Publication date of following document established by Internet Archive Wayback Machine (3 pages) <URL: <http://web.archive.org/web/20090208211504/http://en.wikipedia.org/wiki/Eosin Aug. 2, 2009.
Resources: Fluorochrome absorption emission wavelengths [Online] XP002449595 Retrieved from the Internet: URL: http://www.sciencegateway.org/resource s/fae1.htm>[retrieved on Sep. 6, 2007] see p. 2: Rhodamine WT emission nm 555 p. 2 (12 pages).
Roy, et al., "Dermal wound healing is subject to redox control," Molecular Therapy, 13(1):211-220 (2006).
Sezer, et al., "Topical drug delivery using chitosan nano- and microparticles," Expert Opinion in Drug Delivery, Informa UK, 9(9):1129-1146 (2012).

Steinberg, et al., "Genetic and physiological effects of noncoherent visible light combined with hydrogen peroxide on *Streptococcus mutans* in biofilm," Antimicrobial Agents and Chemotherapy, 52(7):2626-2631 (2008).
Subba, et al, "Photocatalytic transformation of dyes and by-products in the presence of hydrogen peroxide," Environmental Technology, 24(8):1025-1030 (2003).
Thompson, et al., "Fluorescence polarization standards for high-throughput screening and imaging," Bio Techniques, vol. 32 (5 pages) (2002).
Jarmolinskaja, et al., "Matrix metalloproteinases and inhibitors: classification, mechanism of action," Journal of Obstetrics and Gynecological Diseases, vol. LXI, pp. 113-125, 2012. [title translated from Russian].
Mintel, "Photodynamic therapy SPF 30" XP002775115. Database accession No. 1442681, pp. 1-5 (Nov. 30, 2010).
English Machine Translation of JP 2005520606A retrieved from https://worldwide.espacenet.com/ on Jul. 5, 2018.
English abstract for RU 2005134239 A provided.
English abstract for CN 1423549 A provided.
English abstract for CN 102256591 A provided.
English abstract for CN 102300587 A provided.
English abstract for CN 102711831 A provided.
English abstract for JP 2012-508190 A provided.
English abstract for JP 2015-506054 A provided.
English abstract for MX 2014012631 A provided.
Brock, et al., "Use of In Vitro and In Vivo Data in the Design, Development, and Quality Control of Sustained-Release Decongestant Dosage Forms", Pharmacotherapy, vol. 14, No. 4, 1994.
Durrani et al., "Studies on Drugs Release Kinetics From Carbopol® 934P Tablets", Pharmaceutical Res. Supp. 8: S-135, 1991—abstract only.
Samson et al. "Wound-Healing Technologies: Low-Level Laser and Vacuum-Assited Closure", Evidence Report/Technology Assessment 2004, 111, pp. 1-97—abstract only https://www.ncbi.nlm.nih.gov/books/NBK37464/toc/?report=reader.
English abstract provided for JP 2003-231347 A.
English abstract provided for JP 2008-231010 A.
Yao Jing, "Application Directory of Pharmaceutical Excipients", China Medical Science Press, Aug. 31, 2011, pp. 116-117.

\* cited by examiner

Time Zero

Time 7 Months

Time Zero

Time 4 Months

Time Zero

Time 10.5 Weeks

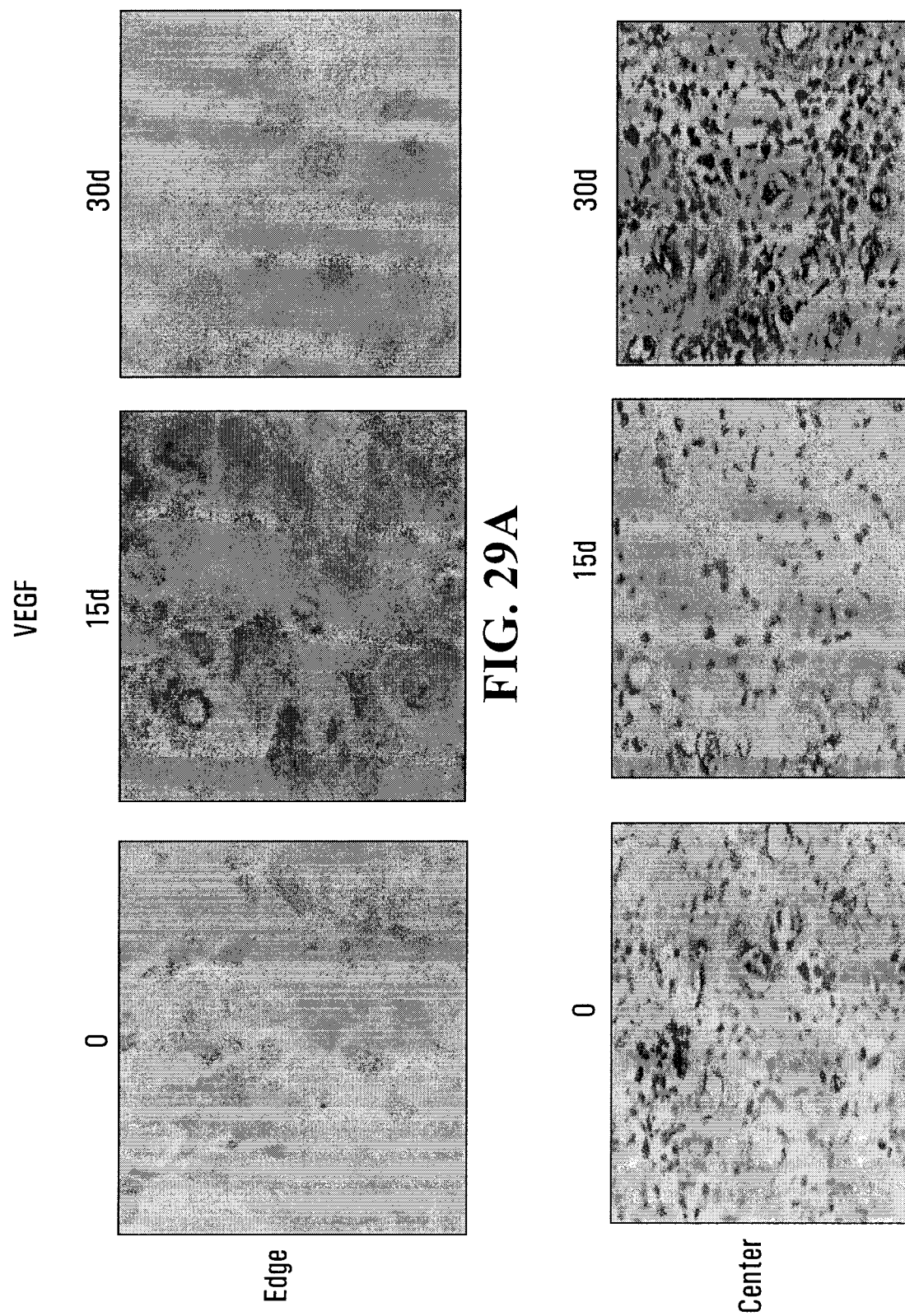

BIOPHOTONIC COMPOSITIONS COMPRISING A CHROMOPHORE AND A GELLING AGENT FOR TREATING WOUNDS

CROSS REFERENCE TO RELATED APPLICATIONS

This application is a United States National Stage Application under 35 U.S.C. § 371 of International Application No. PCT/CA2014/000536, filed Jul. 2, 2014, which claims the benefit of and priority to U.S. provisional patent application No. 61/842,433, filed Jul. 3, 2013, and to U.S. provisional patent application No. 61/904,204, filed Nov. 14, 2013. The content of each of the aforementioned patent applications is hereby incorporated by reference in its entirety. International Application No. PCT/CA2014/000536 was published under PCT Article 21(2) in English.

FIELD OF TECHNOLOGY

The present disclosure relates to biophotonic compositions, use of such biophotonic compositions, and biophotonic methods in the treatment of non-healing wounds, specifically but not exclusively in the treatment of wounds which have incomplete healing, delayed-healing, impaired healing or are non-responsive to healing treatments.

BACKGROUND INFORMATION

Normally healing wounds typically progress through four (4) overlapping phases: 1) hemostasis, 2) inflammation, 3) proliferation and 4) remodeling. However, some wounds do not follow this progression and remain stuck in the inflammatory or proliferation phases resulting in non-healing wounds (including incomplete healing, impaired healing, delayed-healing, non-responsive and chronic wounds). Chronic wounds are defined as wounds which fail to show any significant healing over a 3-month period, despite optimum wound care. The most commonly observed chronic wounds are diabetic ulcers, venous ulcers and pressure ulcers.

Current methods for treating non-healing wounds include debridement of necrotic tissue, compression including application of negative pressure, various wound dressings, and topical application of growth factors. In some cases, these methods can cause a non-healing wound to become 'unstuck' and continue to heal. However, in many cases, these methods do not have an effect on the wound.

If left untreated, difficult-to-heal or non-healing wounds can develop serious complications such as osteomyelitis, systemic amyloidosis and colonization by drug-resistant pathogens leading to antibiotic resistance. Therefore, there is a need for improved compositions and methods for treatment of non-healing wounds.

SUMMARY OF INVENTION

In one aspect, the present disclosure provides biophotonic compositions useful in the treatment of non-healing wounds, including chronic wounds.

In another aspect, the present disclosure provides biophotonic methods useful in the treatment of non-healing wounds, including chronic wounds.

In another aspect, there is provided a composition for treating non-healing wounds, comprising a first chromophore and a gelling agent present in an amount sufficient to gel the composition and render the biophotonic composition substantially resistant to leaching such that less than 15% by weight of the total chromophore amount leaches out of the biophotonic composition in use.

In another aspect, there is provided a biophotonic composition for treating non-healing wounds comprising a first chromophore; and a gelling agent present in an amount sufficient to gel the composition and render the biophotonic composition substantially resistant to leaching such that less than 15% by weight of the total chromophore amount leaches out of the biophotonic composition in use, as measured by (i) placing a 2 mm thick layer of the biophotonic composition onto a top surface of a 2.4-3 cm diameter polycarbonate (PC) membrane with a thickness of 10 microns and a pore size of 3 microns, (ii) contacting a bottom surface of the PC membrane with a phosphate saline buffer solution contained in a receptor compartment, and (iii) after a treatment time at room temperature and pressure, measuring the chromophore content in the receptor compartment.

In another aspect, there is provided a biophotonic composition for treating non-healing wounds comprising at least a first chromophore and a gelling agent, wherein the biophotonic composition is a gel or a semi-solid and is substantially resistant to leaching such that less than 15% of the total chromophore amount leaches out of the biophotonic composition into tissue when in contact with tissue in use. In certain embodiments, the biophotonic composition is spreadable so that it can conform to a tissue's topography.

In yet another aspect, there is provided a biophotonic composition for treating non-healing wounds comprising at least a first chromophore and a gelling agent, wherein the biophotonic composition is substantially translucent and is substantially resistant to leaching such that less than 15% of the total chromophore amount leaches out of the biophotonic composition into tissue when in contact with tissue in use. By substantially translucent is meant having a transmission of more than about 20%.

In a further aspect, there is provided a biophotonic composition for treating non-healing wounds comprising at least a first chromophore and a gelling agent, wherein the biophotonic composition and/or the gelling agent has a viscosity of between about 10,000-100,000, between about 10,000-90,000, between about 10,000-80,000, between about 10,000-70,000, between about 15,000-80,000, between about 15,000-70,000, between about 15,000-50,000, or between about 15,000-45,000 cP when measured using a Wells-Brookfield HB cone/plate viscometer and a CP-51 cone at room temperature at a rotational speed of 2 rpm and a torque >10%, or a Brookfield DV-II+Pro viscometer with a spindle of 7, at 50 rpm, 1 minute.

In a yet further aspect, there is provided a biophotonic composition for treating non-healing wounds, comprising a first chromophore in a carrier medium, wherein the composition is encapsulated in a membrane which membrane limits leaching of the first chromophore such that less than 15% by weight of the total chromophore amount leaches out of the biophotonic composition in use. In certain embodiments, the membrane is substantially translucent. The membrane comprises materials selected from a lipid, a polymer, gelatin, cellulose, and cyclodextrins. The polymer may be a polyethylene such as low density polyethylene, or polyvinyl chloride. The composition can also comprise a dendrimer, such as including poly(propylene amine). The carrier medium can be a liquid. It can also be a gel or semi-solid. In another aspect, there is provided a biophotonic composition for treating non-healing wounds comprising a first chromophore and a gelling agent, wherein the viscosity of the biophotonic composition is about 10,000 to about 100,000 cP, preferably about 10,000 to about 60,000 cP, more preferably about 10,000 to about 50,000 cP. In certain embodiments, the first chromophore is a fluorophore which absorbs and emits light from within the composition. Preferably, the biophotonic composition has a spreadable consistency.

In a yet further aspect, there is provided a biophotonic composition for treating non-healing wounds comprising a first chromophore and a second chromophore in a medium, wherein at least one of the first and second chromophores is a fluorophore. In some instances, the chromophore is Fluorescein and the second chromophore is Eosin Y. In some other instances, the first chromophore is Eosin Y and the second chromophore is one or more of Rose Bengal, Phloxine B and Erythrosine B.

In another aspect, there is provided a biophotonic composition for treating non-healing wounds comprising first and second chromophores in a medium, wherein the first chromophore is a fluorophore, and wherein light emitted by the first chromophore after photoactivation can photoactivate the second chromophore. In some implementations of the above aspects, the medium is a gel or is gel-like. The medium can have a spreadable consistency.

As used herein, the expression "gel-like" refers to a medium having properties ranging from soft and weak, to hard and tough.

As used herein, the expression "semi-solid" refers to a composition that lies along the boundary between a solid and a liquid. While similar to a solid in some respects, a composition that is semi-solid refers to a composition that can support its own weight and maintain its shape. In addition, a composition that is semi-solid is capable of conforming in shape to something applying pressure to it and the ability to flow under pressure. The terms "quasisolid", "semi-solid", and "semi-liquid" are herein used interchangeably.

By 'in use' is meant during a treatment time which can be up to about 5 minutes, up to about 6 minutes, up to about 7 minutes, up to about 8 minutes, up to about 9 minutes, up to about 10 minutes, up to about 15 minutes, up to about 20 minutes, up to about 25 minutes, or up to about 30 minutes. The treatment time may comprise the total length of time that the composition is in contact with tissues.

As used herein, "substantially resistant to leaching" can be understood to mean less than 15% of the total chromophore amount leaching out of the biophotonic composition into a phosphate saline buffer solution contained in a receptor compartment, through a 2.4-3 cm diameter polycarbonate (PC) membrane with a thickness of 10 microns and a pore size of 3 microns, having a top side onto which a 2 mm thick layer of the biophotonic composition is placed for 5 minutes at room temperature and pressure, and a bottom side which is in direct contact with the phosphate saline buffer solution. It will be understood that if the treatment time is longer than 5 minutes, the leaching test needs to be extended to the treatment time.

In certain embodiments of any of the foregoing or following, the biophotonic topical composition allows less than 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.8%, 0.5% or 0.1%, or substantially none of said chromophore content to leach out of the biophotonic composition.

In certain embodiments of any of the foregoing or following, the biophotonic composition is a topical composition. Preferably, the composition is a gel, semi-solid or viscous liquid, which can be spread on to the treatment site. In some embodiments, the composition can remain on the treatment site when the treatment site is inverted or tilted during the treatment time. As used herein, the expression "treatment site" refers to the portion or area of a tissue in need of a treatment as defined herein. In some instances, the treatment site is limited to the wound (such as the non-healing wound). In some other instance, the treatment site includes the wound (such as the non-healing wound) as well as a portion of the tissue that surrounds the wound.

In certain embodiments of any of the foregoing or following, the biophotonic composition is substantially translucent or transparent or both. By "substantially translucent", as used herein, it is meant that there is a transmission of light of more than about 20% through a 2 mm thick amount of the biophotonic composition. In some embodiments, the translucency comprises at least about 20%, at least about 21%, at least about 22%, at least about 23%, at least about 24%, at least about 25%, at least about 26%, at least abut 27%, at least about 28%, at least about 29%, at least about 30%, at least about 35%, at least about 40%, at least about 45%, at least about 50%, at least about 55%, at least about 60%, at least about 65%, at least about 70%, at least about 75%, at least about 85%, at least about 90%, at least about 95% or about 100% transmittance of light through a 2 mm thick amount of the biophotonic composition.

In certain embodiments of any of the foregoing or following, the composition and/or the gelling agent has a viscosity of between about 10,000-100,000, between about 10,000-90,000, between about 10,000-80,000, between about 10,000-70,000, between about 15,000-80,000, between about 15,000-70,000, between about 10,000-50,000, between about 10,000-40,000, between about 15,000-50,000 or between about 15,000-40,000 cP when measured using a Wells-Brookfield HB cone/plate viscometer and a CP-51 cone at room temperature at a rotational speed of 2 rpm and a torque >10%, or a Brookfield DV-II+Pro viscometer with a spindle of 7, at 50 rpm, 1 minute.

In certain embodiments of any of the foregoing or following, the gelling agent is selected from a group of cross-linked polymers. The polymers can be covalently or physically cross-linked. The gelling agent can be selected from at least one of a hydrophilic material, a hygroscopic material and a hydrated polymer. The gelling agent can be polyanionic in charge character. In some embodiments, the gelling agent comprises carboxylic functional groups, which may have from 2 to 7 carbon atoms per functional group.

The gelling agent can be a synthetic polymer selected from the group consisting of vinyl polymers, polyoxyethylene-polyoxypropylene copolymers, poly(ethylene oxide), acrylamide polymers and derivatives or salts thereof. The gelling agent can be a vinyl polymer selected from the group of polyacrylic acid, polymethacrylic acid, polyvinyl pyrrolidone and polyvinyl alcohol. The gelling agent can be a carboxy vinyl polymer or a carbomer obtained by polymerisation of acrylic acid. The carboxy vinyl polymer or carbomer can be crosslinked.

In certain embodiments, the gelling agent is a high molecular weight, cross-linked polyacrylic acid polymer having a viscosity in the range of between about 10,000-100,000; between about 10,000-80,000; between about 15,000-80,000; between about 10,000-70,000; between about 15,000-70,000; between about 15,000-40,000, between about 10,000-60,000; between about 10,000-50,000; between about 10,000-40,000; between about 20,000-100,000; between about 25,000-90,000; between about 30,000-80,000; between about 30,000-70,000; between about 30,000-60,000; between about 25,000-40,000 cP. The polymer can be selected from the group consisting of, but not limited to Carbopol® 940, Carbopol® 980, ETD 2020 NF, Carbopol® 1382 Polymer, 71G NF, 971P NF, 974P NF, 980 NF, 981 NF, 5984 EP, ETF 2020 NF, ultrez 10 NF, ultrez 20, ultrez 21, 1342 NF, 934 NF, 934P NF, 940 NF, and 941 NF.

In certain embodiments, the gelling agent is a polyacrylic acid polymer cross-linked with alkyl acrylate or allyl pentaerythritol and is present in an amount of about 0.05% to about 5% by weight of the final composition, preferably about 0.1% to about 3%, more preferably about 0.1% to about 2%, more preferably about 0.5% to about 2% by weight of the final composition.

In certain embodiments of any of the foregoing or following, the gelling agent comprises a protein-based polymer, which can be selected from at least one of sodium hyaluronate, gelatin and collagen. The gelling agent can be gelatin and be present in an amount of equal to or more than about 4% by weight of the final composition. The gelling agent can be collagen and be present in an amount equal to or more than about 5% by weight of the final composition.

In certain embodiments of any of the foregoing or following, the gelling agent comprises a polysaccharide, which can be selected from at least one of starch, chitosan, chitin, agar, alginates, xanthan, carrageenan, guar gum, gellan gum, pectin, and locust bean gum. The gelling agent can be present in an amount equal to or more than about 0.01% by weight of the final composition.

In certain embodiments of any of the foregoing or following, the gelling agent comprises at least one glycol. The glycol can be selected from ethylene glycol and propylene glycol. The ethylene glycol can be polyethylene glycol.

In certain embodiments, the biophotonic composition can further comprise a humectant, such as, but not limited to, glycerine. The biophotonic composition may further comprise healing factors, preservatives, pH adjusters, chelators, or the like.

In certain embodiments of any of the foregoing or following, the biophotonic composition is encapsulated in a membrane, which may be breathable to allow permeation of gases but not liquids. The membrane may be translucent. The membrane may comprise materials such as, but not limited to, a lipid, a polymer and gelatin.

In certain embodiments of any of the foregoing or following, the biophotonic composition further comprises an oxygen-releasing agent which can be a peroxide or a peroxide-releasing agent or water. The oxygen-releasing agent can be selected from hydrogen peroxide, carbamide peroxide, benzoyl peroxide, peroxy acid, alkali metal peroxides, alkali metal percarbonates, peroxyacetic acid, and alkali metal perborates.

In certain embodiments of any of the foregoing or following, the first chromophore can be in an aqueous or alcohol solution in the composition. The gelling agent and the chromophore solution can form a hydrocolloid.

In certain embodiments of any of the foregoing or following, the first chromophore absorbs or emits light at a wavelength of 200-600 nm, 400-800 nm, or 400-600 nm. In certain embodiments of any of the foregoing or following, the first chromophore absorbs and/or emits light at a wavelength in the range of the visible spectrum. In some embodiments, the first chromophore is a fluorescent chromophore (fluorophore). The first chromophore can be a xanthene dye. The first chromophore can be selected from Eosin Y, Eosin B, Erythrosin B, Fluorescein, Rose Bengal and Phloxin B. The first chromophore can be present in an amount of between about 0.001% and about 40% by weight of the total composition, preferably between about 0.005% and about 2% by weight of the total composition, more preferably between about 0.01% and about 2% by weight of the total composition.

In certain embodiments of any of the foregoing or following, the composition further comprises a second chromophore. The first chromophore can have an emission spectrum that overlaps at least 5%, 6%, 7%, 8%, 9%, 10%, 11%, 12%, 13%, 14%, 15%, 20%, 25%, 30%, 35%, 40%, 45%, 50%, 55%, 60%, 65%, or 70% with an absorption spectrum of the second chromophore. In some embodiments, the first chromophore of the biophotonic topical composition has an emission spectrum that overlaps at least between about 1-10%, 5-15%, 10-20%, 15-25%, 20-30%, 25-35%, 30-40%, 35-45%, 50-60%, 55-65% or 60-70% with an absorption spectrum of the second chromophore when present.

In certain embodiments of any of the foregoing or following, the first chromophore transfers energy to the second chromophore upon illumination with a light. Illumination of the biophotonic topical composition with light causes a transfer of energy from the first chromophore to the second chromophore. In some embodiments, the second chromophore emits fluorescence and/or generates reactive oxygen species after absorbing energy from the first chromophore. At least one of the chromophores, for example, the first chromophore, can photobleach during illumination with light. At least one of the chromophores, for example, the first chromophore can emit fluorescence upon illumination with light. In certain embodiments, the biophotonic composition does not generate a substantial amount of heat following illumination with light.

In certain embodiments of any of the foregoing or following, the second chromophore absorbs and/or emits light at a wavelength in the range of the visible spectrum. In some embodiments, the second chromophore has an absorption wavelength that is relatively longer than that of the first chromophore, for example, between about 10-100 nm, between about 20-80 nm, between about 25-70 nm, or between about 30-60 nm longer.

In certain embodiments of any of the foregoing or following, the first chromophore is Eosin Y, and the second chromophore is one or more selected from Fluorescein, Phloxine B and Erythrosine B. In certain instances, the first chromophore is Eosin Y, and the second chromophore is Fluorescin. In some other instances, the first chromophore is Eosin Y, and the second chromophore is Phloxine B. In some other instances, the first chromophore is Eosin Y, and the second chromophore is Erythrosine B.

In certain embodiments of any of the foregoing or following, the first chromophore is Fluorescein, and the second chromophore is Eosin Y. Optionally, a third chromophore may be present such as, but not limited to, Rose Bengal. In other embodiments, the first chromophore is Rose Bengal. In some embodiments, the biophotonic composition comprises Eosin and Fluorescein. In other embodiments, the biophotonic composition comprises Eosin and Rose Bengal. In other embodiments, the biophotonic composition comprises Fluorescein and Rose Bengal. In other embodiments, the biophotonic composition comprises Fluorescein and Rose Bengal.

The second chromophore can be present in an amount of between about 0.0001% to about 40% by weight of the total composition, preferably between about 0.0001% to about 20% by weight of the total composition, preferably between about 0.0001% to about 10% by weight of the total composition, preferably between about 0.0001% to about 5% by weight of the total composition, and most preferably between about 0.0001% to about 2% by weight of the total composition.

In certain embodiments of any of the foregoing or following, the composition comprises a third chromophore. The third chromophore can be a chlorophyll (e.g. chlorophyllin, chlorophyll a, chlorophyll b) or saffron. Saffron can also be used with the first chromophore alone.

In certain embodiments of any of the foregoing or following, the pH of the composition is within the range of 4.0 to 7.0, preferably within the range of 4.0 to 6.5, more preferably within the range of 4.0 to 5.0. The pH of the composition may also be within the range of 6.0 to 8.0, preferably within the range of 6.5 to 7.5.

In certain embodiments of any of the foregoing or following, the biophotonic composition may be applied to or impregnated into a material such as a pad, a dressing, a woven or non-woven fabric or the like. The impregnated material may be used as a mask or a wound dressing. In certain embodiments or the foregoing or the following, the composition is applied to a substrate. As used herein, the term "substrate" refers to a material onto which the composition is applied. As used herein, the expression "treated substrate" refers to a substrate that has the composition applied thereto. The substrate may be of fibrous nature, where fibers, either woven or non-woven, form the interstices. Alternatively the substrate may be non-fibrous, such as a synthetic foam (such as, for example, a sponge). Specific examples of a substrate include, but are not limited to, fibrous textiles including natural fibers, such as either vegetal (such as cotton, linen, jute) or animal (such as wool and silk) or as well as mineral fibers (such as asbestos and viscose); chemical fibers, such as either synthetic or artificial fibers such as those comprising polyester, nylon, acetate, polypropolene and/or rayon; paper and paper products; products made from composites; products made from wood or wood byproducts, such as furniture materials and doors; products made from carbon fiber, products made from glass fiber, synthetic foam, such as polyethylene, polystyrene and polyurethane foam. Textiles may be woven, knitted or machine-knitted, or be present as a composite material (non-woven textile). In the case of composite materials, the fabric is not produced by wrap and weft or stitch formation, but by interlocking and/or cohesive and/or adhesive bonding of textile fibers. Non-woven fabrics are loose materials produced from spun fibers or filaments, in most cases made of polypropylene, polyester or viscose, the cohesion of which is generally provided by the fibers intrinsically holding together. In this regard, the individual fibers may have a preferred orientation (oriented or cross-laid non-woven fabrics), or be unoriented (entangled non-woven fabrics). The non-woven fabrics may be mechanically bonded by needle punching, stitching, or entangling by means of strong water jets. Adhesively bonded non-woven fabrics are produced by gluing the fibers together with liquid binding agents (for example, acrylate polymers, SBR/NBR, polyvinyl ester, polyurethane dispersions), or by melting or dissolving so-called binder fibers that are added to the non-woven fabric during its production. Non-woven material may be obtained from, for example, viscose, cotton, cellulose, jute, hemp, sisal, silk, wool, polypropylene, polyester, polyethylene terephthalate (PET), aramide, nylon, polyvinyl derivatives, polyurethanes, polylactide, polyhydroxyalkanoate, cellulose esters and/or polyethylene, and also mineral fibers, such as glass fibers or carbon fibers. Examples of fabrics also include blends of dual or multiple fibers, examples of which include, but are not limited to, those made of polyester/elastane blends, polyamids, polyamide/elastane blends, cotton/polyester/elastane blends, polyacrylonitriles, acetates, modal, lyocell and linens.

In certain embodiments of any of the foregoing or following, the biophotonic composition as defined herein further comprises at least one waveguide within or adjacent to the biophotonic composition. The waveguide can be a particle, a fibre or a fibrillar network made of a material which transmits and/or emits light.

In certain embodiments of any of the foregoing or following, the biophotonic composition is substantially free of opaque particles, such as silica.

In certain embodiments, the compositions of the present disclosure the gelling agent is a medium that provides a barrier such that the chromophore(s) and optionally other components of the topical biophotonic compositions are not in substantial contact with the target tissues, and/or do not penetrate the target tissues. The medium, such as the gelling agent, may provide a barrier rendering the biophotonic composition substantially resistant to leaching in use. The use of such biophotonic compositions in phototherapy would therefore not involve substantial direct contact of the target tissues with a chromophore, which may be potentially toxic the tissues or may cause undesired side effects.

In a further aspect, there is provided a method for treatment of non-healing wounds, comprising: applying topically to a non-healing wound a biophotonic composition as described herein and illuminating said biophotonic composition with light having a wavelength that overlaps with an absorption spectrum of a first chromophore.

In a further aspect, there is provided a method for promoting and/or stimulating repair and/or healing of non-healing wounds, comprising: applying topically to a non-healing wound a biophotonic composition as described herein; and illuminating said biophotonic composition with light having a wavelength that overlaps with an absorption spectrum of a first chromophore.

In a further aspect, there is provided a method for increasing the rate of repair in non-healing wounds, comprising: applying topically a biophotonic composition as described herein to a non-healing wound; and illuminating said biophotonic composition with light having a wavelength that overlaps with an absorption spectrum of the first chromophore.

In a further aspect there is provided a method for stimulating and/or promoting repair at the centre and/or edge of a non-healing wound, comprising: applying topically a biophotonic composition as described herein to a non-healing wound; and illuminating said biophotonic composition with light having a wavelength that overlaps with an absorption spectrum of the first chromophore.

In some embodiments, the stimulated repair is delayed at the edge compared to the centre of the non-healing wound. In other embodiments, the stimulated repair is increased at the centre compared to the edge of the non-healing wound.

In another aspect, there is provided a method for stimulating repair in at least the centre of a non-healing wound comprising: applying topically a biophotonic composition as described herein to a non-healing wound; and illuminating said biophotonic composition with light having a wavelength that overlaps with an absorption spectrum of the first chromophore.

In another aspect, there is provided a method for delaying repair at the edge of an active wound comprising: applying topically a biophotonic composition as described herein to an active wound; and illuminating said biophotonic composition with light having a wavelength that overlaps with an absorption spectrum of the first chromophore. In some embodiments, the wound is an activated non-healing wound.

In certain embodiments, stimulating repair can comprise inducing expression of growth factors or cytokines or both. The induced growth factor expression can be different at the centre than at an edge of the wound.

In certain embodiments, stimulating repair comprises increasing collagen expression. The collagen can be collagen I, III and/or procollagen.

In certain embodiments, stimulating repair comprises attracting repair cell progenitors and/or repair cells to the centre of the wound. Repair cells can comprise fibroblasts, keratinocytes and/or endothelial cells.

In certain embodiments, stimulating repair comprises inducing granulation in the absence of surgical trauma.

In certain embodiments, stimulating repair comprises at least one of inducing angiogenesis, epithelialization and remodelling.

From another aspect, there is provided a method for inducing growth factor or cytokine expression, or both, in non-healing wounds comprising: applying topically a biophotonic composition as described herein to a non-healing wound; and illuminating said biophotonic composition with light having a wavelength that overlaps with an absorption spectrum of the first chromophore.

From another aspect, there is provided a method for modulating collagen production in non-healing wounds comprising: applying topically a biophotonic composition as described herein to a non-healing wound; and illuminating said biophotonic composition with light having a wavelength that overlaps with an absorption spectrum of the first chromophore.

From another aspect, there is provided a method for modulating the morphometry of collagen during collagen formation in a healing wound comprising: applying topically a biophotonic composition as described herein to a healing wound; and illuminating said biophotonic composition with light having a wavelength that overlaps with an absorption spectrum of the first chromophore. The method can be applied during wound healing to reduce or minimize scarring.

In certain embodiments of the method, the non-healing wound as described herein includes for example chronic wounds, such as diabetic foot ulcers, pressure ulcers, and venous ulcers.

In certain embodiments, the method promotes reduction of scar tissue formation.

In certain embodiments, the method promotes disruption of biofilm.

In certain embodiments, the method accelerates the rate of wound healing.

In certain embodiments of any method of the present disclosure, the biophotonic composition is illuminated for any time period per treatment in which the biophotonic composition is activated, for example about 1 minute to about 30 minutes, preferably less than about 20 minutes, about 19 minutes, about 18 minutes, about 17 minutes, about 16 minutes, about 15 minutes, about 14 minutes, about 13 minutes, about 12 minutes, about 11 minutes, about 10 minutes, about 9 minutes, about 8 minutes, about 7 minutes, about 6 minutes, about 5 minutes, about 3 minutes, about 2 minutes or about 1 minute. The treatment time can correspond to, or be longer than a time it takes for the first chromophore to photobleach. In certain embodiments, the method of the present disclosure comprises a step of illuminating the biophotonic composition for a period of at least 30 seconds, at least 1 minute, at least 2 minutes, at least 3 minutes, at least 4 minutes, at least 5 minutes, at least 6 minutes, at least 7 minutes, at least 10 minutes, at least 11 minutes, at least 12 minutes, at least 13 minutes, at least 14 minutes, at least 15 minutes, at least 20 minutes, at least 25 minutes, or at least 30 minutes. In some embodiments, the biophotonic composition is illuminated for a period of at least 3 minutes. Preferably, the biophotonic composition is illuminated with visible non-coherent light, such as violet and/or blue light. Any other suitable light source can be used.

The distance of the light source from the biophotonic composition can be any distance which can deliver an appropriate light power density to the biophotonic composition and/or the skin tissue, for example about 5, about 6, about 7, about 8, about 9, about 10, about 15 or about 20 cm. The biophotonic composition is applied topically at any suitable thickness. Typically, the biophotonic composition is applied topically to skin or wounds at a thickness of at least about 2 mm, about 2 mm to about 10 mm.

In certain embodiments of the methods of the present disclosure, the biophotonic composition is removed from the site of a treatment following application of light. Accordingly, the biophotonic composition is removed from the site of treatment within at least 30 seconds, at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes or at least 30 minutes after application. In some embodiments, the biophotonic composition is removed after a period of at least 3 minutes post application of the biophotonic composition to treatment site, such as after about 3 minutes, after about 4 minutes, after about 5 minutes, after about 6 minutes, after about 7 minutes, after about 8 minutes, after about 9 minutes, or after about 10 minutes.

In certain other embodiments, the composition remains on the treatment area and can be re-illuminated as required. The biophotonic composition can be kept in place for up to one, two or three weeks. The composition can be re-illuminated with light, which may include ambient light, at various intervals. In this case, the composition may be covered-up in between the interval exposures to light. For example, the biophotonic composition may be soaked in a dressing and placed inside or over a wound and be left in place for an extended period of time (e.g. more than one day).

In certain embodiments of the method for biophotonic treatment of non-healing wounds, the treatment can be applied in or on the wound daily or once, twice, three times, four times, five times or six times a week, or at any other frequency. The total treatment time can be less than one week, one week, two weeks, three weeks, four weeks, five weeks, six weeks, seven weeks, eight weeks, nine weeks, ten weeks, eleven weeks, twelve weeks, 16 weeks, 24 weeks or any other length of time deemed appropriate. The total treatment time can be until the non-healing wound starts to form granulation tissue, or until wound closure.

In certain embodiments, during the total treatment time, a treatment rest period is introduced. For example, when the visible wound healing response slows down or plateaus, treatment can be paused. The treatment rest period (holiday period) can be for at least about 3 days to about 4 weeks. In certain embodiments, the treatment rest period is for about 3 days, about 4 days, about days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days. In certain embodiments, the treatment rest period can last from about 3 days to about 31 days. In certain embodiments, the treatment rest period is about 3 to 30 days, about 5 to 30 days, about 7 to 30 days, about 7 to 28 days, about 7 to 26 days, about 7 to 24 days, about 7 to 23 days, about 7 to 21 days, about 7 to 19 days, about 7 to 17 days, about 7 to 15 days, about 7 to 13 days, about 7 to 11 days, or about 14 to 30 days. After the treatment rest period, the biophotonic treatment can be resumed. It has been found by the inventors that such a rest period can lead to the re-activation or acceleration of the wound healing process. It has also been found by the inventors that larger wounds are more likely to benefit from such a rest period.

The disclosed methods for treating wounds may further include, for example, administering a systemic or topical drug before, during, in between, or after the biophotonic treatment, including any rest period. The drug may be an antibiotic, a hormone treatment, or any other pharmaceutical preparation which may help to treat the wounds. The combination of a systemic treatment together with a topical biophotonic treatment can reduce the duration of systemic treatment time.

The disclosed methods for treating wounds may also further include before, during, in between, or after the biophotonic treatment, including any rest period, the application of physical or chemical pressure on the wound to drive cells towards wound closure, and/or remove exudate. In one example, negative pressure is applied to the wound to remove exudate and to administer pressure on the wound edges towards closure. In another example, a filler may be placed within the wound to absorb any exudate. The filler may be a hydrogel which may remove exudate from the wound through osmosis. The filler may include a bacteriostatic component. The disclosed methods for treating wounds may also further include before, during, in between, or after the biophotonic treatment, including any rest period, the application of a hydrogel to the wound to keep the wound moist.

From a yet further aspect, there is provided use of a biophotonic composition, as described herein, for the treatment of non-healing wounds.

The biophotonic composition, as described herein, may also be used for stimulating/promoting repair in non-healing wounds or for increasing the rate of repair in chronic wounds.

The biophotonic composition, as described herein, can also be used for stimulating and/or promoting repair at the centre and/or at the edge of a non-healing wound. The stimulated repair can be delayed at the edge compared to the centre the non-healing wound. The stimulated repair can also be increased at the centre compared to the edge the non-healing wound.

There is also provided use of the biophotonic composition, as described herein, for stimulating repair in at least the centre of a non-healing wound.

There is also provided use of the biophotonic composition, as described herein, for delaying repair at the edge of an active wound. The wound may be an activated non-healing wound.

In certain embodiments of the above uses, stimulating repair comprises inducing expression of growth factors or cytokines, or both. The induced growth factor expression may be different at the centre than at edge of wound.

In certain embodiments of the above uses, stimulating repair comprises increasing collagen expression. The collagen can be collagen I, III and/or procollagen.

In certain embodiments of the above uses, stimulating repair comprises attracting repair cell progenitors and/or repair cells to the centre of the wound. The repair cells may comprise fibroblasts, keratinocytes and/or endothelial cells.

In certain embodiments of the above uses, stimulating repair comprises inducing granulation in the absence of surgical trauma.

In certain embodiments of the above uses, stimulating repair comprises at least one of inducing angiogenesis, epithelialization and remodelling.

There is also provided a biophotonic composition, as described herein, for inducing growth factor and/or cytokine expression in non-healing wounds.

There is also provided a biophotonic composition, as described herein, for modulating collagen production in non-healing wounds.

There is also provided a biophotonic composition, as described herein, for modulating the morphometry of collagen during collagen formation. This may reduce or minimize scarring.

From another aspect there is provided a kit comprising a composition as described herein, and one or more of a light source for activating the chromophore, instructions for use of the composition and/or the light source, a dressing, and a device for applying and/or removing the composition from a treatment area.

From another aspect, there is provided a kit comprising a first component comprising a first chromophore; and a second component comprising a gelling agent present in an amount sufficient to gel or thicken the composition and render the biophotonic composition substantially resistant to leaching such that less than 15% by weight of the total chromophore amount leaches out of the biophotonic composition in use.

From a yet further aspect, there is provided a kit comprising a first component comprising a first chromophore; and a second component comprising a gelling agent, wherein, in combination, the first component and the second component form a biophotonic composition substantially resistant to leaching such that less than 15% by weight of the total chromophore amount leaches out of the biophotonic composition in use. The first component and/or the second component may individually also be resistant to leaching.

From another aspect, there is provided a kit comprising: a first component comprising a composition as described herein, and a second component comprising an oxygen-releasing agent. Specifically, the first component may comprise a first chromophore and a gelling agent, wherein the composition of the first component, as well as the combined first and second component composition, are substantially resistant to leaching such that less than 15% by weight of the total chromophore amount leaches out of the biophotonic composition in use.

BRIEF DESCRIPTION OF THE DRAWINGS

FIGS. 29A and 29B illustrate immunostaining showing the expression of VEGF in a grade 2-3 wound at time zero, time 15 days, and time 30 days at the edge of the wound (29A) and at the center of the wound (29B) following treatment with a biophotonic composition and a method according to certain aspects of the present disclosure.

DETAILED DESCRIPTION

(1) Overview

Figure 1:
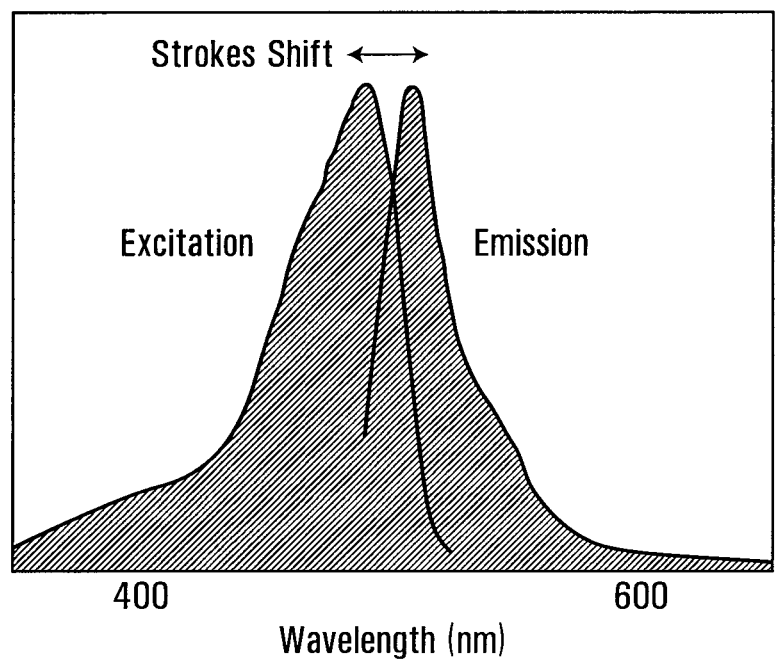
FIG. 1 illustrates a graph depicting the Stokes' shift.

Photodynamic therapy regimens have been developed to promote wound healing, rejuvenate facial skin and treat various skin disorders. However, these methods require direct application of a photosensitive agent to the target skin and/or uptake of the photosensitive agent into skin cells. As mentioned above, the direct contact of the photosensitive agent with the tissue can lead to undesired side-effects, including cellular damage/destruction and systemic or localized toxicity to the patient. Moreover, many existing photodynamic therapy regimens often demonstrate low therapeutic efficacy due to, for example, the poor uptake of the photosensitive agents into the skin cells at the target site. For this reason, may regimens require a wait time of between about one and 72 hours to allow the internalization of the photo sensitizer.

Phototherapy on the other hand utilizes the therapeutic effect of light. However, expensive and sophisticated light sources are often required to provide therapeutic wavelengths and intensities of light.

The present disclosure provides biophotonic compositions which are useful in phototherapy and which include photoactive chromophores which may emit a therapeutic light or may promote a therapeutic effect on a treatment site by activating other components of the biophotonic composition. In some instances, the chromophores are exogenous (i.e., chromophores that are not naturally present in skin or tissue onto which the biophotonic composition as defined herein is to be applied). The present disclosure also provides methods useful for promoting wound healing, in particular of non-healing wounds, which are distinguished from conventional photodynamic therapy.

Biophotonic therapy using the present compositions and methods does not rely on internalization of the chromophore into cells or substantial with the cells or target tissues. Therefore, the undesired side effects caused by direct contact may be reduced, minimized, or prevented. At most, the chromophore has surface contact with the tissue to which the composition is applied, which is likely to be short lasting due to short treatment times. Furthermore, unlike photodynamic therapy, biophotonic therapy with embodiments of the present biophotonic compositions does not rely on cell death or damage. In fact, in vitro studies presented herein show that a biophotonic composition according to an embodiment of the present disclosure reduced cell necrosis (Example 10).

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons, for example, by absorbing photons to emit photons or to transfer energy, for example, by absorbing photons to emit photons or to transfer energy.

"Gels" are defined as substantially dilute cross-linked systems. Gels may be semi-solids and exhibit substantially no flow when in the steady state at room temperature (e.g. about 20-25° C.). By steady state is meant herein during a treatment time and under treatment conditions. Gels, as defined herein, may be physically or chemically cross-linked. As defined herein, gels also include gel-like compositions such as viscous liquids.

"Topical" means as applied to body surfaces, such as the skin, mucous membranes, vagina, oral cavity, internal surgical wound sites, and the like.

Terms "chromophore", "photoactivating agent" and "photoactivator" are used herein interchangeably. A chromophore means a chemical compound, when contacted by light irradiation, is capable of absorbing the light. The chromophore readily undergoes photoexcitation and can then transfer its energy to other molecules or emit it as light.

"Photobleaching" means the photochemical destruction of a chromophore.

"Leaching" means the release of one or more components of a biophotonic composition (e.g., the chromophore(s) from the composition to the surrounding environment such as for example the wound site or into the tissue being treated with the composition. The leaching properties of the biophotonic composition can be measured by (i) placing a 2 mm thick layer of the biophotonic composition onto an upper side of a polycarbonate (PC) membrane having a diameter of 2.4 to 3 cm, a thickness of 10 µm and a pore size of 3 µm, a lower side of the membrane being in contact with a phosphate saline buffer solution in a receptor compartment, (ii) allowing the biophotonic composition to rest on the membrane upper surface at room temperature and pressure for a time corresponding to a treatment time using the biophotonic composition, and (iii) removing a sample of the solution from the receptor compartment and measuring the concentration of the chromophore in the solution.

The term "actinic light" is intended to mean light energy emitted from a specific light source (e.g., lamp, LED, or laser) and capable of being absorbed by matter (e.g. the chromophore or photoactivator defined above). The expression "actinic light" and the term "light" are used herein interchangeably. In a preferred embodiment, the actinic light is visible light.

As used herein, a "hygroscopic" substance is a substance capable of taking up water, for example, by absorption or adsorption even at relative humidity as low as 50%, at room temperature (e.g. about 20-25° C.).

"Impermeable membrane" means that the material contained within the membrane is sufficiently or substantially impermeable to the surrounding environment such that the migration of such material out of the membrane, and/or the migration of the environmental components (such as water) into the membrane, is so low as to having substantially no adverse impact on the function or activity of the materials retained within the membrane. The impermeable membrane may be 'breathable' in that gas flow through the membrane is permitted whilst the flow of liquid is not permitted. The impermeable membrane may also selectively allow the migration of some of the materials through the membrane but not others.

"Wound" means an injury to any tissue, including for example, acute, subacute, and non-healing wounds. Examples of wounds may include both open and closed wounds. Wounds include, for example, skin diseases that result in a break of the skin or in a wound, clinically infected wounds, burns, incisions, excisions, lesions, lacerations, abrasions, puncture or penetrating wounds, gunshot wounds, surgical wounds, contusions, hematomas, crushing injuries, ulcers, scarring (cosmesis), wounds caused by periodontitis.

"Non-healing wounds" means wounds that do not heal in an orderly set of stages and a predictable amount of time and rate in the way that most normally-healing wounds heal, and non-healing wounds include, but are not limited to: incompletely healed wounds, delayed healing wounds, impaired wounds, difficult to heal wounds and chronic wounds. Examples of such non-healing wounds include diabetic foot ulcers, vascultic ulcers, pressure ulcers, decubitus ulcers, infectious ulcers, trauma-induced ulcers, burn ulcers, ulcerations associated with pyoderma gangrenosum, dehiscent and mixed ulcers. A non-healing wound may include, for example, a wound that is characterized at least in part by 1) a prolonged inflammatory phase, 2) a slow forming extracellular matrix, and/or 3) a decreased rate of epithelialization or closure.

"Chronic wound" means a wound that has not healed within about 4 to 6 weeks. Chronic wounds include venous ulcers, venous stasis ulcers, arterial ulcers, pressure ulcers, diabetic ulcers, and diabetic foot ulcers.

(3) Biophotonic Topical Compositions

The present disclosure provides biophotonic compositions. Biophotonic compositions are compositions that are activated by light (e.g., photons) of specific wavelength. These compositions comprise at least one chromophore which is activated by light and accelerates the dispersion of light energy, which leads to light carrying on a therapeutic effect on its own, and/or to the photochemical activation of other agents that may be present in the composition (e.g., acceleration in the breakdown process of peroxide, which is an oxygen-releasing agent) when such compound is present in the composition or at the treatment site, leading to the formation of oxygen radicals, such as singlet oxygen. The composition may comprise an oxygen-releasing agent which, when mixed with the first chromophore and subsequently activated by light, can be photochemically activated which may lead to the formation of oxygen radicals, such as singlet oxygen.

In some aspects, the present disclosure provides biophotonic compositions comprising at least a first chromophore in a medium, wherein the composition is substantially resistant to leaching such that a low or negligible amount of the chromophore leaches out of the biophotonic composition into a treatment site (e.g., tissue) onto which the composition is applied during treatment. In certain embodiments, this is achieved by the medium comprising a gelling agent which slows or restricts movement or leaching of the chromophore. In other embodiments, this is achieved by provision of an encapsulating membrane around the first chromophore in the medium. In this way, contact of the chromophore and the tissue can be minimized or avoided. The encapsulated composition can be used in conjunction with a peroxide composition applied in between the target tissue and the encapsulated composition.

In some aspects, biophotonic compositions of the present disclosure do not stain the tissue onto which they are topically applied during treatment. Staining is determined by visually assessing whether the biophotonic composition colorizes white test paper saturated with 70% by volume ethanol/30% by volume water solution placed in contact with the biophotonic composition for a period of time corresponding to a desired treatment time. In some embodiments, a biophotonic composition of the present disclosure does not visually colorize white test paper saturated with a 70% by volume ethanol/30% by volume water solution placed in contact with the biophotonic composition under atmospheric pressure for a time corresponding to a desired treatment time. In certain embodiments, the time corresponding to a treatment time is at least about 5 minutes, at least about 6 minutes, at least about 7 minutes, at least about 8 minutes, at least about 9 minutes, at least about 10 minutes, 15 minutes, 20 minutes, 25 minutes or 30 minutes.

When a chromophore absorbs a photon of a certain wavelength, the chromophore becomes excited (i.e. photoactivated). This is an unstable condition and the molecule tries to return to the ground state, and in doing so releases the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a treatment site on to which the biophotonic composition is topically applied. Differing wavelengths of light may have different and complementary therapeutic effects on tissue. Stokes' shift is illustrated in FIG. 1.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues. Moreover, in embodiments of the composition containing oxygen-releasing agent(s), micro-foaming within the composition has been observed which may be associated with the generation of oxygen species by the photoactivated chromophores. This may have a physical impact on the tissue to which the composition is applied, for example by dislodging biofilm and debridement of necrotic tissue or providing pressure stimulation. The biofilm can also be pre-treated with an oxygen-releasing agent to weaken the biofilm before treating with the composition of the present disclosure.

Certain embodiments of the biophotonic compositions of the present disclosure are substantially transparent or translucent, or both, and/or have high light transmittance in order to permit light dissipation into and through the composition. In this way, the area of tissue under the composition can be treated both with the fluorescent light emitted by the composition and the light irradiating the composition to activate it, which may benefit from the different therapeutic effects of light having different wavelengths.

The % transmittance of the biophotonic composition can be measured in the range of wavelengths from 250 nm to 800 nm using, for example, a Perkin-Elmer Lambda 9500 series UV-visible spectrophotometer. Alternatively, a Synergy HT spectrophotometer (BioTek Instrument, Inc.) can be used in the range of wavelengths from 380 nm to 900 nm.

Transmittance is calculated according to the following equation:

$$A_\lambda = \log_{10}\frac{I_0}{I} = \log_{10}\frac{1}{T}.$$

where A is absorbance, T is transmittance, $I_0$ is intensity of radiation before passing through material, I is intensity of light passing through material.

The values can be normalized for thickness. As stated herein, % transmittance (translucency) is as measured for a 2 mm thick sample at a wavelength of 526 nm. It will be clear that other wavelengths can be used.

In some embodiments, the biophotonic composition has a transparency or translucency that exceeds 15%, 20%, 25%, 30%, 35%, 40%, 45%, 50%, 55%, 60%, 65%, 70%, 75%, 80%, or 85%. In some embodiments, the transparency exceeds 70%, 80%, 85%, 86%, 87%, 88%, 89%, 90%, 91%, 92%, 93%, 94%, 95%, 96%, 97%, 98% or 99%. All transmittance values reported herein are as measured on a 2 mm thick sample using the Synergy HT spectrophotometer at a wavelength of 526 nm.

Embodiments of the biophotonic compositions of the present disclosure are for topical uses. The biophotonic composition can be in the form of a semi-solid or viscous liquid, having properties such that less than 15% by weight of the total chromophore amount leaches out of the biophotonic composition in use. Preferably, the biophotonic compositions are a gel or are gel-like, including viscous liquids, and which have a spreadable consistency at room temperature (e.g. about 20-25° C.), prior to illumination. By spreadable is meant that the composition can be topically applied to a treatment site at a thickness of about 2 mm. Spreadable compositions can conform to a topography of a treatment site, e.g. a wound. This can have advantages over a non-conforming material in that a better and/or more complete illumination of the treatment site can be achieved.

Examples components of the composition of the present disclosure are detailed as below.

(a) Chromophores

The biophotonic compositions of the present disclosure comprise one or more chromophores, that is to say that they, are not naturally present in skin or tissue onto which the biophotonic composition as defined herein is to be applied. The chromophores are contained or held within the biophotonic composition such that they do not substantially contact the target tissue to which the biophotonic composition is applied during a treatment time. In this way, the beneficial and therapeutic properties of the chromophore can be harnessed without the possibly damaging effects caused by chromophore-to-cell contact.

Suitable chromophores can be fluorescent dyes (or stains), although other dye groups or dyes (biological and histological dyes, food colorings, carotenoids, and other dyes) can also be used. Suitable chromophores can be those that are Generally Regarded As Safe (GRAS), although chromophores which are not well tolerated by the skin or other tissues can be included in the biophotonic composition as contact with the skin is minimal in use due to the leaching-resistant nature of the biophotonic composition.

In certain embodiments, the topical biophotonic composition of the present disclosure comprises a first chromophore which undergoes partial or complete photobleaching upon application of light. By photobleaching is meant a photochemical destruction of the chromophore, which can generally be visualized as a loss of color.

In some embodiments, the first chromophore absorbs and/or emits at a wavelength in the range of the visible spectrum, such as at a wavelength of about 380-800 nm, 380-700, or 380-600 nm. In other embodiments, the first chromophore absorbs/or emits at a wavelength of about 200-800 nm, 200-700 nm, 200-600 nm or 200-500 nm. In one embodiment, the first chromophore absorbs/or emits at a wavelength of about 200-600 nm. In some embodiments, the first chromophore absorbs/or emits light at a wavelength of about 200-300 nm, 250-350 nm, 300-400 nm, 350-450 nm, 400-500 nm, 400-600 nm, 450-650 nm, 600-700 nm, 650-750 nm or 700-800 nm.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic composition of the present disclosure.

The biophotonic compositions disclosed herein may include at least one additional chromophore. Combining chromophores may increase photo-absorption by the combined dye molecules and enhance absorption and photo-biomodulation selectivity.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore (see FIG. 2).

Figure 3:
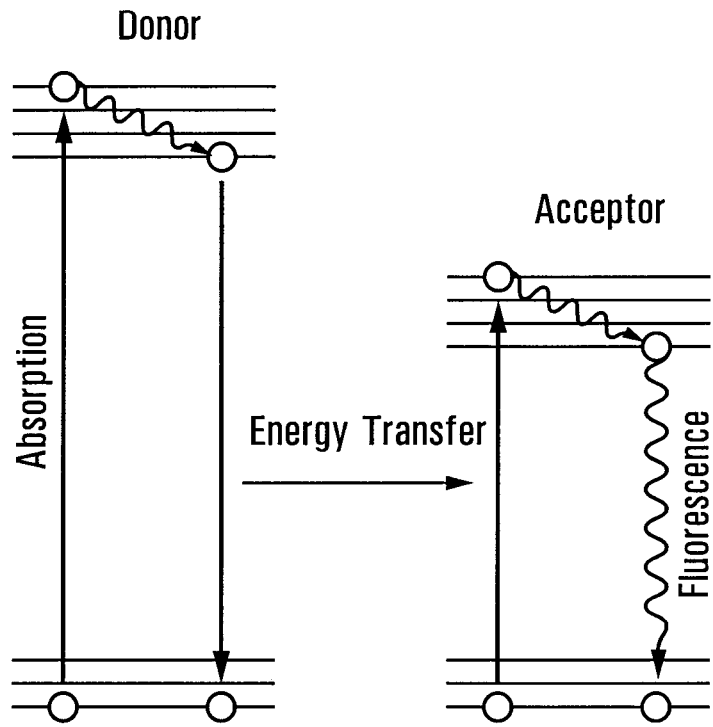
FIG. 3 illustrates a schematic representation of a Jablonski diagram of the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, it is thought that the more overlap there is between the donor chromophere's emission spectra and the acceptor chromophore's absorption spectra, the better a donor chromophore can transfer energy to the acceptor chromophore.

In certain embodiments, the biophotonic topical composition of the present disclosure further comprises a second chromophore. In some embodiments, the first chromophore has an emission spectrum that overlaps at least about 80%, 75%, 70%, 65%, 60%, 55%, 50%, 45%, 40%, 35%, 30%, 25%, 20%, 15%, or at least about 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65%, 60-70%, 65-75%, 70-80%, 75-80% with an absorption spectrum of the second chromophore.

Figure 2:
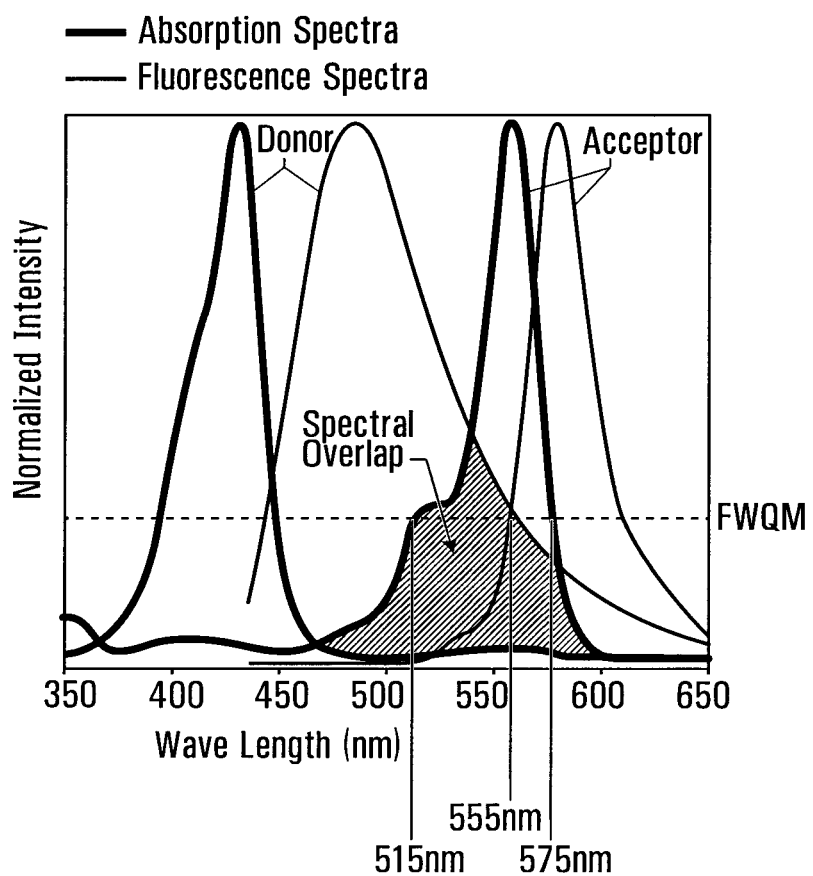
FIG. 2 illustrates a graph indicating the absorption and emission spectra of donor and acceptor chromophores. The spectral overlap between the absorption spectrum of the acceptor chromophore and the emission spectrum of the donor chromophore is also shown.

% spectral overlap, as used herein, means the % overlap of a donor chromophore's emission wavelength range with an acceptor chromophore's absorption wavelength range, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

As discussed above, the application of light to the compositions of the present disclosure can result in a cascade of energy transfer between the chromophores. In certain embodiments, such a cascade of energy transfer provides photons that penetrate the epidermis, dermis and/or mucosa at the target tissue, including, such as, a site of wound, or a tissue afflicted with acne or a skin disorder. In some embodiments, such a cascade of energy transfer is not accompanied by concomitant generation of heat. In some other embodiments, the cascade of energy transfer does not result in tissue damage.

Optionally, when the biophotonic topical composition comprises a first and a second chromophore, the first chromophore is present in an amount of about 0.005-40% per weight of the composition, and the second chromophore is present in an amount of about 0.001-40% per weight of the composition. In certain embodiments, the total weight per weight of chromophore or combination of chromophores may be in the amount of about 0.005-40.001% per weight of the composition. In certain embodiments, the first chromophore is present in an amount of about 0.005-1%, 0.01-2%, 0.02-1%, 0.02-2%, 0.05-1%, 0.05-2%, 0.05-1%, 0.05-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-1%, 0.001-2%, 0.001-0.01%, 0.01-0.1%, 0.1-1.0%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the total weight per weight of chromophore or combination of chromophores may be in the amount of about 0.005-1%, 0.01-2%, 0.05-2%, 0.5-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In certain embodiments, the emitted fluorescent light has a power density of between 0.005 to about 10 mW/cm$^2$, about 0.5 to about 5 mW/cm$^2$.

Suitable chromophores that may be used in the biophotonic topical compositions of the present disclosure include, but are not limited to the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene Derivatives

Exemplary xanthene dyes include but are not limited to eosin B; eosin B (4',5'-dibromo,2',7'-dinitr-o-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachlor-o-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachlorotetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-a-mino-phenothiazine; and 1,9-dimethyl-3-diethyl-amino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocarmine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any of the chromophores listed above, or a combination thereof, so as to provide a biophotonic impact at the application site. This is a distinct application of these agents and differs from the use of chromophores as simple stains or as a catalyst for photo-polymerization.

Chromophores can be selected, for example, on their emission wavelength properties in the case of fluorophores, on the basis of their energy transfer potential, their ability to generate reactive oxygen species, or their antimicrobial effect. These needs may vary depending on the condition requiring treatment. For example, chlorophylls may have an antimicrobial effect on bacteria.

In some embodiments, the composition includes Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. This absorbed and re-emitted light is thought to be transmitted throughout the composition, and also to be transmitted into the site of treatment.

In further embodiments, the composition includes the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine. Other synergistic chromophore combinations are also possible.

By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when photoactivated in the presence of molecular oxygen, however it has a low quantum yield in terms of emitted fluorescent light. Rose Bengal has a peak absorption around 540 nm and so is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal as well as emitting some energy as fluorescence.

Chromophore combinations can also have a synergistic effect in terms of their photoactivated state. For example, two chromophores may be used, one of which emits fluorescent light when activated in the blue and green range, and the other which emits fluorescent light in the red, orange and yellow range, thereby complementing each other and irradiating the target tissue with a broad wavelength of light having different depths of penetration into target tissue and different therapeutic effects.

(b) Gelling Agent

The present disclosure provides biophotonic compositions that comprise at least a first chromophore and a gelling agent, wherein the gelling agent provides a barrier such that the chromophore(s) of the biophotonic topical compositions are substantially not in contact with the target tissue. The gelling agent, when present in the biophotonic compositions of the present disclosure, can render the compositions substantially resistant to leaching such that the chromophore(s) or photosensitive agent(s) of the biophotonic topical compositions are not in substantial contact with the target tissue.

In certain embodiments, the biophotonic topical composition allows less than 30%, 25%, 20%, 15%, 10%, 9%, 78%, 7%, 6%, 5%, 4%, 3%, 2%, 1%, 0.8%, 0.5% or 0.1%, or essentially none of said chromophore content to leach out of the biophotonic composition.

In some embodiments, the biophotonic composition limits leaching of the first chromophore such that less than 15% by weight of the total chromophore amount leaches out of the biophotonic composition in use is topically applied onto tissue and illuminated with light. In some embodiments, the biophotonic composition limits leaching of the first chromophore such that less than 30%, 25%, 20%, 15%, 10%, 9%, 78%, 7%, 6%, 5%, 4%, 3%, 2%, 1%, 0.8%, 0.5% or 0.1% or essentially 0% of total chromophore amount can leach out into tissue during a treatment time in which the composition is topically applied onto tissue and illuminated with light. In some embodiments, the treatment time is at least about 5 minutes, at least about 10 minutes, at least about 15 minutes, at least about 20 minutes, at least about 25 minutes or at least about 30 minutes.

Figure 4:
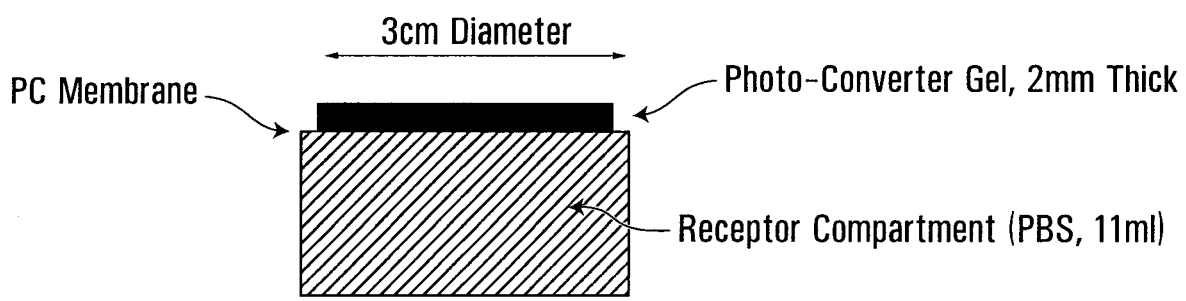
FIG. 4 illustrates a schematic representation of the experimental setup of an in vitro release test for evaluating leaching of the chromophore(s) of biophotonic compositions according to certain embodiments of the present disclosure.

Leaching can be determined as described in Example 5 (see FIG. 4). In some embodiments, a biophotonic composition of the present disclosure allows less than 30%, 25%, 20%, 15%, 10%, 9%, 78%, 7%, 6%, 5%, 4%, 3%, 2%, 1%, 0.8%, 0.5% or 0.1% or essentially 0% of the total chromophore amount to leach out of the biophotonic composition as through a porous membrane into an aqueous solution when the biophotonic composition is placed in contact with the aqueous solution through the porous membrane for a time corresponding to a desired treatment time. In certain embodiments, the time corresponding to a treatment time is at least about 5 minutes, at least about 6 minutes, at least about 7 minutes, at least about 9 minutes, at least about 10 minutes, 15 minutes, 20 minutes, 25 minutes or 30 minutes.

A gelling agent for use according to the present disclosure may comprise any ingredient suitable for use in a topical biophotonic formulation as described herein. The gelling agent may be an agent capable of forming a cross-linked matrix, including physical and/or chemical cross-links. The gelling agent is preferably biocompatible, and may be biodegradable. In some embodiments, the gelling agent is able to form a hydrogel or a hydrocolloid. An appropriate gelling agent is one that can form a viscous liquid or a semisolid. In preferred embodiments, the gelling agent and/or the composition has appropriate light transmission properties. The gelling agent preferably allows biophotonic activity of the chromophore(s). For example, some chromophores require a hydrated environment in order to fluoresce. The gelling agent may be able to form a gel by itself or in combination with other ingredients such as water or another gelling agent, or when applied to a treatment site, or when illuminated with light.

The gelling agent according to various embodiments of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); and polyvinylamines.

The gelling agent according to certain embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or 100,000, or 1,000,000) and/or cross-linked polyacrylic acid polymer. In some embodiments, the polymer is a polyacrylic acid polymer and has a viscosity in the range of about 10,000-100,000; 10,000-80,000; 15,000-80,000; 10,000-70,000; 15,000-70,000; 10,000-60,000; 10,000-50,000; 10,000-40,000; 20,000-100,000; 25,000-90,000; 30,000-80,000; 30,000-70,000; 30,000-60,000; 25,000-40,000 cP. In certain embodiment, the polymer is a high molecular weight, and/or cross-linked polyacrylic acid polymer, where the polyacrylic acid polymer has a viscosity in the range of about 10,000-80,000 cP.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has approximately pH 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp.) 8:S-135 (1991)), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In certain embodiments, the carbomer is Carbopol® 980 NF, ETD 2020 NF, Ultrez 10 NF, Ultrez 21 or 1382 Polymer, 1342 NF, 940 NF. For example, 0.05 to 10%, preferably 0.5 to 5%, more preferably 1 to 3% by weight of the final composition of a high molecular weight carbopol can be present as the gelling agent and which can form a gel having a viscosity of more than about 10,000 cP, or preferably more than about 15,000 cP.

In certain embodiments, the gelling agent comprises a hygroscopic and/or a hydrophilic material which may be used for their water attracting properties, which may also prevent or limit leaching of the chromophore. The hygroscopic or hydrophilic material may include, but is not limited to, glucosamine, polysaccharides, glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate).

The one or more gelling agents can be selected according to their ability to prevent chromophore leaching. For example, gelling agents which increase the viscosity of the biophotonic composition can be selected. In some embodiments, the viscosity of the biophotonic composition is 15,000-100,000, 15,000-90,000, 15,000-80,000, 20,000-80,000, 20,000-70,000, 20,000-50,000, 10,000-50,000, 15,000-50,000, 10,000-40,000, 15,000-40,000 cP. A composition with sufficiently high viscosity parameters can prevent or limit the leaching of chromophores from the composition. Viscosity of the biophotonic compositions of the present disclosure is as measured using a cone/plate viscometer (Wells-Brookfield) using a CP-51 and measuring viscosity at a speed of 2 rpm and making sure that the torque is >10%. Spindle must rotate at least 5 times before a viscosity reading is taken. Alternatively a Brookfield DV-II+Pro viscometer with Spindle 7, 50 rpm, 1 minute can be used.

Gelling agents which include lipids or other coating agents which can coat the chromophores can also be used to limit or prevent leaching. The gelling agent may be protein-based/naturally derived material such as sodium hyaluronate, gelatin or collagen, or the like. The gelling agent may be a polysaccharide such as starch, chitosan, chitin, agarose, agar, locust bean gum, carrageenan, gellan gum, pectin, alginate, xanthan, guar gum, and the like.

In one embodiment, the composition includes up to about 2% by weight of the final composition of sodium hyaluronate as the single gelling agent. In another embodiment, the composition includes more than about 4%, preferably more than about 5%, by weight of the final composition of gelatin as the single gelling agent. In another embodiment, the composition includes up to about 10%, preferably up to about 8%, starch as the single gelling agent. In yet another embodiment, the composition includes more than about 5%, preferably more than about 10%, by weight of the final composition of collagen as the gelling agent. In further embodiments, about 0.1-10%, or about 0.5-3%, by weight of the final composition of chitin is used as the gelling agent. In other embodiments, 0.5%-5% by weight of the final composition of corn starch, or 5-10% by weight of the final composition of starch is used as the gelling agent. In certain other embodiments, more than 2.5 wt % by weight of the final composition of alginate can be used in the composition as the gelling agent. In other embodiments, the percentages by weight percent of the final composition of the gelling agents are as follows: cellulose gel (about 0.3-2.0%), konjac gum (0.5-0.7%), carrageenan gum (0.02-2.0%), xanthan gum (0.01-2.0%), acacia gum (3-30%), agar (0.04-1.2%), guar gum (0.1-1%), locust bean gum (0.15-0.75%), pectin (0.1-0.6%), tara gum (0.1-1.0%), polyvinylpyrrolidone (1-5%), sodium polyacrylate (1-10%). Other gelling agents can be used in amounts sufficient to gel the composition or to sufficiently thicken the composition to avoid or minimize leaching of the chromophore(s). It will be appreciated that lower amounts of the above gelling agents may be used in the presence of another gelling agent or a thickener.

The biophotonic composition of the present disclosure may be further encapsulated, e.g., in a membrane. Such a membrane may be transparent, and/or substantially, or fully impermeable. The membrane may be impermeable to liquid but permeable to gases such as air. In certain embodiments, the composition may form a membrane that encapsulates the chromophore(s) of the biophotonic topical composition, where the membrane may be substantially impermeable to liquid and/or gas.

In certain embodiments, the retention of the chromophore in the composition during the treatment time can be achieved by providing a membrane around a chromophore(s) in a carrier medium. In this case, it is the membrane which limits or stops leaching of the chromophore such as by providing a barrier. The carrier medium can be a liquid encapsulated by the membrane, wherein the membrane is sufficiently resistant to chromophore leaching such that less than 15% by weight of the total chromophore amount leaches out of the biophotonic composition in use. The membrane may be formed of one or more lipidic agents, polymers, gelatin, cellulose or cyclodextrins, or the like. Preferably, the membrane is translucent or transparent to allow light to infiltrate to and from the chromophore(s). In one embodiment, the composition is a dendrimer with an outer membrane comprising poly(propylene amine). In another embodiment, the outer membrane comprises gelatin.

(c) Oxygen-Releasing Agents

According to certain embodiments, the compositions of the present disclosure may optionally further comprise one or more additional components, such as oxygen-releasing agents. For instance, the biophotonic topical composition of the present disclosure may optionally comprise oxygen-releasing agents as a source of oxygen. Peroxide compounds are oxygen-releasing agents that contain the peroxy group (R—O—O—R), which is a chainlike structure containing two oxygen atoms, each of which is bonded to the other and a radical or some element.

When a biophotonic composition of the present disclosure comprising an oxygen-releasing agent is illuminated with light, the chromophore(s) are excited to a higher energy state. When the chromophore(s)' electrons return to a lower energy state, they emit photons with a lower energy level, thus causing the emission of light of a longer wavelength (Stokes' shift). In the proper environment, some of this energy release is transferred to oxygen or the reactive hydrogen peroxide and causes the formation of oxygen radicals, such as singlet oxygen. The singlet oxygen and other reactive oxygen species generated by the activation of the biophotonic composition are thought to operate in a hormetic fashion. That is, a health beneficial effect that is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the composition can also produce an antibacterial effect. The extreme sensitivity of bacteria to exposure to free radicals makes the composition of the present disclosure a de facto bactericidal composition.

As stated above, the generation of oxygen species by the composition in some embodiments is accompanied by the micro-foaming which can contribute to debridement or dislodging of biofilm at the site of application. This can allow for the improved penetration of the activating and/or fluorescence light to the treatment site for example to deactivate bacterial colonies leading to their reduction in number.

Suitable oxygen-releasing agents that may be included in the composition include, but are not limited to:

Hydrogen peroxide ($H_2O_2$) is the starting material to prepare organic peroxides. $H_2O_2$ is a powerful oxygen-releasing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is from about 0.1% to about 6%.

Urea hydrogen peroxide (also known as urea peroxide, carbamide peroxide or percarbamide) is soluble in water and contains approximately 35% hydrogen peroxide. Carbamide peroxide for use in this composition can be used as a gel, for example with 16% carbamide peroxide that represents 5.6% hydrogen peroxide, or 12% carbamide peroxide. A suitable range of concentration over which urea peroxide can be used in the present composition is from about 0.3% to about 16%. Urea peroxide breaks down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which is toxic. A suitable range of concentration over which benzoyl peroxide can be used in the present composition is from about 2.5% to about 5%.

Specific oxygen-releasing agents that that are preferably used in the materials or methods of this disclosure include, but are not limited to hydrogen peroxide, carbamide peroxide, or benzoyl peroxide. Peroxy acid, alkali metal peroxides, alkali metal percarbonates, peroxyacetic acid, and alkali metal perborates can also be included as the oxygen-releasing agent. Oxygen-releasing agents can be provided in powder, liquid or gel form. Alternatively, the oxygen-releasing agents may also be applied to the tissue site separately to the composition. Alternatively, the composition may include an amount of oxygen-releasing agent, which is augmented by the separate application of oxygen-releasing agents to the treatment site.

In the compositions and methods of the present disclosure, additional components may optionally be included, or used in combination with the biophotonic compositions as described herein. Such additional components include, but are not limited to, healing factors, growth factors, antimicrobials, wrinkle fillers (e.g. botox, hyaluronic acid or polylactic acid), collagens, anti-virals, anti-fungals, antibiotics, drugs, and/or agents that promote collagen synthesis. These additional components may be applied to the wound, skin or mucosa in a topical fashion, prior to, at the same time of, and/or after topical application of the biophotonic composition of the present disclosure, and may also be systemically administered. Suitable healing factors, antimicrobials, collagens, and/or agents that promote collagen synthesis are discussed below:

(d) Healing Factors

Healing factors comprise compounds that promote or enhance the healing or regenerative process of the tissues on the application site of the composition. During the photoactivation of the composition of the present disclosure, there may be an increase of the absorption of molecules at the treatment site by the skin, wound or the mucosa. An augmentation in the blood flow at the site of treatment is observed for a period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Studies have shown hyaluronic acid appearing in the early stages of healing to physically create room for white blood cells that mediate the immune response. It is used in the synthesis of biological scaffolds for wound healing applications and in wrinkle treatment. A suitable range of concentration over which hyaluronic acid can be used in the present composition is from about 0.001% to about 3%.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt and including glucosamine sulfate sodium chloride. Glucosamine shows a number of effects including an anti-inflammatory activity, stimulation of the synthesis of proteoglycans and the synthesis of proteolytic enzymes. A suitable range of concentration over which glucosamine can be used in the present composition is from about 0.01% to about 3%.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing.

Also, saffron can act as both a chromophore and a healing factor, and as a potentiator. Other healing agents can also be included such as growth factors.

(e) Antimicrobials

Antimicrobials kill microbes or inhibit their growth or accumulation. Examples of antimicrobials (or antimicrobial agent) are recited in U.S. Patent Application Publications 2004/0009227 and 2011/0081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Examples of phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol-; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Examples of resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2, 4-dihydroxydiphenyl methane.

Examples of bisphenolic antimicrobial agents that can be used in the disclosure include, but are not limited to: 2,2'-methylene bis-(4-chlorophenol); 2,4,4'trichloro-2'-hydroxy-diphenyl ether, which is sold by Ciba Geigy, Florham Park, N.J. under the tradename Triclosan®; 2,2'-methylene bis-(3,4,6-trichlorophenol); 2,2'-methylene bis-(4-chloro-6-bromophenol); bis-(2-hydroxy-3,5-dichlorop-henyl) sulphide; and bis-(2-hydroxy-5-chlorobenzyl)sulphide.

Examples of benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Examples of halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Examples of polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Examples of thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Examples of trichloromethylthioimides that can be used in the disclosure include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Examples of natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; eucalyptus; vervain; peppermint; gum benzoin; basil; fennel; fir; balsam; menthol; ocmea origanuin; hydastis; carradensis; *Berberidaceac daceae; Ratanhiae longa*; and *Curcuma longa*. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Examples of metal salts that can be used in the disclosure include, but are not limited to, salts of metals in groups 3a-5a, 3b-7b, and 8 of the periodic table. Examples of examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. An example of the metal-ion based antimicrobial agent is sold under the tradename HealthShield®, and is manufactured by HealthShield Technology, Wakefield, Mass.

Examples of broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, and U.S. Pat. Appl. Publ. Nos. 2004/0009227 and 2011/0081530.

(4) Methods of Use

In some implementations of the embodiments of the present disclosure, the biophotonic compositions of the present disclosure may promote wound healing or tissue repair, especially in non-healing wounds. The biophotonic compositions of the present disclosure may also be used for treating acute inflammation, especially in non-healing wounds. Therefore, in some aspects, the present disclosure may provide for a method of providing biophotonic therapy to a non-healing wound, where the method promotes or stimulates healing of that wound.

In certain embodiments, the present disclosure provides a method for providing a biophotonic therapy to a non-healing wound, the method comprising: applying (e.g., by topical application so as to cover the entirety of the wound) a biophotonic composition of the present disclosure to a site of the non-healing wound, and illuminating the biophotonic composition with light having a wavelength that overlaps with an absorption spectrum of the chromophore(s) of the biophotonic composition.

In one aspect, the present disclosure provides a method for providing biophotonic therapy to a non-healing wound, comprising: topically applying to the wound a biophotonic composition comprising a first chromophore; and illuminating said biophotonic composition with light having a wavelength that overlaps with an absorption spectrum of the first chromophore; wherein the biophotonic composition is substantially resistant to leaching such that it limits leaching of the chromophore into the tissue during treatment. In some embodiments, less than 30%, 25%, 20%, 15%, 10%, 9%, 8%, 7%, 6%, 5%, 4%, 3%, 2%, 1%, 0.8%, 0.5% or 0.1% or essentially 0% by weight of the total chromophore amount leaches out of the biophotonic composition into the wound or tissue during treatment.

In another aspect, the present disclosure provides a method for treating a non-healing wound or providing biophotonic therapy to a non-healing wound, comprising: topically applying a biophotonic composition comprising a first chromophore and a gelling agent to a site of the wound; and illuminating said biophotonic composition with light having a wavelength that overlaps with an absorption spectrum of the first chromophore; wherein the gelling agent blocks substantial leaching of the chromophores into the site of a wound during treatment. In some embodiments, less than 30%, 25%, 20%, 15%, 10%, 9%, 8%, 7%, 6%, 5%, 4%, 3%, 2%, 1%, 0.8%, 0.5% or 0.1% or essentially 0% by weight of the total chromophore amount leaches out of the biophotonic composition into the wound or tissue during treatment.

In other embodiments, the present disclosure provides a method for treating acute inflammation, comprising: topically applying a biophotonic composition to a target skin tissue with acute inflammation, wherein the biophotonic composition comprises a first chromophore; illuminating said biophotonic composition with light having a wavelength that overlaps with an absorption spectrum of the first chromophore; wherein the biophotonic composition is substantially resistant to leaching such that it limits leaching of the chromophore into tissue during treatment. In some embodiments, less than 30%, 25%, 20%, 15%, 10%, 9%, 8%, 7%, 6%, 5%, 4%, 3%, 2%, 1%, 0.8%, 0.5% or 0.1% or essentially 0% by weight of the total chromophore amount leaches out of the biophotonic composition into the tissue during treatment.

In another aspect, the present disclosure provides a method for treating acute inflammation, comprising: topically applying a biophotonic composition comprising a first chromophore to skin afflicted with acute inflammation; and illuminating said biophotonic composition with light having a wavelength that overlaps with an absorption spectrum of the first chromophore; wherein the biophotonic composition is substantially resistant to leaching such that it blocks substantial leaching of the chromophores into the skin during treatment. In some embodiments, less than 30%, 25%, 20%, 15%, 10%, 9%, 8%, 7%, 6%, 5%, 4%, 3%, 2%, 1%, 0.8%, 0.5% or 0.1% or essentially 0% by weight of the total chromophore amount leaches out of the biophotonic composition into the wound or tissue during treatment.

The biophotonic compositions suitable for use in the methods of the present disclosure may be selected from any of the embodiments of the biophotonic compositions described herein. For instance, the biophotonic compositions useful in the method of the present disclosure may comprise a first chromophore that undergoes at least partial photobleaching upon application of light. The first chromophore may absorb at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm, 250-350 nm, 300-400 nm, 350-450 nm, 400-500 nm, 450-650 nm, 600-700 nm, 650-750 nm or 700-800 nm. In other examples, suitable biophotonic compositions for the methods of the present disclosure may further comprise at least one additional chromophore (e.g., a second chromophore). The absorption spectrum of the second chromophore overlaps at least about 80%, 50%, 40%, 30%, or 20% with the emission spectrum of the first chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Illumination of the biophotonic composition with light may cause a transfer of energy from the first chromophore to the second chromophore. Subsequently, the second chromophore may emit energy as fluorescence and/or generate reactive oxygen species. In certain embodiments of the methods the present disclosure, energy transfer caused by the application of light is not accompanied by concomitant generation of heat, or does not result in tissue damage.

The biophotonic compositions useful for the present methods comprise a gelling agent. The gelling agent may include, but is not limited to, lipids such as glycerin, glycols such as propylene glycol, hyaluronic acid, glucosamine sulfate, cellulose derivatives (hydroxypropyl methylcellulose, hydroxyethyl cellulose, hydroxypropyl cellulose, methylcellulose and the like), noncellulose polysaccharides (galactomannans, guar gum, carob gum, gum arabic, sterculia gum, agar, alginates and the like) and acrylic acid polymers.

When the method involves a biophotonic composition having at least two chromophores, the first chromophore is present in an amount of about 0.01-40% per weight of the composition, and the second chromophore is present in an amount of about 0.001-40% per weight of the composition.

In certain embodiments, the first chromophore is present in an amount of about 0.01-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the total weight per weight of chromophore or combination of chromophores may be in the amount of about 0.01-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In the methods of the present disclosure, any source of actinic light can be used. Any type of halogen, LED or plasma arc lamp or laser may be suitable. In some instances, the light is a continuous light. In some other instances the light is modulated. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In another embodiment, sunlight may be used. In yet another embodiment, a LED photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. Furthermore, the source of actinic light should have a suitable power density. Suitable power density for non-collimated light sources (LED, halogen or plasma lamps) are in the range from about 1 mW/cm$^2$ to about 200 mW/cm$^2$. Suitable power densities for laser light sources are in the range from about 0.5 mW/cm$^2$ to about 0.8 mW/cm$^2$.

In some embodiments of the methods of the present disclosure, the light has an energy at the subject's skin, wound or mucosa surface of between about 1 mW/cm$^2$ and about 500 mW/cm$^2$, 1-300 mW/cm$^2$, or 1-200 mW/cm$^2$, wherein the energy applied depends at least on the condition being treated, the wavelength of the light, the distance of the subject's skin from the light source, and the thickness of the biophotonic composition. In certain embodiments, the light at the subject's skin is between about 1-40 mW/cm$^2$, or 20-60 mW/cm$^2$, or 40-80 mW/cm$^2$, or 60-100 mW/cm$^2$, or 80-120 mW/cm$^2$, or 100-140 mW/cm$^2$, or 120-160 mW/cm$^2$, or 140-180 mW/cm$^2$, or 160-200 mW/cm$^2$, or 110-240 mW/cm$^2$, or 110-150 mW/cm$^2$, or 190-240 mW/cm$^2$.

In some embodiments, a mobile device can be used to activate embodiments of the biophotonic composition of the present disclosure, wherein the mobile device can emit light having an emission spectra which overlaps an absorption spectra of the chromophore in the biophotonic composition. The mobile device can have a display screen through which the light is emitted and/or the mobile device can emit light from a flashlight which can photoactivate the biophotonic composition.

In some embodiments, a display screen on a television or a computer monitor can be used to activate the biophotonic composition, wherein the display screen can emit light having an emission spectra which overlaps an absorption spectra of a photoactive agent in the photoactivatable composition.

In certain embodiments, the first and/or the second chromophore (when present) can be photoactivated by ambient light which may originate from the sun or other light sources. Ambient light can be considered to be a general illumination that comes from all directions in a room that has no visible source. In certain embodiments, the first and/or the second chromophore (when present) can be photoactivated by light in the visible range of the electromagnetic spectrum. Exposure times to ambient light may be longer than that to direct light.

In certain embodiments, different sources of light can be used to activate the biophotonic compositions, such as a combination of ambient light and direct LED light.

The duration of the exposure to actinic light required will be dependent on the surface of the treated area, the type of lesion, trauma or injury that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In one embodiment, the time of exposure to actinic light of the tissue, skin or wound on which the biophotonic composition has been applied is a period between 1 minute and 5 minutes. In another embodiment, the time of exposure to actinic light of the tissue, skin or wound on which the biophotonic composition has been applied is a period between 1 minute and 5 minutes. In some other embodiments, the biophotonic composition is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 20-30 minutes. In yet another embodiment, the source of actinic light is in continuous motion over the treated area for the appropriate time of exposure. In yet another embodiment, multiple applications of the biophotonic composition and actinic light are performed. In some embodiments, the tissue, skin or wound is exposed to actinic light at least two, three, four, five or six times. In some embodiments, a fresh application of the biophotonic composition is applied before exposure to actinic light.

In the methods of the present disclosure, the biophotonic composition may be optionally removed from the site of treatment following application of light. In certain embodiments, the biophotonic composition is left on the treatment site for more than 30 minutes, more than one hour, more than 2 hours, more than 3 hours. It can be illuminated with ambient light. To prevent drying, the composition can be covered with a transparent or translucent cover such as a polymer film, or an opaque cover which can be removed before illumination.

(5) Wounds and Wound Healing

The biophotonic compositions and methods of the present disclosure may be used to treat non-healing wounds and promote healing or granulation tissue formation. Non-healing wounds that may be treated by the biophotonic compositions and methods of the present disclosure include, for example, those arising from acute wounds, injuries to the skin and subcutaneous tissue initiated in different ways (e.g., pressure ulcers from extended bed rest, wounds induced by trauma, wounds induced by conditions such as periodontitis), and with varying characteristics. In certain embodiments, the present disclosure provides biophotonic compositions and methods for treating and/or promoting the healing of, for example, skin diseases that result in a break of the skin or in a wound, clinically infected wounds, burns, incisions, excisions, lacerations, abrasions, puncture or penetrating wounds, gun-shot wounds, surgical wounds, contusions, hematomas, crushing injuries, sores and ulcers.

Biophotonic compositions and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

In certain other embodiments, the present disclosure provides biophotonic compositions and methods for treating and/or promoting healing, Grade I-IV ulcers. In certain embodiments, the application provides compositions suitable for use with Grade II and Grade III ulcers in particular. Ulcers may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

For example, the present disclosure provides biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, compositions and methods of treating a chronic wound are provided here in, where the chronic wound is characterized by diabetic foot ulcers and/or ulcerations due to neurologic and/or vascular complications of diabetes.

In other examples, the present disclosure provides biophotonic compositions and methods for treating and/or promoting healing of a pressure ulcer. Pressure ulcer includes bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turns red, becomes painful and can become necrotic. If untreated, the skin breaks open and can become infected. An ulcer sore is therefore a skin ulcer that occurs in an area of the skin that is under pressure from e.g. lying in bed, sitting in a wheelchair, and/or wearing a cast for a prolonged period of time. Pressure ulcer can occur when a person is bedridden, unconscious, unable to sense pain, or immobile. Pressure ulcer often occur in boney prominences of the body such as the buttocks area (on the sacrum or iliac crest), or on the heels of foot.

Wound healing in adult tissues is a complicated reparative process. For example, the healing process for skin involves the recruitment of a variety of specialized cells to the site of the wound, extracellular matrix and basement membrane deposition, angiogenesis, selective protease activity and re-epithelialization.

There are four overlapping phases in the normal wound healing process. First, in the hemostasis and inflammatory phases, which typically occur from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

In the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

In the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote the wound healing by promoting the formation of substantially uniform epithelialization; promoting collagen synthesis; promoting controlled contraction; and/or by reducing the formation of scar tissue. In certain embodiments, the biophotonic compositions and methods of the present disclosure may promote wound healing by promoting the formation of substantially uniform epithelialization. In some embodiments, the biophotonic compositions and methods of the present disclosure promote collagen synthesis. In some other embodiments, the biophotonic compositions and methods of the present disclosure promote controlled contraction. In certain embodiments, the biophotonic compositions and methods of the present disclosure promote wound healing, for example, by reducing the formation of scar tissue or by speeding up the wound closure process. In certain embodiments, the biophotonic compositions and methods of the present disclosure promote wound healing, for example, by reducing inflammation. In certain embodiments, the biophotonic composition can be used following wound closure to optimize scar revision. In this case, the biophotonic composition may be applied at regular intervals such as once a week, or at an interval deemed appropriate by the physician or by other health care providers.

The biophotonic composition may be soaked into a woven or non-woven material or a sponge and applied as a wound dressing. A light source, such as LEDs or waveguides, may be provided within or adjacent the wound dressing or the composition to illuminate the composition. The waveguides can be optical fibres which can transmit light, not only from their ends, but also from their body. For example, the waveguides may be made of polycarbonate or polymethylmethacrylate.

Adjunct therapies which may be topical or systemic such as antibiotic treatment may also be used. Negative pressure assisted wound closure can also be used to assist wound closure and/or to remove the composition.

(6) Kits

The present disclosure also provides kits for preparing and/or applying any of the compositions of the present disclosure. The kit may include a biophotonic topical composition, as defined above, together with one or more of a light source, devices for applying or removing the composition, instructions of use for the composition and/or light source. In some embodiments, the composition comprises at least a first chromophore in a gelling agent. The chromophore may be present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In embodiments where the composition comprises more than one chromophore, the first chromophore may be present in an amount of about 0.01-40% per weight of the composition, and a second chromophore may be present in an amount of about 0.0001-40% per weight of the composition. In certain embodiments, the first chromophore is present in an amount of about 0.01-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the amount of chromophore or combination of chromophores may be in the amount of about 0.05-40.05% per weight of the composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-

27.5%, 25-30%, 27.5-32.5%, 30-35%, 32.5-37.5%, or 35-40.05% per weight of the composition. The composition may include an oxygen-releasing agent present in amount about 0.01%-40%, 0.01%-1.0%, 0.5%-10.0%, 5%-15%, 10%-20%, 15%-25%, 20%-30%, 15.0%-25%, 20%-30%, 25%-35%, or 30%-40% by weight to weight of the composition. Alternatively, the kit may include the oxygen-releasing agent as a separate component to the chromophore containing composition.

In some embodiments, the kit includes more than one composition, for example, a first and a second composition. The first composition may include the oxygen-releasing agent and the second composition may include the first chromophore in the gelling agent. The first chromophore may have an emission wavelength between about 400 nm and about 570 nm. The oxygen-releasing agent may be present in the first composition in an amount of about 0.01%-1.0%, 0.5%-10.0%, 5%-15%, 10%-20%, 15%-25%, 20%-30%, 15.0%-25%, 20%-30%, 25%-35%, 30%-40% or 35%-45% by weight to weight of the first composition. The chromophore may be present in the second composition in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In embodiments where the second composition comprises more than one chromophore, the first chromophore may be present in an amount of about 0.01-40% per weight of the second composition, and a second chromophore may be present in an amount of about 0.0001-40% per weight of the second composition. In certain embodiments, the first chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In certain embodiments, the amount of chromophore or combination of chromophores may be in the amount of about 0.05-40.05% per weight of the second composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the second chromophore.

In some other embodiments, the first composition may comprise the first chromophore in a liquid or as a powder, and the second composition may comprise a gelling composition for thickening the first composition. The oxygen-releasing agent may be contained in the second composition or in a third composition in the kit. In some embodiments, the kit includes containers comprising the compositions of the present disclosure. In some embodiments, the kit includes a first container comprising a first composition that includes the oxygen-releasing agent, and a second container comprising a second composition that includes at least one chromophore. The containers may be light impermeable, air-tight and/or leak resistant. Exemplary containers include, but are not limited to, syringes, vials, or pouches. The first and second compositions may be included within the same container but separated from one another until a user mixes the compositions. For example, the container may be a dual-chamber syringe where the contents of the chambers mix on expulsion of the compositions from the chambers. In another example, the pouch may include two chambers separated by a frangible membrane. In another example, one component may be contained in a syringe and injectable into a container comprising the second component.

The biophotonic composition may also be provided in a container comprising one or more chambers for holding one or more components of the biophotonic composition, and an outlet in communication with the one or more chambers for discharging the biophotonic composition from the container. In one embodiment, discharging the biophotonic compositions causes the components of the composition to mix to form a biophotonic composition wherein less than 15% by weight of the total chromophore amount leaches out of the biophotonic composition in use In other embodiments, the kit comprises a systemic or topical drug for augmenting the treatment of the composition. For example, the kit may include a systemic or topical antibiotic or hormone treatment for acne treatment or wound healing.

Written instructions on how to use the biophotonic composition in accordance with the present disclosure may be included in the kit, or may be included on or associated with the containers comprising the compositions of the present disclosure.

In certain embodiments, the kit may comprise a further component which is a dressing. The dressing may be a porous or semi-porous structure for receiving the biophotonic composition. The dressing may comprise woven or non-woven fibrous materials.

In certain embodiments of the kit, the kit may further comprise a light source such as a portable light with a wavelength appropriate to activate the chromophore in the biophotonic composition. The portable light may be battery operated or re-chargeable.

In certain embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

Example 1

Figure 5A:
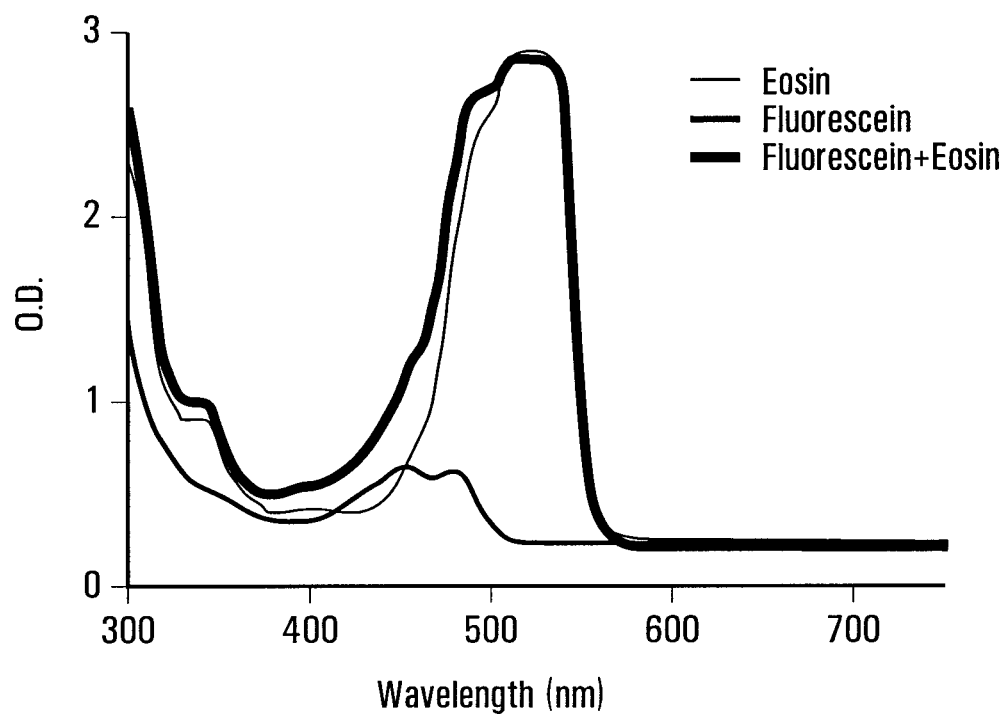
FIGS. 5A and 5B illustrate graphs showing absorbance and emission spectra, respectively, of a biophotonic composition according to certain embodiments of the present disclosure which includes Eosin and Fluorescein in a gel.
Figure 5B:
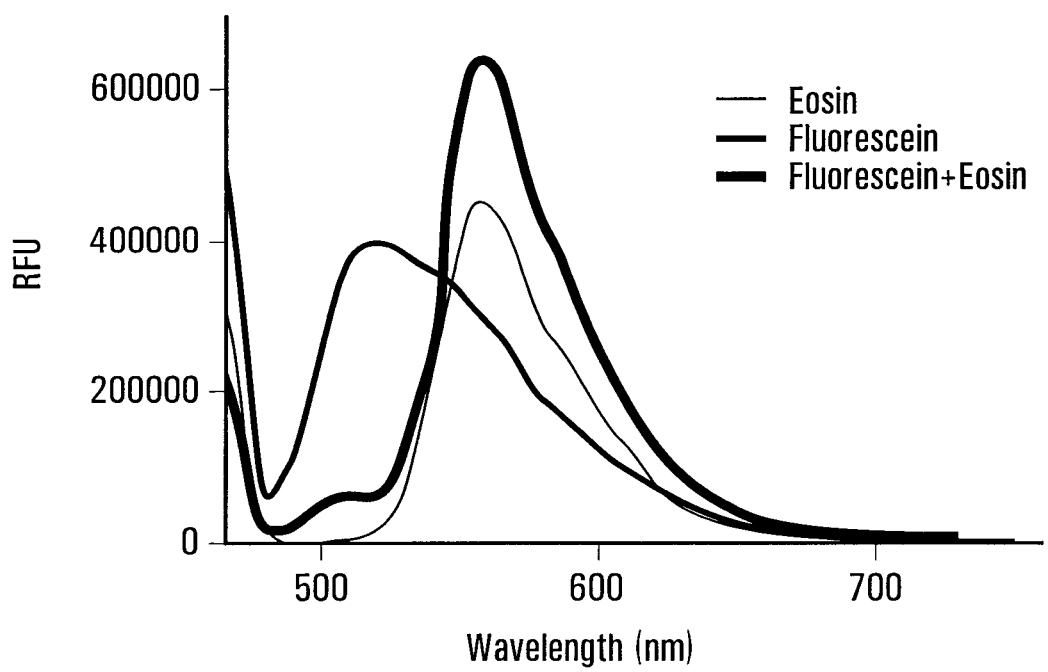

The photodynamic properties of (i) Fluorescein sodium salt at about 0.09 mg/mL, (ii) Eosin Y at about 0.305 mg/mL, and (iii) a mixture of Fluorescein sodium salt at about 0.09 mg/mL and Eosin Y at about 0.305 mg/mL in a gel according to an embodiment of the present disclosure (comprising about 12% carbamide peroxide), were evaluated. A flexstation 384 II spectrometer was used with the following parameters: mode fluorescence, excitation 460 nm, emission spectra 465-750 nm. The absorption and emission spectra are shown in FIGS. 5A and 5B which indicate an energy transfer between the chromophores in the combination.

Example 2

Figure 6A:
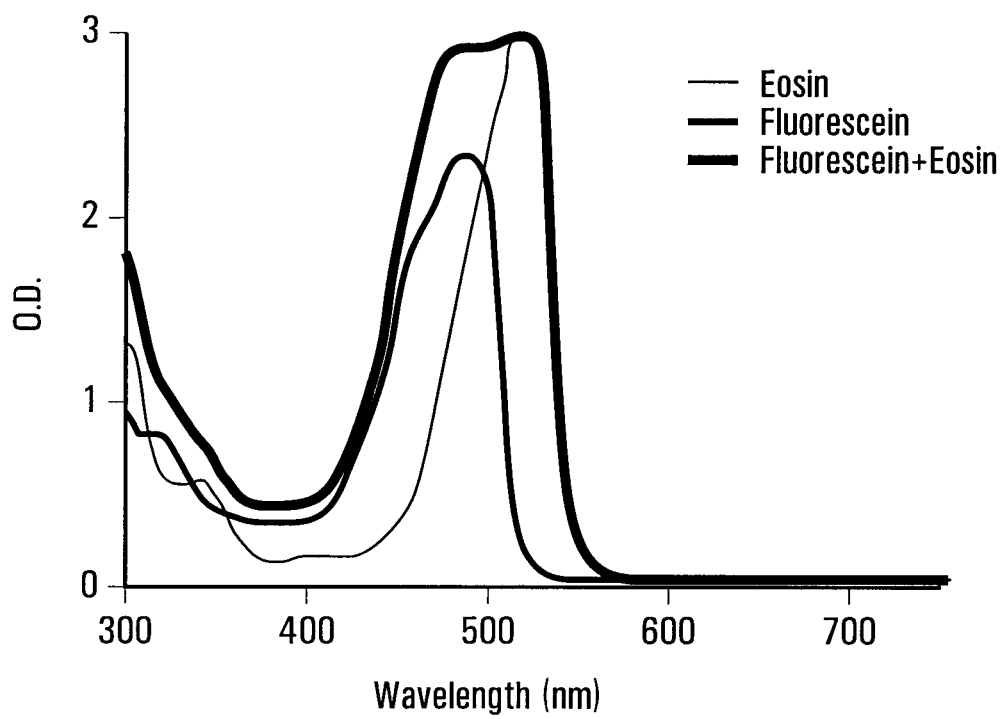
FIGS. 6A and 6B illustrate graphs showing absorbance and emission spectra, respectively, of a biophotonic composition according to certain embodiments of the present disclosure which includes Eosin and Fluorescein in an aqueous solution.
Figure 6B:
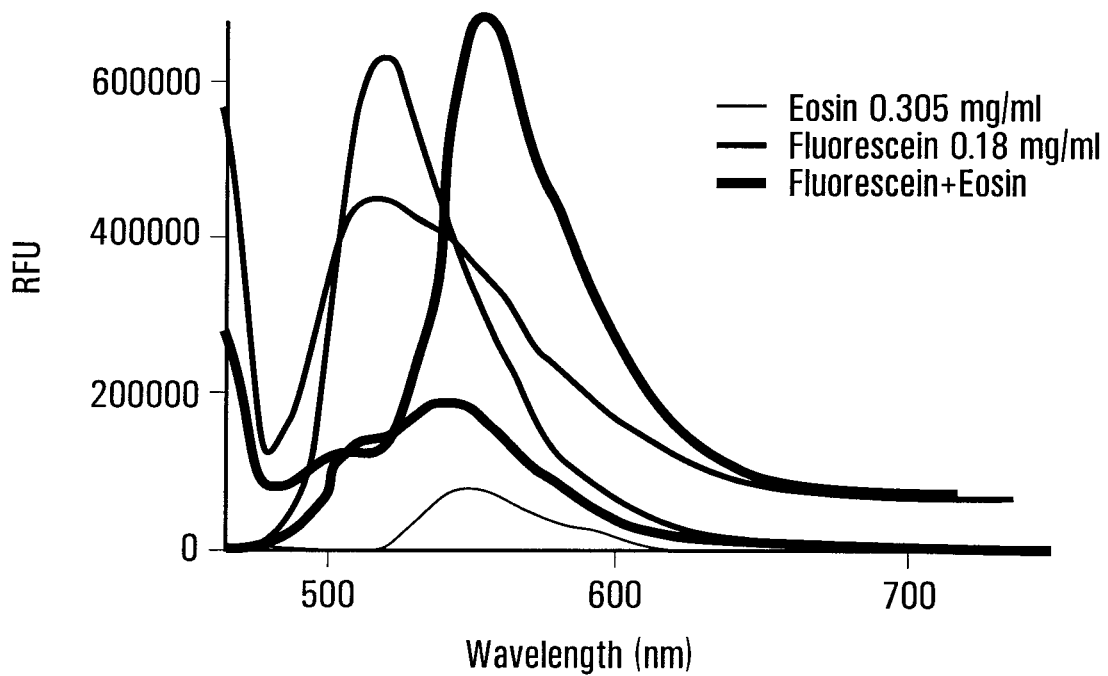

The photodynamic properties of (i) Fluorescein sodium salt at 0.18 mg/mL final concentration, (ii) Eosin Y at about 0.305 mg/mL, and (iii) a mixture of Fluorescein sodium salt at about 0.18 mg/mL and Eosin Y at about 0.305 mg/mL in an aqueous solution were evaluated. A flexstation 384 II spectrometer was used with the following parameters: mode fluorescence, excitation 460 nm, emission spectra 465-750 nm. The absorption and emission spectra are shown in FIGS. 6A and 6B which indicate an energy transfer between the chromophores in the combination.

Example 3

Figure 7A:
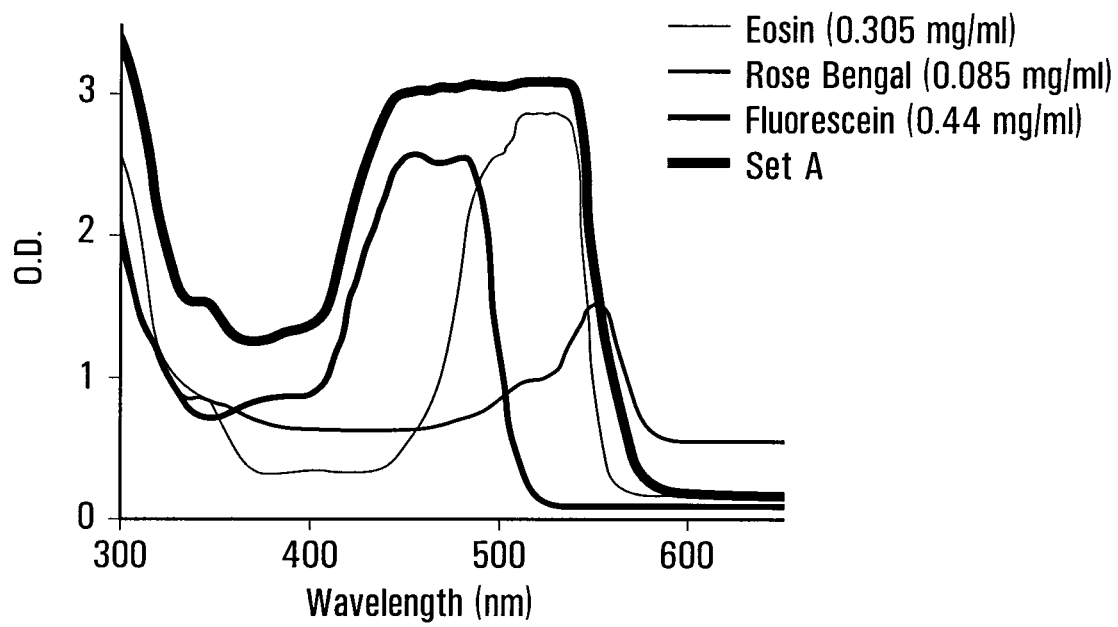
FIGS. 7A and 7B illustrate graphs showing the absorbance and emission spectra, respectively, of a biophotonic composition according to certain embodiments of the present disclosure which includes Eosin, Fluorescein and Rose Bengal in a gel.
Figure 7B:
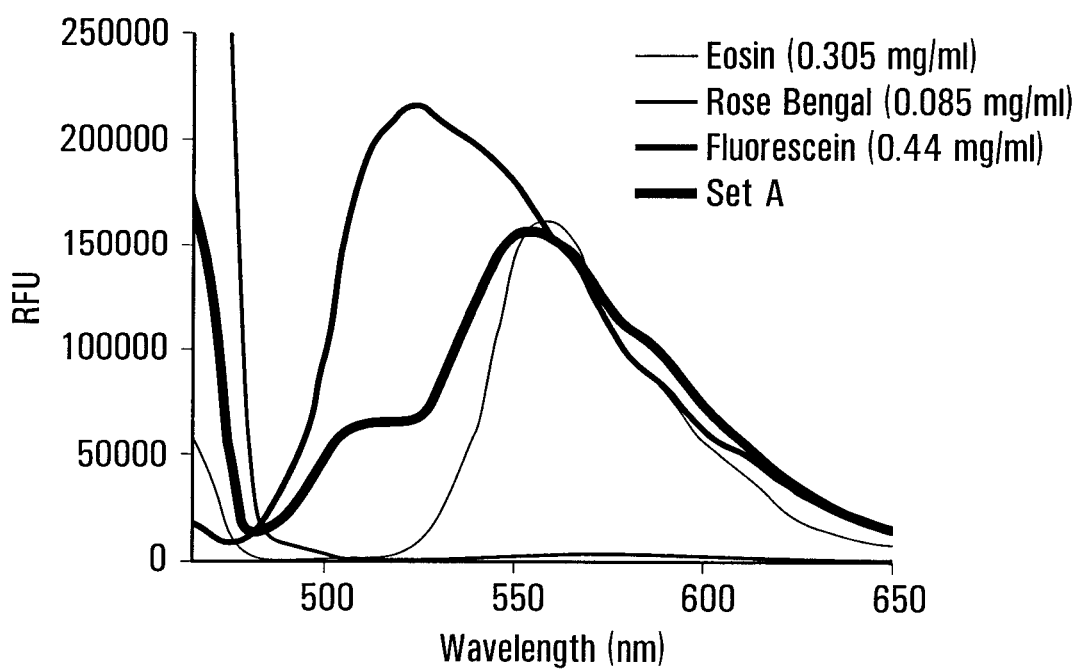

The photodynamic properties of (i) Rose Bengal at about 0.085 mg/mL, (ii) Fluorescein sodium salt at about 0.44 mg/mL final concentration, (iii) Eosin Y at about 0.305 mg/mL, and (iv) a mixture of (i), (ii) and (iii) in a gel comprising about 12% carbamide peroxide (Set A), according to an embodiment of the invention, were evaluated. A flexstation 384 II spectrometer was used with the following parameters: mode fluorescence, excitation 460 nm, emission spectra 465-750 nm. The absorbance and emission spectra are shown in FIGS. 7A and 7B which indicate an energy transfer between the chromophores in the chromophore combination.

Example 4

Figure 8A:
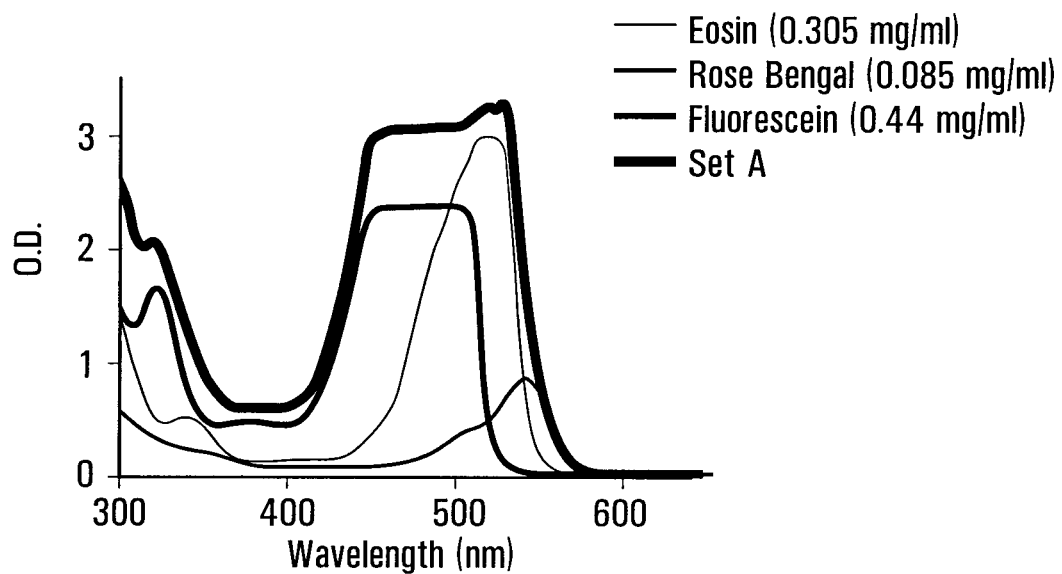
FIGS. 8A and 8B illustrate graphs showing absorbance and emission spectra, respectively, of a biophotonic composition according to certain embodiments of the present disclosure which includes Eosin, Fluorescein and Rose Bengal in an aqueous solution.
Figure 8B:
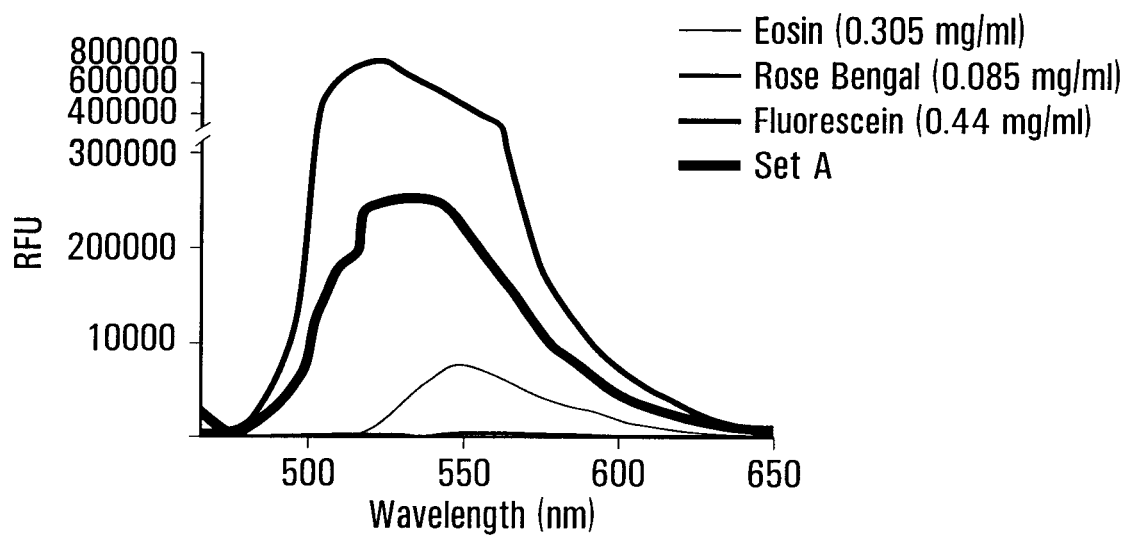

The photodynamic properties of (i) Rose Bengal at about 0.085 mg/mL, (ii) Fluorescein sodium salt at about 0.44 mg/mL final concentration, (iii) Eosin Y at about 0.305 mg/mL, and (iv) a mixture of (i), (ii) and (iii) in an aqueous solution (Set A), were evaluated. A flexstation 384 II spectrometer was used with the following parameters: mode fluorescence, excitation 460 nm, emission spectra 465-750 nm. The absorbance and emission spectra are shown in FIGS. 8A and 8B which indicate an energy transfer between the chromophores in the chromophore combination, in the absence of an oxygen-releasing agent.

Energy transfer was also seen between: Eosin Y and Rose Bengal; Phloxine B and Eosin Y; Phloxine B, Eosin Y and Fluorescein, amongst other combinations. It is to be reasonably inferred that energy transfer can also occur in biophotonic compositions of the present disclosure.

Example 5—Leaching Test Using Polycarbonate Membrane

FIG. 4 depicts an experimental setup of an in vitro release test for evaluating leaching of the chromophore(s) or other components (e.g., oxygen releasing agents) from the biophotonic compositions of the present disclosure. In this in vitro test, a 2 mm thick layer of the biophotonic composition is applied on an upper surface of a circular polycarbonate (PC) membrane with a diameter of 2.4 to 3 cm, a thickness of 10 microns, and a pore size of 3 microns. The underside of the membrane is in direct contact with phosphate saline buffer (PBS) contained in a closed compartment (i.e., the receptor compartment). Samples (100 μl×2) are then taken from the receptor compartment at different time points (e.g., at 5, 10, 20, and 30 min), and evaluated for concentration of the chromophore(s) or any other components of the biophotonic composition using spectrophotometry or any other suitable method.

For example, when the chromophore being tested is eosin, a wavelength of about 517 nm (absorbance) may be used. The concentration of the chromophore may then be calculated based on the chromophore standards of known concentration prepared in PBS and measured at the same time. The presence of peroxide (i.e., an indicator of the oxygen releasing agents) can also be assessed using peroxide test sticks (e.g. Quantofix Peroxide 25, Sigma Aldrich).

Table 1 summarizes leaching data for different biophotonic compositions according to the present disclosure. All compositions were spreadable, translucent gels, having a viscosity of about 10,000-80,000 cP. The amount of hydrogen peroxide found in the receptor compartment was low for all compositions containing peroxide in Table 1. The detection method of chromophore by spectrophotometry can measure the chromophore concentration from 0.2 μg/ml. For all biophotonic compositions tested, the release of chromophores increased over time. For all compositions, there was less than 15% by weight of the total chromophore amount that leached after 5 minutes, 10 minutes, 15 minutes, and 25 minutes of incubation (simply by way of example, for a composition comprising 100 mg of chromophores, 15% leaching would indicate that 15 mg of the chromophores have leached out of the composition (i.e., is no longer in the composition)). All tested compositions, other than Eosin Y (0.2%) in a carbopol polymer gel including urea peroxide had less than 15% chromophore leaching even after 30 minutes incubation, which is longer than a treatment time according to some embodiments of the present disclosure.

The effect of illumination on chromophore leaching from the biophotonic compositions was also investigated. It was found that illumination of the biophotonic compositions with light for 5 minutes at a distance of 5 cm induced photobleaching of the chromophore(s). In fact, the chromophores photobleached in about 2-3 minutes. In these cases, the chromophore(s) were undetectable in the receptor compartment. Therefore, during treatment involving light illumination, even lower chromophore leaching than the results presented in Table 1 can be reasonably expected.

TABLE 1

Percentage of chromophores released from biophotonic compositions according to embodiments of the present disclosure, with time of incubation.

| Composition | Percentage chromophore released into receptor compartment from composition with time of incubation (n = 3) | | | |
| --- | --- | --- | --- | --- |
| | 5 mins | 10 mins | 20 mins | 30 mins |
| Eosin Y (0.011%), carbopol gel (1.7%), urea peroxide gel (12%), saffron, glycerine, propylene glycol, hyaluronic acid. | Not detectable | Not detectable | 0.75 | 0.78 |
| Fluorescein (0.2%), carbopol gel (1.7%), urea peroxide (12%), saffron, glycerine, propylene glycol, hyaluronic acid. | 2.71 | 4.85 | 4.72 | 4.84 |

TABLE 1-continued

Percentage of chromophores released from biophotonic compositions according to embodiments of the present disclosure, with time of incubation.

| Composition | Percentage chromophore released into receptor compartment from composition with time of incubation (n = 3) | | | |
| --- | --- | --- | --- | --- |
| | 5 mins | 10 mins | 20 mins | 30 mins |
| Rose Bengal (0.2%), carbopol gel (1.7%), urea peroxide (12%), saffron, glycerine, propylene glycol, hyaluronic acid. | 2.39 | 3.32 | 5.26 | 5.21 |
| Rose Bengal (0.1%) + Fluorescein (0.1%), carbopol gel (1.7%), urea peroxide gel (12%), saffron, glycerine, propylene glycol, hyaluronic acid. | 2.91 | 5.21 | 8.48 | 8.43 |
| Phloxin B (0.2%), carbopol gel (1.7%), urea peroxide gel (12%), saffron, glycerine, propylene glycol, hyaluronic acid. | 0.54 | 2.39 | 4.62 | 4.50 |
| Eosin Y (0.2%), carbopol gel (1.7%), urea peroxide gel (12%), saffron, glycerine, propylene glycol, hyaluronic acid. | 2.77 | 2.72 | 6.56 | 9.08 |
| Phloxin B (0.1%) + Fluorescein (0.1%), carbopol gel (1.7%), urea peroxide gel (12%), saffron, glycerine, propylene glycol, hyaluronic acid. | 2.28 | 4.49 | 7.56 | 11.02 |
| Phloxin B (0.1%) + Rose Bengal (0.1%), carbopol gel (1.7%), urea peroxide gel (12%), saffron, glycerine, propylene glycol, hyaluronic acid. | 2.41 | 2.36 | 5.14 | 4.90 |
| Phloxin B (0.1%) + Eosin Y (0.1%) carbopol gel (1.7%), urea peroxide (12%), saffron, glycerine, propylene glycol, hyaluronic acid. | 3.84 | 6.25 | 10.08 | 12.00 |
| Rose Bengal (0.1%) + Eosin Y (0.1%), carbopol gel (1.7%), urea peroxide (12%), saffron, glycerine, propylene glycol, hyaluronic acid. | 3.04 | 4.28 | 6.63 | 8.12 |
| Fluorescein (0.1%) + Eosin Y (0.1%), carbopol gel (1.7%), urea peroxide (12%), saffron, glycerine, propylene glycol, hyaluronic acid. | 2.96 | 3.99 | 5.78 | 7.58 |
| Phloxin B (0.1%) + Eosin Y (0.1%), carbopol gel (1.7%) | 1.00 | 2.3 | 4.48 | 5.80 |
| Eosin Y (0.2%), carbopol gel (1.7%), saffron, glycerine, propylene glycol | 3.34 | 4.90 | 7.30 | 9.26 |
| Phloxin B (0.1%) + Eosin Y (0.1%), gelatin gel (5%) | 0.51 | 0.25 | 1.79 | 3.14 |
| Rose Bengal (0.1%) + Eosin Y (0.1%), gelatin gel (5%) | 0 | 0.39 | 1.39 | 2.15 |
| Eosin Y (0.2%), starch gel (8%) | 2.91 | 3.72 | 7.11 | 9.06 |
| Eosin Y (0.2%), sodium hyaluronate gel (2%) | 3.41 | 6.24 | 9.93 | 12.77 |

Example 6—Angiogenic Potential of the Biophotonic Composition of the Disclosure

Figure 9:
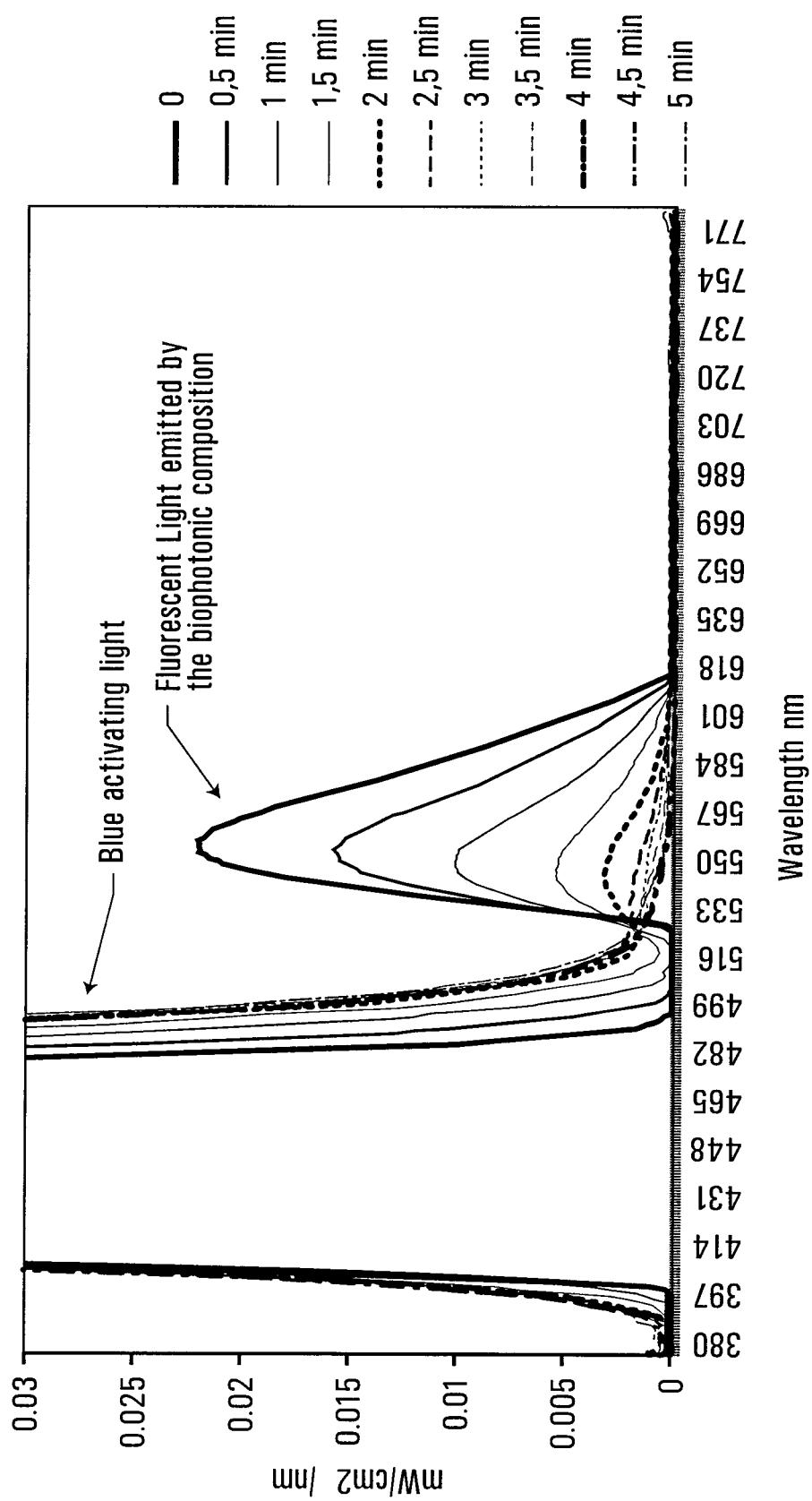
FIG. 9 illustrate a graph showing the emission spectrum of the intensity over time of the light being emitted from a biophotonic composition according to certain embodiments of the present disclosure.

A human skin model was developed to assess the angiogenic potential of the biophotonic composition of the present disclosure. Briefly, a biophotonic composition comprising fluorophores (Eosin Y and Erythrosine) in a carbomer polymer-based gel including urea peroxide, was placed on top of a human skin model containing fibroblasts and keratinocytes. The spreadable and translucent biophotonic composition had less than 15% by weight of the total chromophore amount leaching out of the biophotonic composition for up to 30 minutes, when tested separately according to Example 5. The skin model and the composition were separated by a nylon mesh of 20 micron pore size. The composition was then irradiated with blue light ('activating light') for 5 minutes at a distance of 5 cm from the light source. The activating light consisted of light emitted from an LED lamp having an average peak wavelength of about 400-470 nm, and a power intensity measured at 10 cm of 7.7 J/cm$^2$ to 11.5 J/cm$^2$. Upon illumination with the activating light, the biophotonic composition emitted fluorescent light (FIG. 9). Since the biophotonic composition was in limited contact with the cells, the fibroblasts and keratinocytes were exposed mainly to the activating light and the fluorescent light emitted from the biophotonic composition. Conditioned media from the treated human 3D skin model were then applied to human aortic endothelial cells previously plated in matrigel. The formation of tubes by endothelial cells was observed and monitored by microscopy after 24 hours. The conditioned medium from 3D skin models treated with light illumination induced endothelial tube formation in vitro, suggesting an indirect effect of the light treatment (blue light and fluorescence) on angiogenesis via the production of factors by fibroblasts and keratinocytes. Plain medium and conditioned medium from untreated skin samples were used as a control, and did not induce endothelial tube formation. FIG. 9 is an emission spectrum showing the intensity over time of the light being emitted from the biophotonic composition.

Example 7—Protein Secretion and Gene Expression Profiles

Wounded and unwounded 3D human skin models (EpiDermFT, MatTek Corporation) were used to assess the potential of a biophotonic composition of the present disclosure to trigger distinct protein secretion and gene expression profiles. Briefly, a biophotonic composition comprising Eosin and Erythrosine in a carbomer polymer-based gel including urea peroxide, was placed on top of wounded and unwounded 3D human skin models cultured under different conditions [with growth factors (Medium 1×), 50% growth factors (Medium 0.5×) and no growth factors (Medium 0×)]. The spreadable and translucent biophotonic gel had less than 15% leaching of chromophore during a 30 minute test time, according to Example 6. The skin models and the composition were separated by a nylon mesh of 20 micron pore size. Each skin model-composition combination was then irradiated with blue light ('activating light') for 5 minutes at a distance of 5 cm from the light source. The activating light consisted of light emitted from an LED lamp having an average peak wavelength of about 440-470 nm, a power density of 60-150 mW/cm$^2$ at 5 cm, and a total intensity after 5 minutes of about 18-39 J/cm$^2$. The controls consisted of 3D skin models not illuminated with light.

Figure 10:
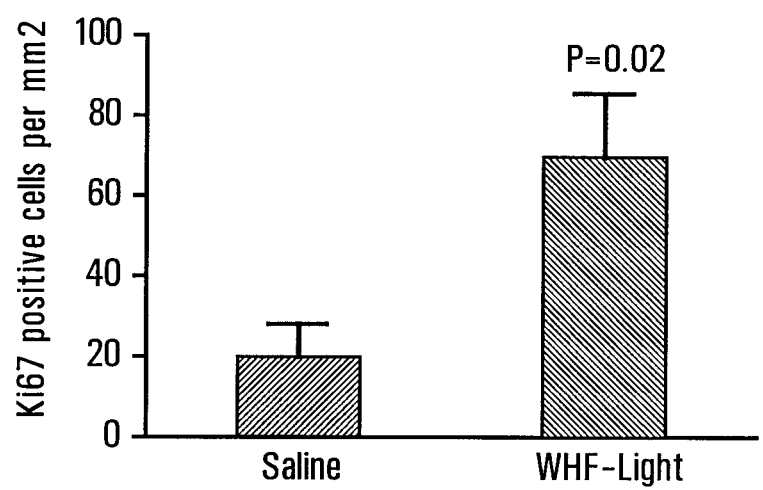
FIG. 10 illustrates a graph showing the effect of a biophotonic composition according to certain embodiments of the present disclosure on Ki67 expression.

Gene expression and protein secretion profiles were measured 24 hours post-light exposure. Cytokine secretion was analyzed by antibody arrays (RayBio Human Cytokine antibody array), gene expression was analyzed by PCR array (PAHS-013A, SABioscience) and cytotoxicity was determined by GAPDH and LDH release. Results (Tables 2 and 3) showed that the light treatment increases the level of protein secreted and gene expression involved in the early inflammatory phase of wound healing in wounded skin inserts and in non-starvation conditions. In starvation conditions mimicking chronic wounds, there was no increase in the level of inflammatory protein secreted when compared to the control. Interestingly, the effect of the light treatment on unwounded skin models has a much lower impact at the cellular level than on wounded skin insert, which suggests an effect at the cellular effect level of the light treatment. It seems to accelerate the inflammatory phase of the wound healing process. Due to the lack of other cell types such as macrophages in the 3D skin model, the anti-inflammatory feed-back is absent and may explain the delay in wound closure. Cytotoxicity was not observed in the light treatments.

underlying tissues. Following flap closure, a biophotonic gel according to an embodiment of the present disclosure was applied onto the dorsal flap in a thin monolayer (2 mm) and exposed to a light, for 5 minutes, from a LED light source having a peak wavelength of about 440-470 nm. The spreadable biophotonic gel included a fluorophore in a carbopol gel and urea peroxide, the gel having a viscosity of about 10,000 cP to 50,000 cP, and demonstrating less than 15% leaching when tested for up to 30 minutes according to Example 5. The biophotonic gel was removed and skin specimens were collected from different areas in the flap for histological analyses nine days post-treatment. The treated group demonstrated a significantly greater number of Ki67-positive-staining events (P=0.02) compared to those in the non-treated group these results, suggesting that the treatment may modulate the proliferation of the cells involved in wound healing (FIG. 10). Following examination by an external pathologist, the treatment group was associated with a significant (P<0.05) decrease in the coagulative necrosis in the epidermis and an increase of the fibrillar stroma (dermis) as compared to the control group.

Example 9—Evaluation of Removal of Biophotonic Composition from Ethanol Soaked Paper Regular white print paper was soaked in 70% ethanol (EtOH). A 2 mm thickness of different embodiment's of biophotonic compositions according to the present disclosure (Table 4) were placed onto the soaked paper and left for 5 minutes. After 5 minutes, the compositions were washed off with 70% EtOH. A composition comprising Eosin (0.017%), silica particles, modified starch, and hydrogen peroxide was also tested.

The results show that biophotonic compositions of the present disclosure including a carbamide gel do not stain

TABLE 2

List of proteins with statistically significant difference secretion ratio between treated and untreated control at day 3. Two arrows mean that the ratio was over 2 folds.

| | Medium 1X | Medium 0.5X | | Medium 0X | |
|---|---|---|---|---|---|
| Increase | | ENA78 p = 0.04 | ↑↑ | Angiogenin p = 0.03 | ↑ |
| | | Il-1R4/ST2 p = 0.02 | ↑↑ | CXCL16 p = 0.04 | ↑ |
| | | MMP3 p = 0.01 | ↑↑ | | |
| | | MCP-2 p = 0.04 | ↑↑ | | |
| Decrease | BMP6 p = 0.01 ↓ | BMP6 p = 0.02 | ↓ | | |
| | TNFα p = 0.005 ↓ | | | | |

TABLE 3

List of genes with statistically significant difference expression ratio between treated and untreated control during the first 24 hours. Two arrows mean that the ratio was over 2 folds.

| | Medium 1X | | Medium 0.5X | | Medium 0X | |
|---|---|---|---|---|---|---|
| Increase | CTGF p = 0.02 | ↑ | CTGF P = 0.04 | ↑ | MMP3 p = 0.007 | ↑↑ |
| | ITGB3 p = 0.03 | ↑ | ITGB3 p = 0.05 | ↑ | LAMA1 p = 0.03 | ↑ |
| | MMP1 p = 0.03 | ↑ | MMP1 p = 0.02 | ↑↑ | ITGA2 p = 0.03 | ↑ |
| | MMP3 p = 0.01 | ↑ | MMP10 p = 0.003 | ↑↑ | | |
| | THBS1 P = 0.02 | ↑ | MMP3 p = 0.007 | ↑↑ | | |
| | | | MMP8 p = 0.02 | ↑↑ | | |
| | | | THBS1 p = 0.03 | ↑ | | |
| Decrease | HAS1 p = 0.009 | ↓↓ | NCAM1 p = 0.02 | ↓↓ | | |
| | NCAM1 p = 0.05 | ↓↓ | VCAN p = 0.02 | ↓ | | |
| | VCAM1 p = 0.03 | ↓↓ | LAMC1 p = 0.002 | ↓ | | |
| | COL7A1 p = 0.04 | ↓ | COL6A1 p = 0.007 | ↓ | | |
| | CTNNA1 p = 0.03 | ↓ | MMP7 p = 0.003 | ↓ | | |

Example 8—Flap Closure

A caudally based rectangular flap was elevated in the back of Wistar rats. A silicone sheet was inserted beneath the skin flap to prevent adhesion and reperfusion of the flap from the white paper. A composition containing Eosin and another hydrophilic polymer (starch) in combination with silica particles did stain the paper.

TABLE 4

Evaluation of removal of biophotonic composition from paper

| Biophotonic composition | Colour of paper after washing |
|---|---|
| Eosin (0.017%), silica particles, modified starch, hydrogen peroxide (included for comparison only). | Orange/red stain on paper observed. |
| Eosin (0.011%) in a urea peroxide, glycerin, propylene glycol, carbopol, hyaluronic acid, glucosamine gel. | Substantially white - no staining observed. |
| Eosin (0.011%) + carbamide peroxide + 1.8% carbopol 940 | Substantially white - no staining observed. |

Example 10—Evaluation of Heat Dissipation During Illumination of a Biophotonic Composition A 3 mm thick layer of a biophotonic composition according to an embodiment of the present disclosure comprising a fluorescent chromophore in a carbopol gel according to an embodiment of the present disclosure was applied on the skin of hands of volunteers with different skin types and illuminated for 5 minutes with a blue LED light having a power density of about 50 to 150 mW/cm$^2$ at a distance of 5 cm from the light. The biophotonic gel was spreadable and had less than 15% by weight of the of the total chromophore amount leaching out of the biophotonic composition when tested according to Example 6. A thermometer probe was placed within the composition, at the surface of the skin, and the temperature was monitored in real-time during illumination of the composition. The skin temperature with no composition but the same light illumination was also measured for the same volunteers. The skin types tested were, according to Fitzpatrick classification scales, type III (white skin, sometimes burns and gradually tans), type IV (beige to brown skin, rarely burns and easily tans) and type VI (black skin, never burns, easily tans). The results are shown in Table 5.

TABLE 5

Temperature of skin under biophotonic composition during illumination for 5 minutes compared to temperature skin with no composition and illumination alone

| | Minimum-maximum temperature of skin under composition during 5 mins of illumination/° C. (Average over 5 mins/° C.) | Minimum-maximum temperature of skin without composition during 5 mins. of illumination/° C. (Average over 5 mins/° C.) |
|---|---|---|
| Skin Type III | 26.5-35.1 (32.2) | 28.7-39.1 (36.2) |
| Skin Type IV | 27.6-39.9 (36.1) | 31.4-39.9 (37.0) |
| Skin Type VI | 28.5-39.9 (35.6) | 29.6-40.0 (37.4) |

All skin types with biophotonic composition applied demonstrated a slower temperature increase compared to bare skin (no biophotonic composition), and so the biophotonic composition conferred a buffer effect. After 5 minutes of light illumination, the temperature of the skin under the biophotonic composition for all volunteers reached a maximum of 39.9° C., compared to 40° C. with light alone and bare skin. Overall no pain, burning or discomfort was felt by the volunteers.

Figure 11A:
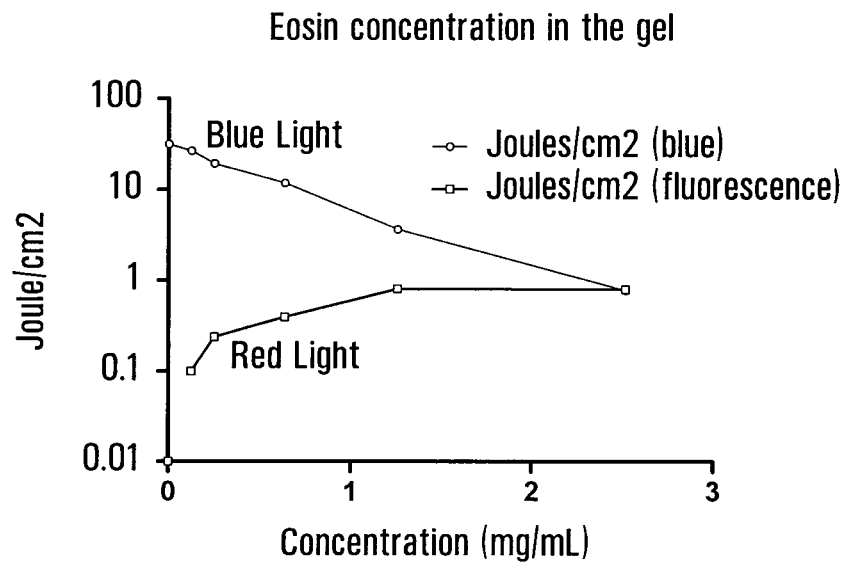
FIGS. 11A and 11B illustrate a graph showing that emitted fluorescence from chromophore in a biophotonic composition according to certain aspects of the present disclosure increases rapidly with increasing concentration but slows down to a plateau with further concentration increase for Eosin Y (11A) and Fluorescein (11B).
Figure 11B:
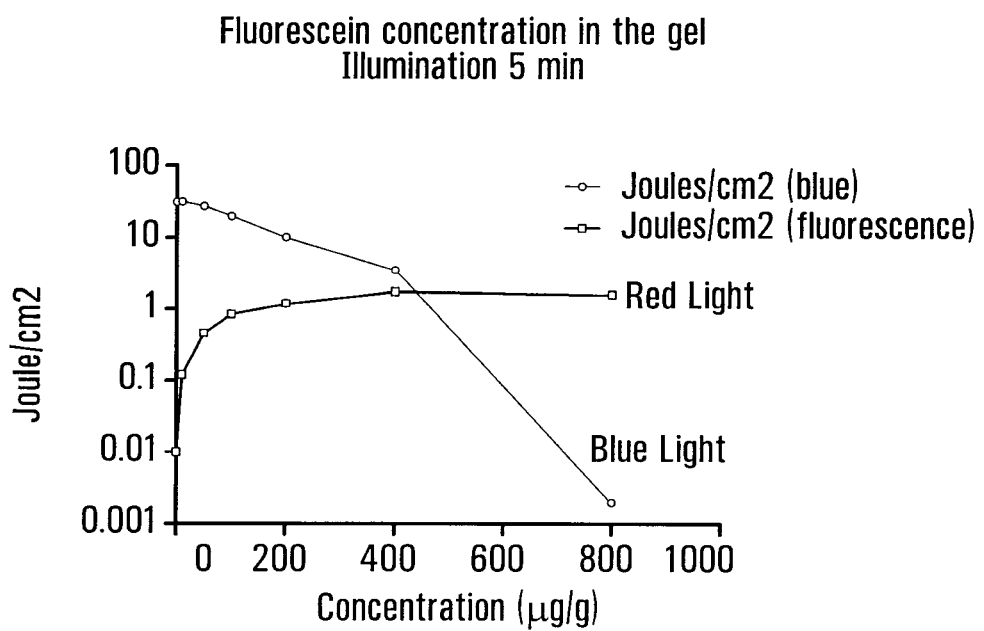

Example 11—Selecting the Concentration of Chromophore in the Biophotonic Composition The fluorescence spectra of biophotonic compositions with different concentrations of chromophores were investigated using a spectrophotometer and an activating blue light. Exemplary fluorescence spectra of Eosin Y and Fluorescein are presented in FIGS. 11A and 11B, respectively. It was found that emitted fluorescence from the chromophore increases rapidly with increasing concentration but slows down to a plateau with further concentration increase. Activating light passing through the composition decreases with increasing chromophore composition as more is absorbed by the chromophores. Therefore, the concentration of chromophores in biophotonic compositions of the present disclosure can be selected according to a required ratio and level of activating light and fluorescence treating the tissue based on this example. In some embodiments, it will be after the zone of rapid increase, i.e. between 0.5 and 1 mg/mL for Eosin Y (FIG. 11A).

Therefore, concentration can be selected according to required activating light and fluorescence. In some embodiments, it will be after the zone of rapid increase, i.e. between about 0.5 and about 1 mg/mL for Eosin Y (FIG. 11A). A person skilled in the art would also take into account the effect on fluorescence of other ingredients in a composition and adapt the concentration of the chromophore accordingly. For example, certain gelling agents bind to certain chromophores which may lower their fluorescence. One example is albumin. In such cases, a higher concentration of the chromophore can be used in the composition.

Example 12—Eosin and Rose Bengal Act in a Synergistic Manner

The synergy between two chromophores according to various embodiments of the present disclosure was investigated by preparing the following:
1—Eosin Y (0.035%)+Rose Bengal (0.085%) in a 12% carbamide gel
2—Rose Bengal (0.085%) in a 12% carbamide gel Rose Bengal is known to have a high quantum yield in terms of oxygen production in the presence of oxygen-releasing agents when photoactivated by green light. Eosin Y is known to have a high quantum yield in terms of emitted fluorescent light when photoactivated and can be at least partially activated by blue light when in a gel. Photoactivated Eosin Y does not have a high quantum yield in terms of oxygen production in the presence of oxygen-releasing agents. When Eosin Y and Rose Bengal are combined, it appears that both chromophores are activated by the same blue light as evidenced by FIG. 12.

Figure 12:
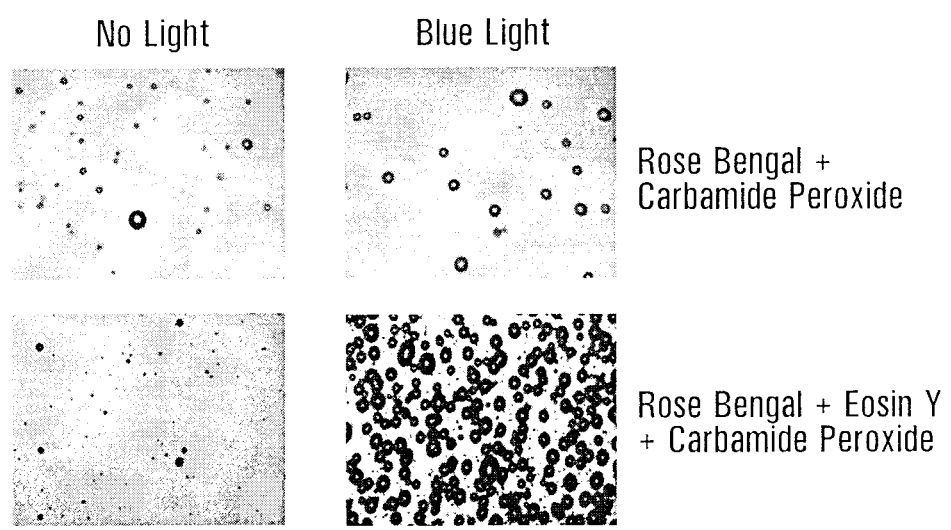
FIG. 12 illustrates photographs showing that Eosin and Rose Bengal act in a synergistic manner.

FIG. 12, left panel, shows a photograph of the composition when viewed under a light microscope (×250) before exposure to an activating light. Little foaming was seen in both compositions. Following illumination with blue light, right panel, a dramatic increase in foam was seen with the composition comprising a combination of Eosin Y and Rose Bengal, but not with the composition comprising Rose Bengal alone. This suggests that there is a transfer of energy from Eosin Y to Rose Bengal leading to the formation of oxygen species.

Example 13—Viscosity of Spreadable Compositions

Gels, based on carbopol polymers with differing concentrations, were evaluated for their suitability for use in embodiments of biophotonic compositions of the present disclosure. The viscosity, spreadability and ability to stay in place on tissue of the gels were evaluated. The gels comprised carbopol 940, glycerin, propylene glycol, water, as well as small amounts of a chelator, a pH adjuster, healing factors and preservatives. Ten gel compositions were tested having varying amounts of carbopol 940, all other ingredient concentrations remaining the same. Viscosity was evaluated using (1) Brookfield DV-II+Pro viscometer: spindle 7, 50 rpm, 1 minute; and (2) Brookfield HN viscometer: spindle CP51, 2 rpm. Ability to be easily spread was evaluated based on ease of forming a 2 mm thick layer on a surface and ability to conform to the surface topography. Ability to stay in place was evaluated by placing a 2 mm thick layer of each gel on a surface of a pork chop having an 8 mm diameter biopsy punch in order to simulate a wound. The steak was then positioned such that the surface having the gel thereon was at about 90° to a horizontal plane (i.e. the gel was substantially vertical) and was then left in place for 5 minutes at room temperature. The results are summarized in Table 6.

TABLE 6

Evaluation of viscosity, spreadability and ability to stay in place of gels having different carbopol concentrations.

| Gel | % by wt Carbopol | Viscosity (cP) (1) | Viscosity (cP) (2) | Ability to be spread | Ability to stay in place |
|---|---|---|---|---|---|
| 1 | 0.2 | 0 | 0 | Too liquid | Too liquid |
| 2 | 0.5 | 800 | 828 | Too liquid | Too liquid |
| 3 | 1.0 | 11920 | 11737 | Good | Good |
| 4 | 1.7 | 33840 | 38110 | Good | Good |
| 5 | 2.0 | 71520 | 74563 | Not easy to make gel conform to the wound topography | Good |
| 6 | 2.5 | 74080 | 74770 | Difficult to make gel conform to the wound topography | Good |
| 7 | 1.1 | 15840 | 15948 | Good | Good |
| 8 | 1.3 | 21280 | 22783 | Good | Good |
| 9 | 1.5 | 31360 | 33346 | Good | Good |
| 10 | 1.85 | 44320 | 49295 | Good | Good |

Gels which did not flow when positioned vertically were obtained with a carbopol wt % of more than 0.5% and higher. Gels with a carbopol wt % of more than 0.5% and less than 2 wt % could be spread as a 2 mm thick layer. These gels may be suitable gelling agents for biophotonic compositions of the present invention. Other concentrations of carbopol may also be used in conjunction with thickening agents or diluters in biophotonic compositions of the present disclosure. Also, other carbopol grades, polymers and other gelling agents may also have properties suitable for use as a gelling agent in the present compositions.

Example 14—Healing of Non-Healing Wounds

The non-healing wounds (stage H and III pressure ulcers) of sixteen patients were treated with an embodiment of the presently disclosed biophotonic composition and method. These chronic wounds were unresponsive to previous failed multiple treatments such as surgical debridement, dressings, hydrocolloids which had been performed in the last 3 months.

The spreadable biophotonic composition was a gel which included a fluorophore in a carbopol gel and an oxygen releasing compound (urea peroxide—although any other oxygen releasing compound could also be used), the gel having a viscosity of about 10,000 cP to 50,000 cP, and demonstrating less than 15% leaching when tested for up to 30 minutes according to Example 5. A thin layer of the biophotonic composition was topically applied to the wound and illuminated for 5 minutes with a blue LED light having a power density of about 50 to 150 mW/cm$^2$ at a distance of 5 cm from the light. The biophotonic composition was removed. Each wound was treated twice weekly. Efficacy was determined by total wound closure. Wound closure was defined as skin re-epithelialization without drainage or dressing requirements confirmed at two consecutive visits two weeks apart. Secondary endpoints assessed safety and tolerance of the treatment, change in pressure ulcer stage, occurrence of infections, and wound breakdown.

All wounds responded to the biophotonic method and composition by progressing to granulation, despite not responding to other wound healing treatments in the preceding months. As of the end of the case study period (about 8 months), 8 wounds were completely closed (50%) without surgical intervention with a mean time for total closure of 11.3 weeks and a median time of 9 weeks. This was higher than expected. The mean time to reach 50% healing was 2 weeks (median time was 2.7 weeks). At 12 weeks from starting the treatment, 5 wounds were already totally closed. All of the closed wounds remained closed after a 4-week follow-up period. Two additional patients progressed to wound closure through surgery (skin graft). One patient was progressing to closure but needed to be transferred to a different medical center. If the patient had not been transferred, this wound would also likely have closed, pushing the number of closed wounds to 9. Two other patients were lost to follow-up. Three patients had not closed by 8 months but the wound was progressing to healing slowly. In one patient, the wound was progressing well but recurrent fecal incontinence led to a severe infection of the wound which resulted in suspension of the biophotonic treatment for antibiotic treatment.

Nine of the patients treated in the case studies are presented below. All were paraplegics in whom healing tends to be delayed.

Figures 13A, 13B:
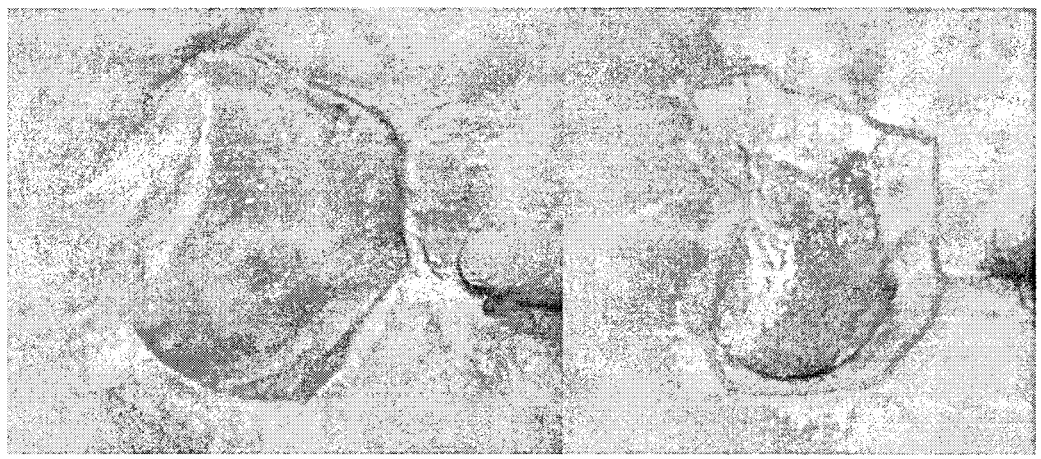
FIGS. 13A to 13C illustrate photographs showing a grade II sacral wound at (13A) time zero, (13B) time 3.5 months and (13C) time 6 months, following treatment with a biophotonic composition according to certain aspects of the present disclosure and a method according to certain aspects of the present disclosure.
Figure 13C:

Case 1:

In FIGS. 13A to 13C is shown a Grade II non-healing sacrum wound. The patient was a quadriplegic male who developed a complex wound during hospitalization. Prior to undergoing the biophotonic treatment, the patient underwent multiple surgical procedure and wound healing treatments including debridement, local flaps, split thickness skin grafting and serial attempts at hydrocolloid, hydrogels, antiseptics and antibiotic treatments. The patient required urgent coverage/closure of the wound to avoid a progression of the wound size and possible osteomyelitis but was unable to undergo a free-tissue transfer procedure. The wound was 4 months old when it received the biophotonic treatment method which consisted of application of the biophotonic composition followed by illumination and then removal of the composition, twice weekly. The wound was treated for approximately 6 months and progressed in a stable fashion from a severe chronic non-surgical wound to a surgically optimized wound. The wound decreased dramatically in surface area and depth. Treatment had to be stopped before closure as the patient was moving away, but the wound was expected to close. FIG. 13A clearly shows a recalcitrant chronic wound with minimal granulation tissue. After approximately 3.5 months of applying the biophotonic composition and method, the overall appearance was improved (FIG. 13B). There was healthy granulation tissue combined with new skin ingrowth. At around 6 months (FIG. 13C) the wound continued to improve, decreasing in size while maintaining a continuously healthy center.

Figure 14A:
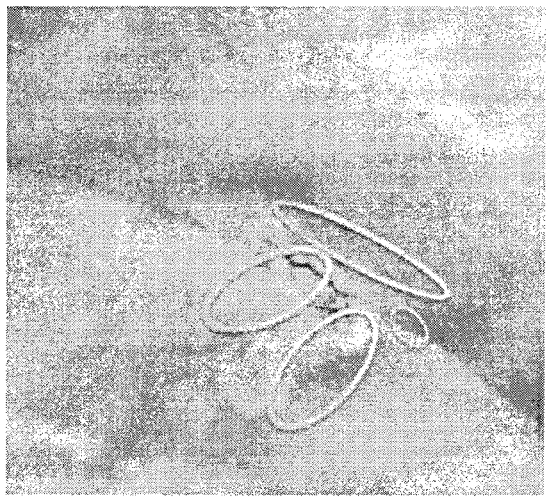
FIGS. 14A and 14B illustrate photographs of a grade III sacral wound at (14A) time zero, and (14B) 7 months following treatment with a biophotonic composition and a method according to certain aspects of the present disclosure.
Figure 14B:

Case 2:

A 62 year old woman with a herniated disc, spastic paresis and reduced mobility developed a grade III sacral pressure sore with significant subcutaneous tunneling. Prior to the biophotonic composition and treatment, the pressure sore was treated by packing the wound with wet-dry dressings, hydrocolloids and hydrogels. The wound failed to progress and developed into a 10 week old, chronic unresponsive subcutaneous wound. The wound was treated twice weekly for about 7 months with the biophotonic composition and method. There were no adverse events during the treatment, and the wound closed completely at around 7 months from starting the treatment. FIG. 14A shows the subcutaneous grade III wound at time zero. Tunneling can be observed (indicated by the oval shapes). After around 7 months of treatment, the wound closed with no tunneling (FIG. 14B).

Figure 15A:
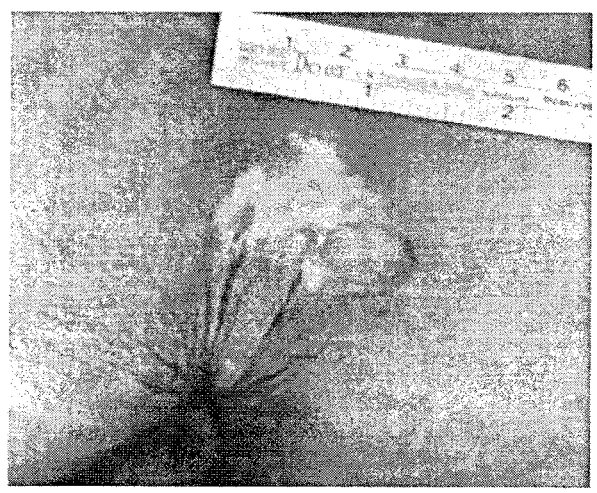
FIGS. 15A and 15B illustrate photographs showing a grade II sacral wound at (15A) time zero, and (15B) time 4 months following treatment with a biophotonic composition and a method according to certain aspects of the present disclosure.
Figure 15B:
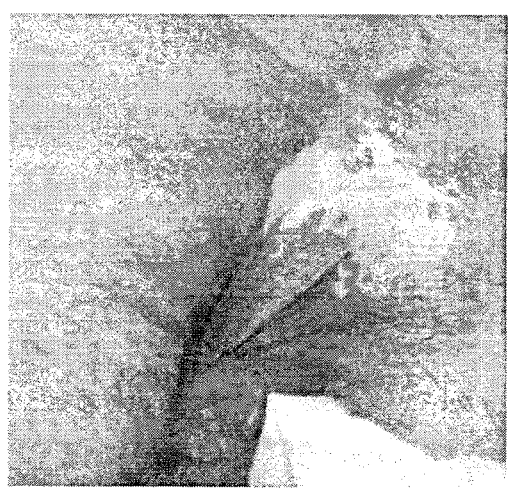

Case 3:

A 51 year old female paraplegic with two stage II sacral pressure sores. Prior to the biophotonic composition and method, the wounds were treated unsuccessfully with regional flap and multiple wound dressings (hydrocolloids, transparent adhesive dressings, antibiotic and zinc dressings). The wound was treated twice weekly for about 4 months with the biophotonic composition and method. There were no adverse events during the treatment, and the wound closed completely at around 4 months from starting the treatment. FIG. 15A shows the wound at time zero, where the wound appears to be stalled with multiple grade II ulcerations that failed to progress. The wound closed 4 months after treatment (FIG. 15B). The healed wound maintained a non-hypertrophic appearance with excellent elasticity and a normal texture compared to its non-healing state.

Figure 16A:
FIGS. 16A to 16F illustrate photographs showing a grade III sacral wound at (16A) time zero, (16B) time 2 weeks, (16C) time 3 weeks, (16D) time 4 weeks (when treatment was started), (16E) 3 months (2 months of treatment), and (16F) 5 months (3 months of treatment), wherein treatment was with a biophotonic composition and a method according to certain aspects of the present disclosure.
Figure 16B:
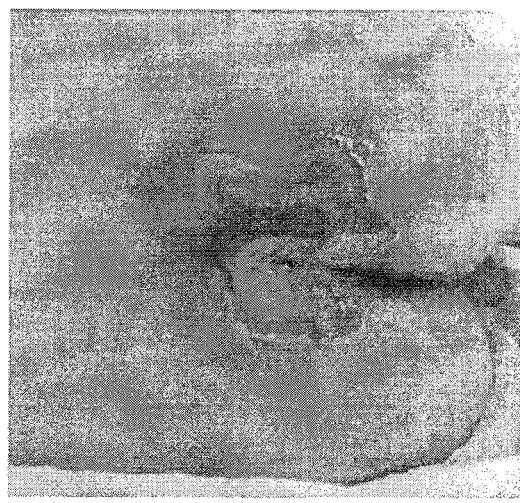
Figure 16C:
Figure 16D:
Figure 16E:
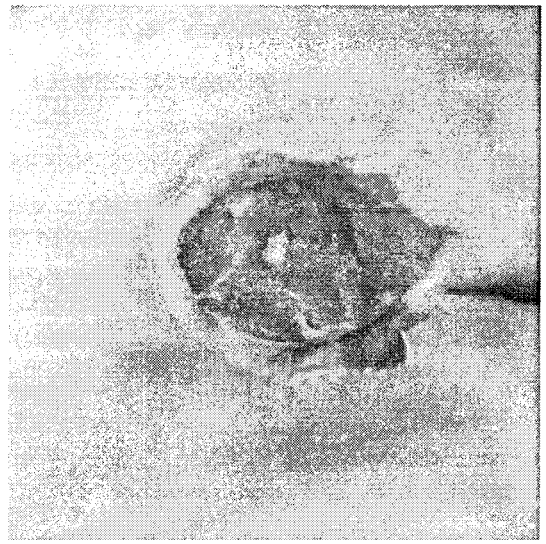
Figure 16F:
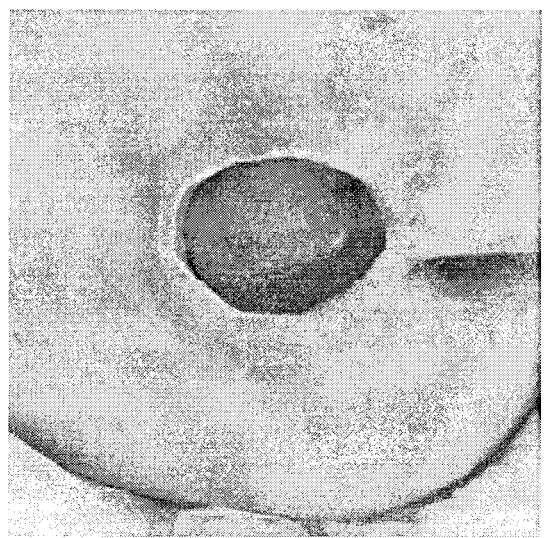

Case 4:

A 32 year old paraplegia patient developed a grade III pressure sore over several months. The wound progressed from a grade II to a grade III despite optimizing risk factors. The patient presented with a progressing sacral pressure sore and over the course of 2-3 weeks developed frank full thickness necrosis of the region (FIGS. 16A-16C). The biophotonic method treatment started 1 month after development of the pressure sore and the necrosis. The biophotonic method was applied twice weekly for 4 months. Following biophotonic treatment, the wound decreased in volume substantially and led to a clean well granulating surface. Treatment had to stop when the patient was transferred to another facility. At time zero (FIG. 16A), the wound was evident as a severe pressure sore with a necrotic center. The wound eventually declared itself, as the underlying necrosis came to the surface. The wound was observed for the first month, and by 3 weeks into this first month the wound worsened from a Grade II-III to a significant Grade III and presented necrotic regions (FIGS. 16C-16D). Two months after the biophotonic treatment method was started (FIG. 16E) (i.e. 3 months from the time zero observation of the wound (FIG. 16A)), the wound was observed to contract circumferentially while maintaining a continuously improving center of granulation. After 4 months of applying the biophotonic treatment method (FIG. 16F (i.e. 5 months from the time zero observation of the wound (FIG. 16A)), the wound presented a healthy granulation bed, with an increasing volume of granulation tissue in the center and periphery of the wound.

Figure 17A:
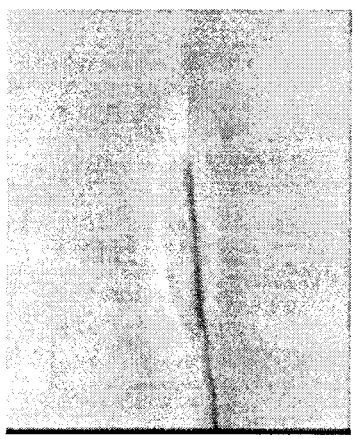
FIGS. 17A to 17C illustrates photographs showing a grade II sacral wound at (17A) time zero, (17B) time 1 month, and (17C) time 2.5 months following treatment with a biophotonic composition and a method according to certain aspects of the present disclosure.
Figure 17B:
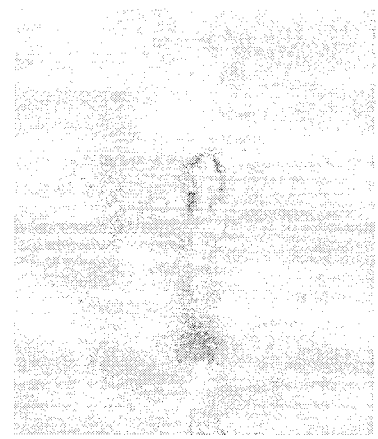
Figure 17C:
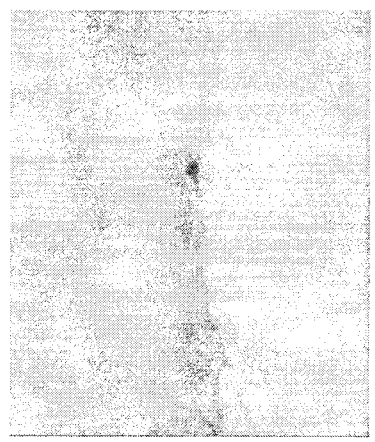

Case 5:

A 41 year old patient with a grade II sacral pressure sore. Prior to the biophotonic treatment, the patient had been treated with multiple established wound healing treatments over several months without improvement. The wound was treated twice weekly for about 2.5 months with the biophotonic treatment method. There were no adverse events during the treatment, and the wound closed completely at around 2.5 months from starting the biophotonic treatment. At time zero, the wound appeared as a non-healing recalcitrant chronic wound (FIG. 17A). The wound itself maintained a greyish hue over several weeks prior to the onset of treatment. At 1 month following treatment (FIG. 17B), the wound began to achieve an improved appearance with deposition of healthy granulation tissue with a segment of the wound closing. After about 2.5 months of applying the biophotonic method and composition (FIG. 17C), the wound closed in a stable manner and with a healthy appearance.

Figure 18A:
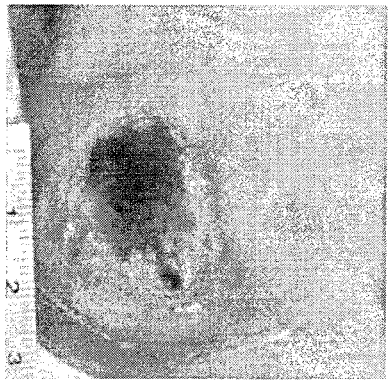
FIGS. 18A to 18C illustrate photographs showing a grade III heel ulcer at (18A) time zero, (18B) time 2.5 months, and (18C) time 4 months following treatment with a biophotonic composition and a method according to certain aspects of the present disclosure.
Figure 18B:
Figure 18C:

Case 6:

41-year female patient with a grade III heel ulcer, secondary to unrelieved pressure. Prior to applying the biophotonic composition and treatment method, the wound was treated with multiple established wound healing treatments including surgical debridement, wet to dry dressings, hydrogels and antibiotic ointments, without improvement. The wound was treated twice weekly for about 4 months with the biophotonic treatment method. There were no adverse events during the treatment, and the wound closed completely at around 4 months from starting the treatment. At time zero, the wound was a grade III heel ulcer with a slough of necrotic tissue typically observed in non-healing wounds (wound 'eschar') (FIG. 18A). After about 2.5 months of treatment, the surface area of the wound decreased in size while maintaining an improved central component and a circumferentially closing wound (FIG. 18B). The wound closed after about 4 months of applying the biophotonic composition and method (FIG. 18C).

Figure 19A:
FIGS. 19A to 19C illustrate photographs showing a grade III heel ulcer at (19A) time zero, (19B) 8 weeks, and (19C) 11 weeks following treatment with a biophotonic composition and a method according to certain aspects of the present disclosure.
Figure 19B:
Figure 19C:
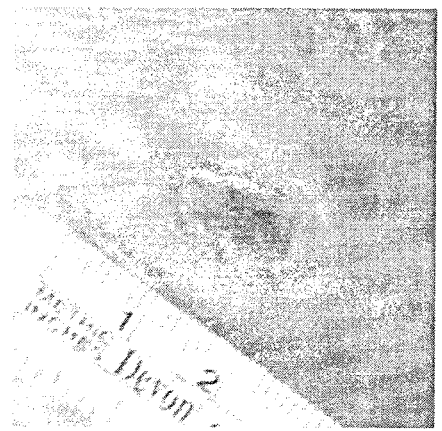

Case 7:

32 year old paraplegic patient with a grade III pressure sore in the inner left heal. Prior to applying the biophotonic method, the wound had been treated with enzymatic debridement, hydrocolloids and hydrogels. The wound was treated twice weekly for 11 weeks with the biophotonic composition and method. There were no adverse events during the treatment, and the wound closed completely at around 11 months from starting the treatment. At time zero, wound was a Grade III pressure sore measuring about 2 cm in width with a stagnating center (FIG. 19A). After about 8 weeks of treatment, the wound had decreased in size, with an improved central granulating component (FIG. 19B). After about 11 weeks, the wound continued improving with a maximal peripheral contracture (FIG. 19C).

Figure 20A:
FIGS. 20A and 20B illustrate photographs showing a grade III heel ulcer at (20A) time zero, and (20B) 10.5 weeks following treatment with a biophotonic composition and a method according to certain aspects of the present disclosure.
Figure 20B:

Case 8:

32 year old paraplegic with a grade III pressure sore on the outer left heal. Prior to applying the biophotonic treatment method, the wound had been treated with enzymatic debridement, hydrocolloids and hydrogels. The wound was treated twice weekly for about 10.5 months with the biophotonic composition and method. There were no adverse events during the treatment, and the wound closed completely at around 10.5 months from starting the biophotonic treatment. Before the biophotonic treatment, the wound was a grade III pressure sore appearing stalled over a significant period of time (FIG. 20A). The wound closed after about 10.5 months, progressing from an improved central granulating component and a consistent contracture of the circumferential wound margin (FIG. 20B).

Figure 21A:
FIGS. 21A to 21D illustrates photographs showing a grade III sacral wound at (21A) time zero, (21B) time 2.5 months, (21C) time 4 months and (21D) time 5 months following treatment with a biophotonic composition and a method according to certain aspects of the present disclosure.
Figure 21B:
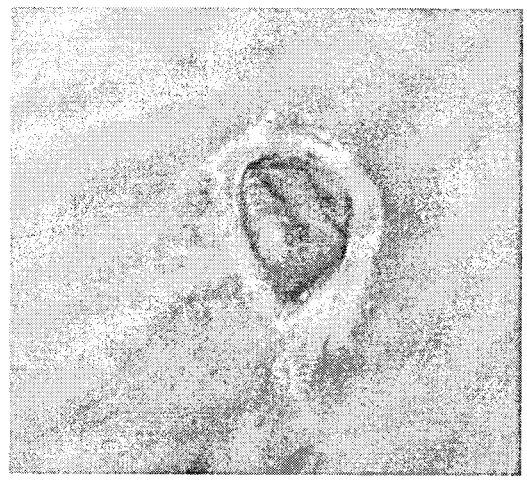
Figure 21C:
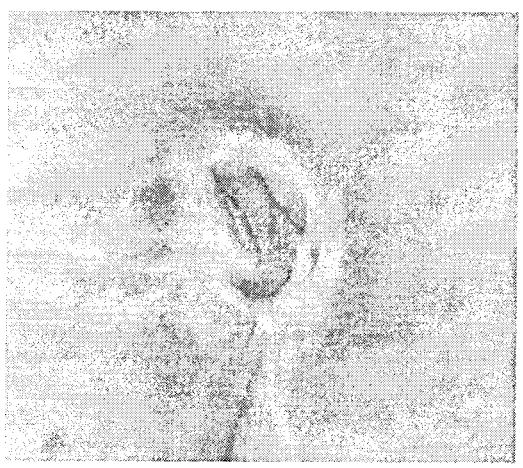
Figure 21D:

Case 9:

Tetraplegic patient who developed a grade III pressure sore that had been present for about 4 months. The patient had undergone treatment with multiple wound dressings unsuccessfully. The wound received the biophotonic composition and method treatment twice weekly for 5 months. Following wound closure, significant wound contracture was seen and decreased wound depth despite the patient having hypoalbuminemia (hypoalbuminemia is associated with impaired wound healing). The wound was eventually able to be closed with a small split thickness skin graft. Before treatment the wound was a grade III pressure wound, with a non-improving and poorly granulating center (FIG. 21A). As treatment progressed, the wound decreased in size significantly (FIGS. 21B-21D), despite all the patient co-morbid factors. Therefore, it could be seen from these case studies that repair was stimulated in otherwise non-responsive non-healing wounds using the present biophotonic composition and method. It also appeared that these wounds were healing in an accelerated manner i.e. wounds that might have taken years to close were closing in under a year. Furthermore, the wounds appeared to be healing 'from the bottom up'. By this it is meant that the wound base was granulating and regenerating faster than the edges of the wound were closing. In other words, the repair at the edges of the wound was delayed compared to that in the centre. This is advantageous in that the closed wound will not be hollow under the closed surface, which is commonly observed in some closed wounds. Therefore, the wound has a stronger integrity and is less likely to open or breakdown. This also reduces the amount or extent of scarring, which was also observed in these patients.

Figure 22A:
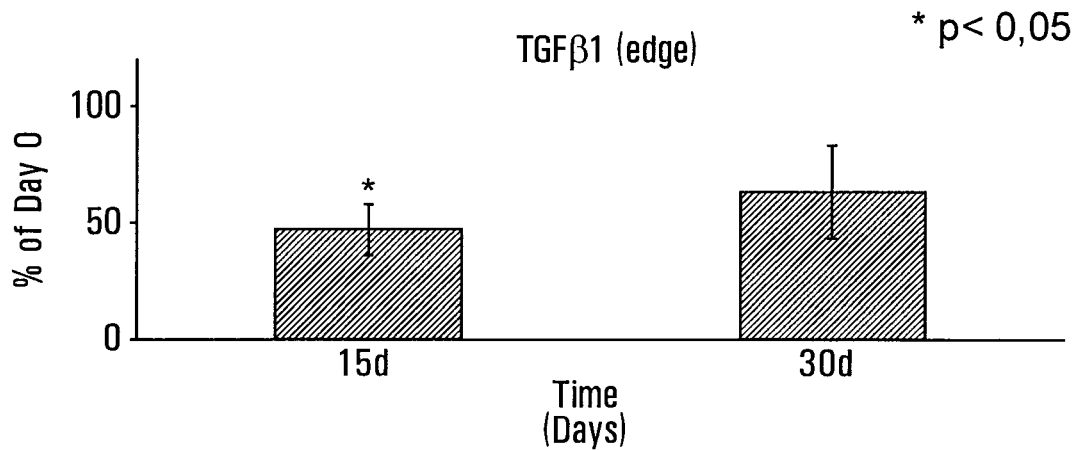
FIGS. 22A and 22B illustrate graphs showing the expression of growth factor TGFβ1 at the edge of the wound (22A) and at the center of the wound (22B) at day 15 and at day 30 following treatment with a biophotonic composition and a method according to certain aspects of the present disclosure.
Figure 22B:
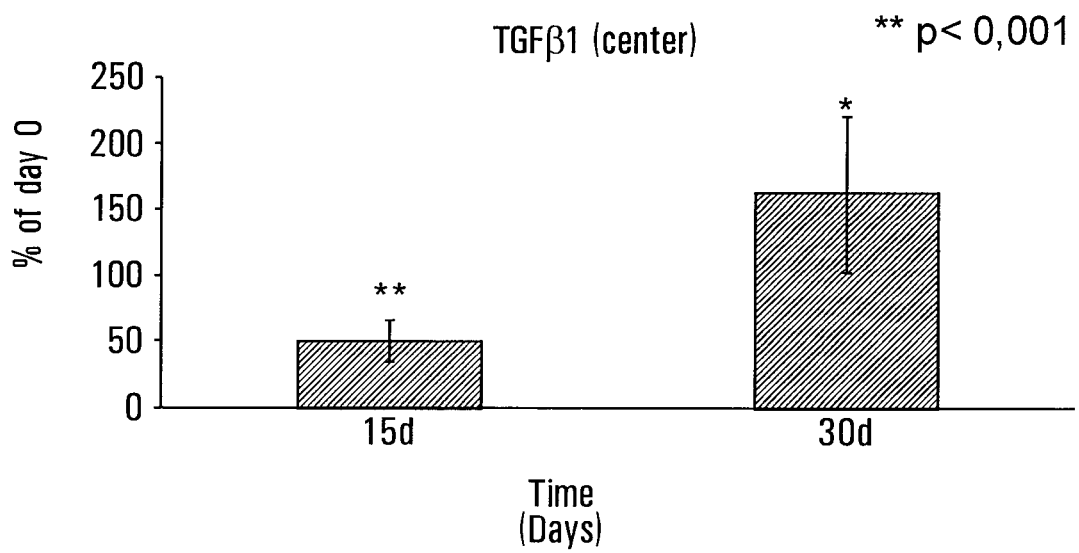
Figure 23A:
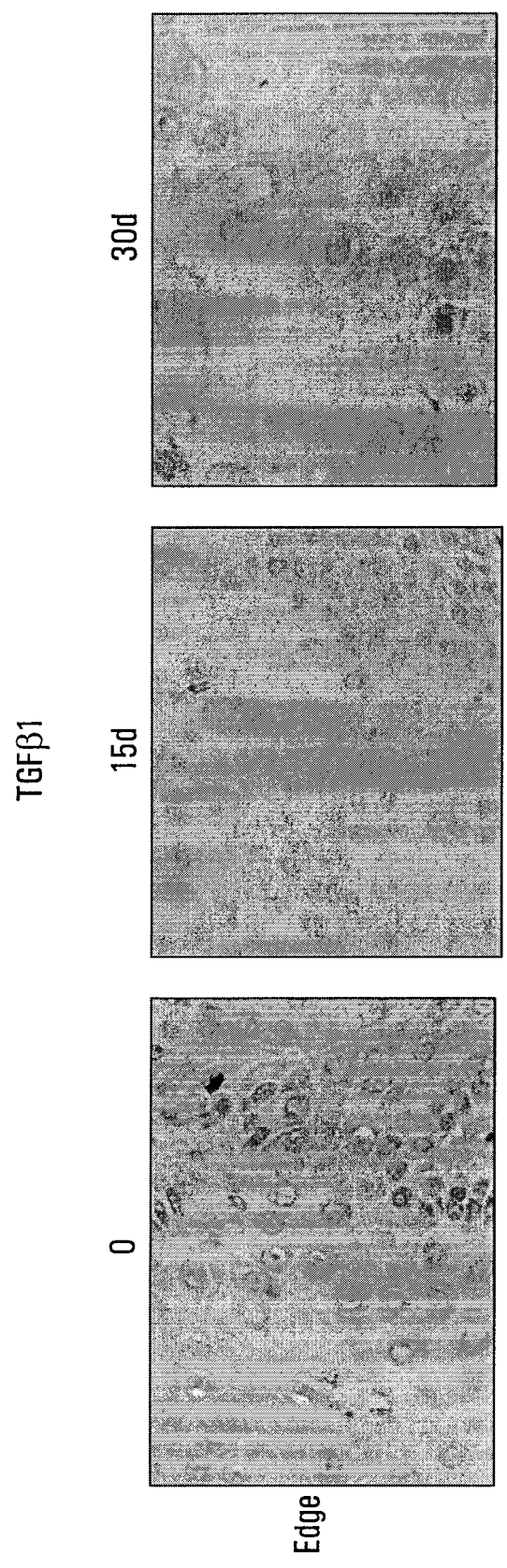
FIGS. 23A and 23B illustrate immunostaining showing the expression of growth factor TGFβ1 in a grade 2-3 wound at time zero, time 15 days, and time 30 days at the edge of the wound (23A) and at the center of the wound (23B) following treatment with a biophotonic composition and a method according to certain aspects of the present disclosure.
Figure 23B:
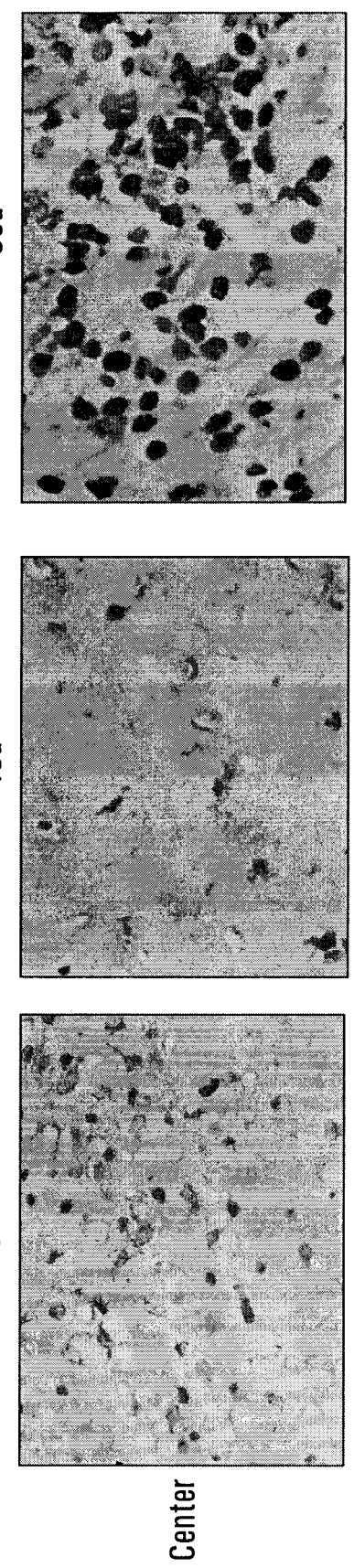
Figure 24A:
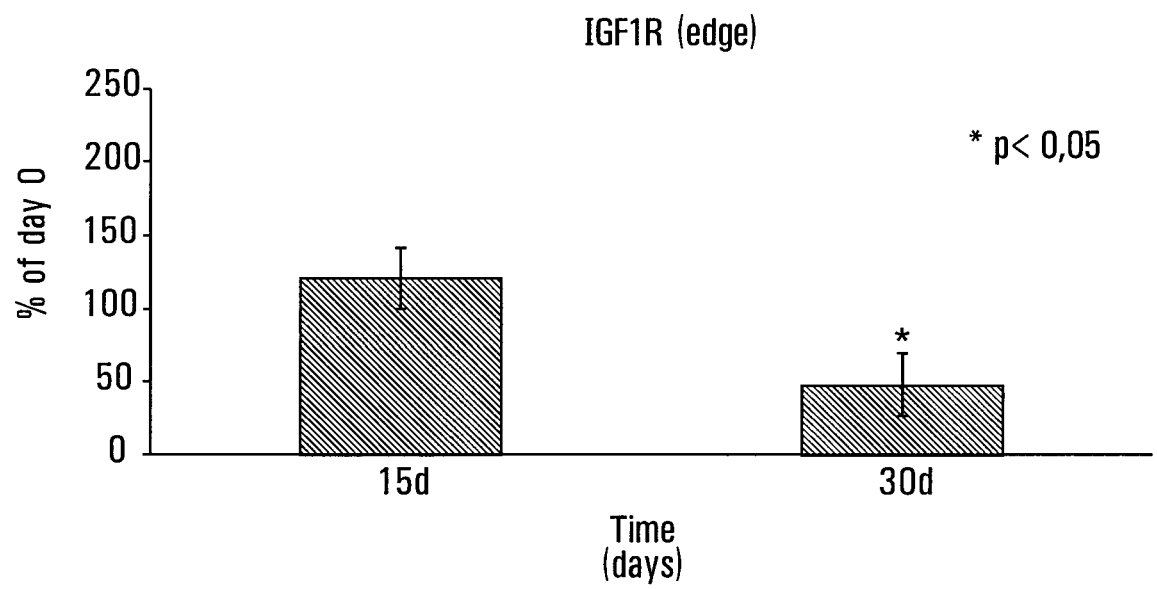
FIGS. 24A and 24B illustrate graphs showing the expression of growth factor IGF1R at the edge of the wound (24A) and at the center of the wound (24B) at day 15 and at day 30 following treatment with a biophotonic composition and a method according to certain aspects of the present disclosure.
Figure 24B:
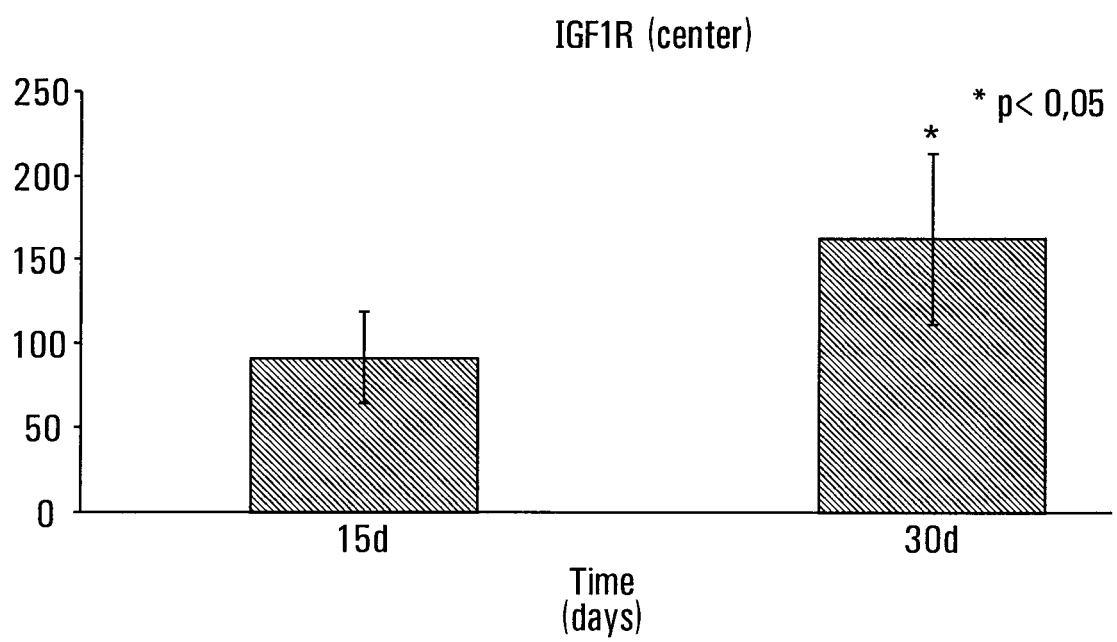
Figure 25A:
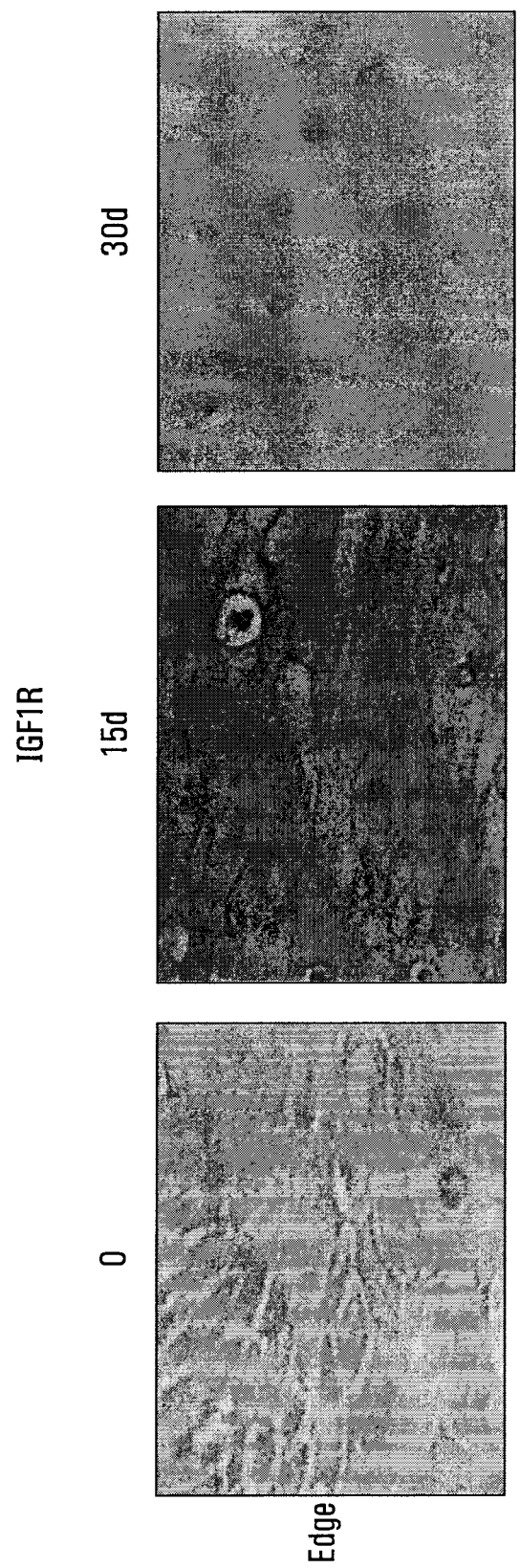
FIGS. 25A and 25B illustrate immunostaining showing the expression of growth factor IGF1R in a grade 2-3 wound at time zero, time 15 days, and time 30 days at the edge of the wound (25A) and at the center of the wound (25B) following treatment with a biophotonic composition and a method according to certain aspects of the present disclosure.
Figure 25B:
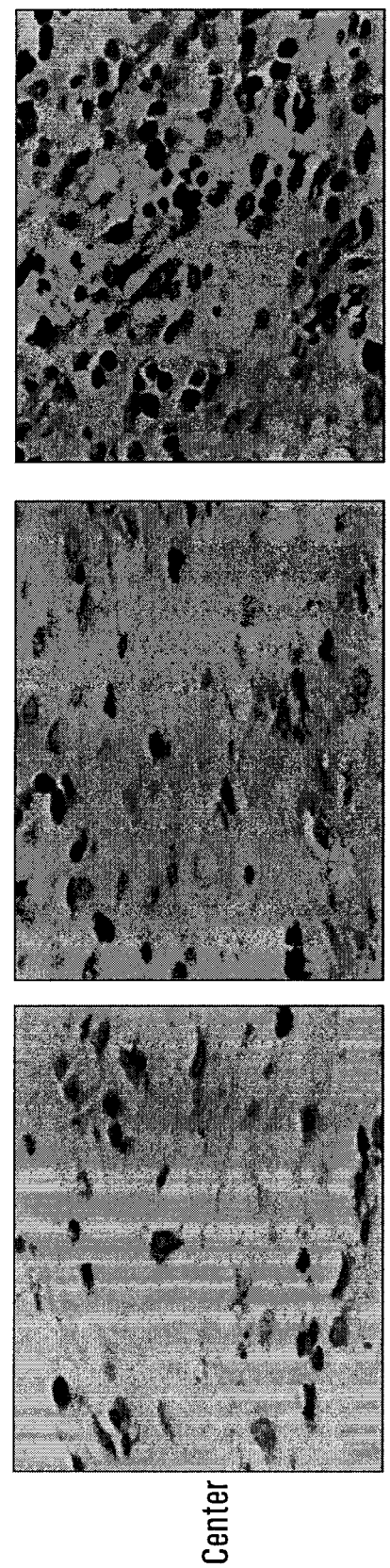
Figure 26A:
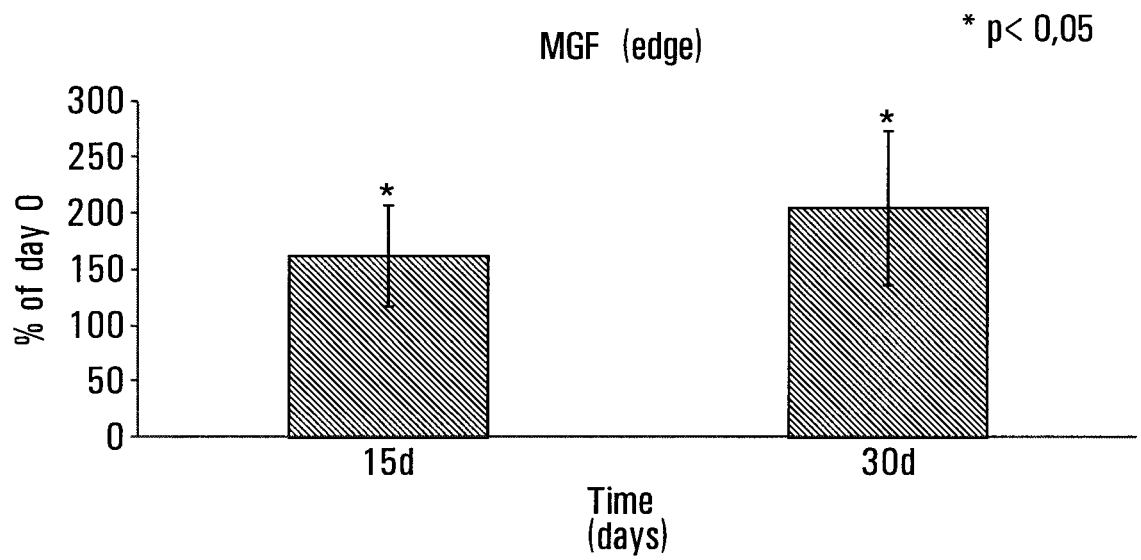
FIGS. 26A and 26B illustrate graphs showing the expression of growth factor MGF at the edge of the wound (26A) and at the center of the wound (26B) at day 15 and at day 30 following treatment with a biophotonic composition and a method according to certain aspects of the present disclosure.
Figure 26B:
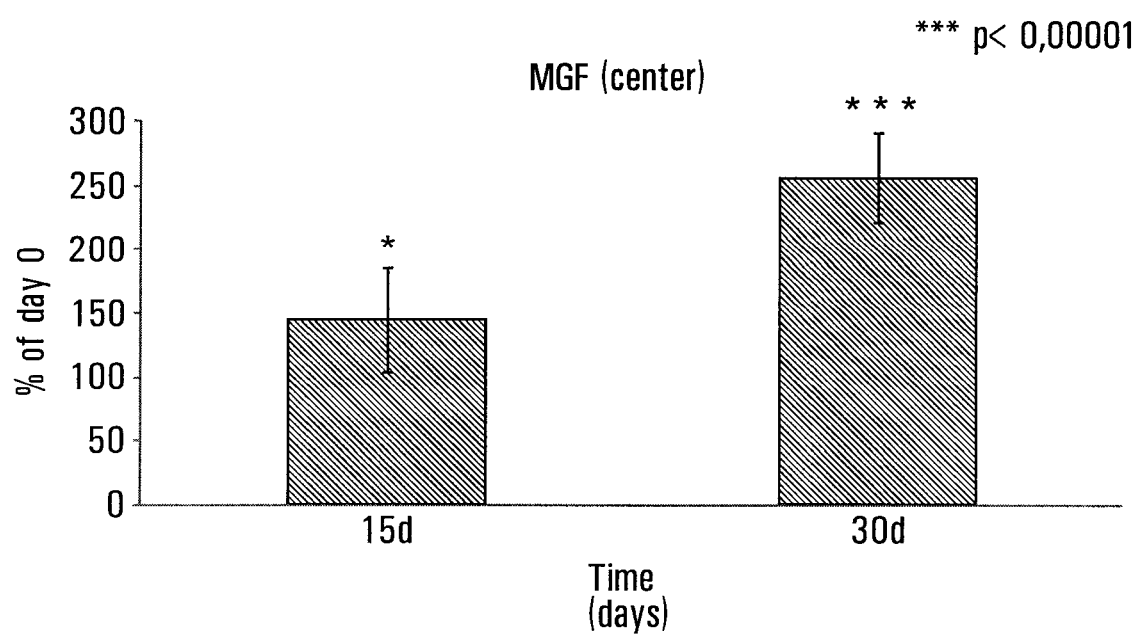
Figure 27A:
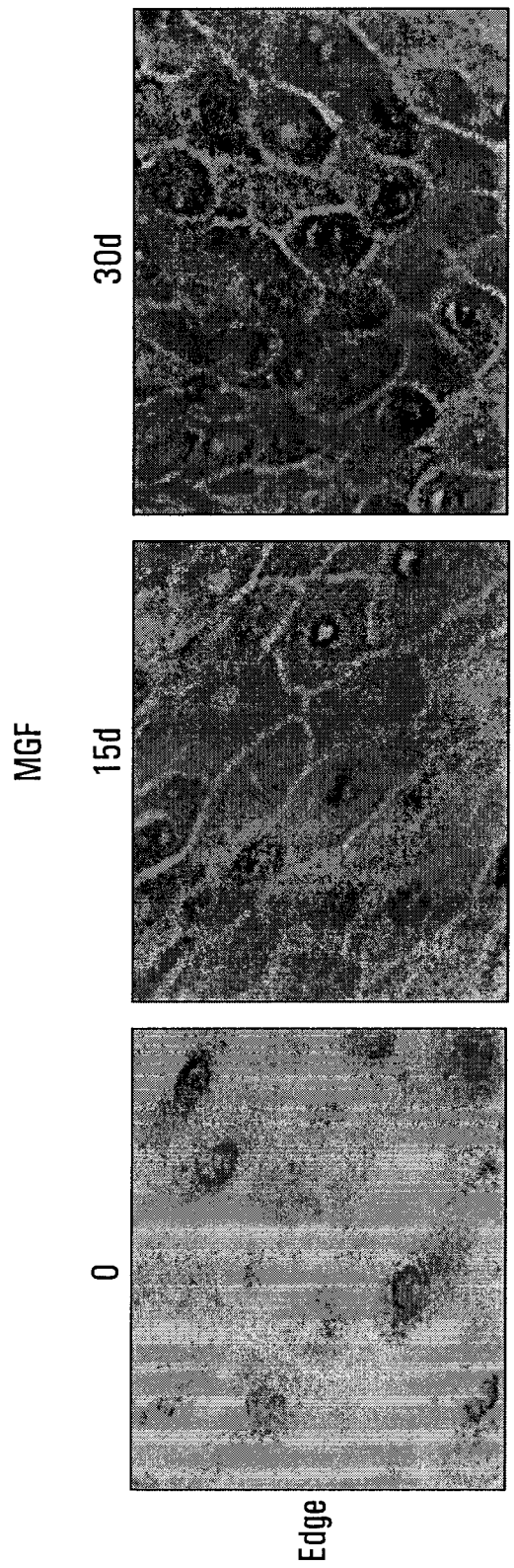
FIGS. 27A and 27B illustrate immunostaining showing the expression of MGF in a grade 2-3 wound at time zero, time 15 days, and time 30 days at the edge of the wound (27A) and at the center of the wound (27B) following treatment with a biophotonic composition and a method according to certain aspects of the present disclosure.
Figure 27B:
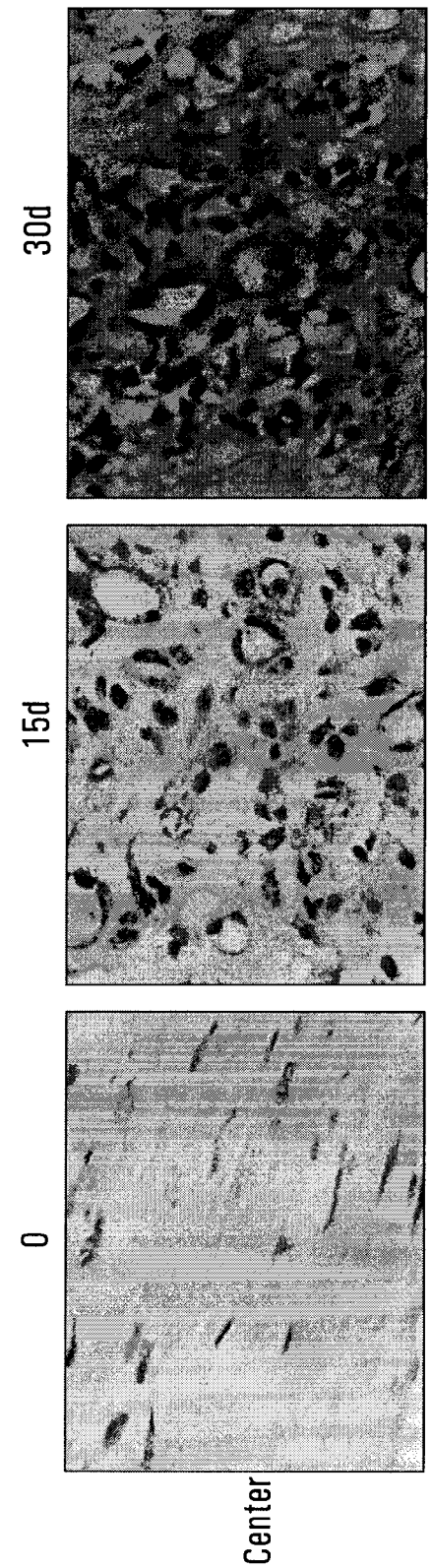
Figure 28A:
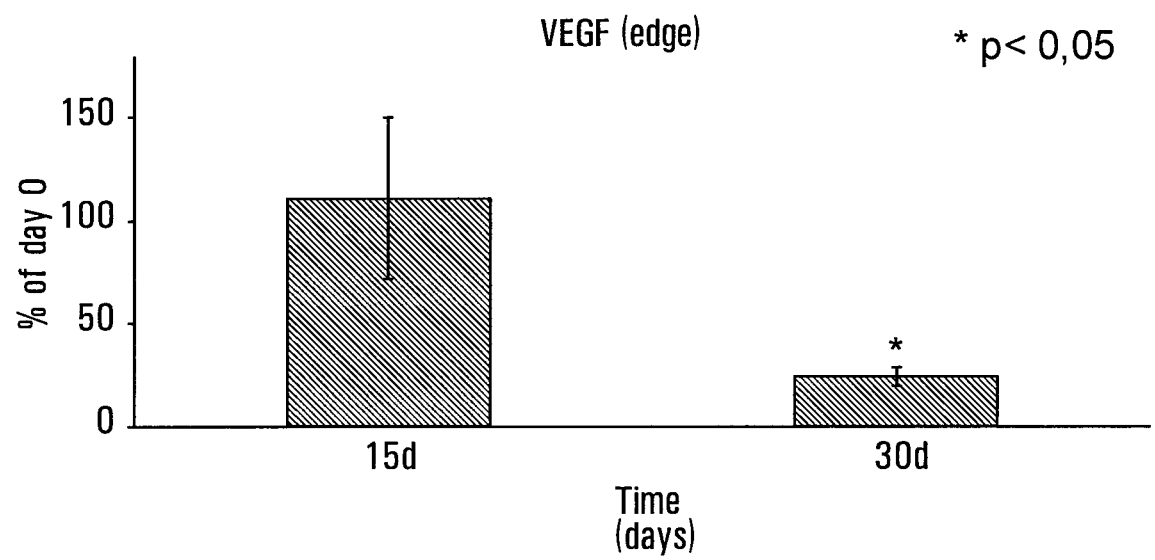
FIGS. 28A and 28B illustrate graphs showing the expression of VEGF at the edge of the wound (28A) and at the center of the wound (28B) at day 15 and at day 30 following treatment with a biophotonic composition and a method according to certain aspects of the present disclosure.
Figure 28B:
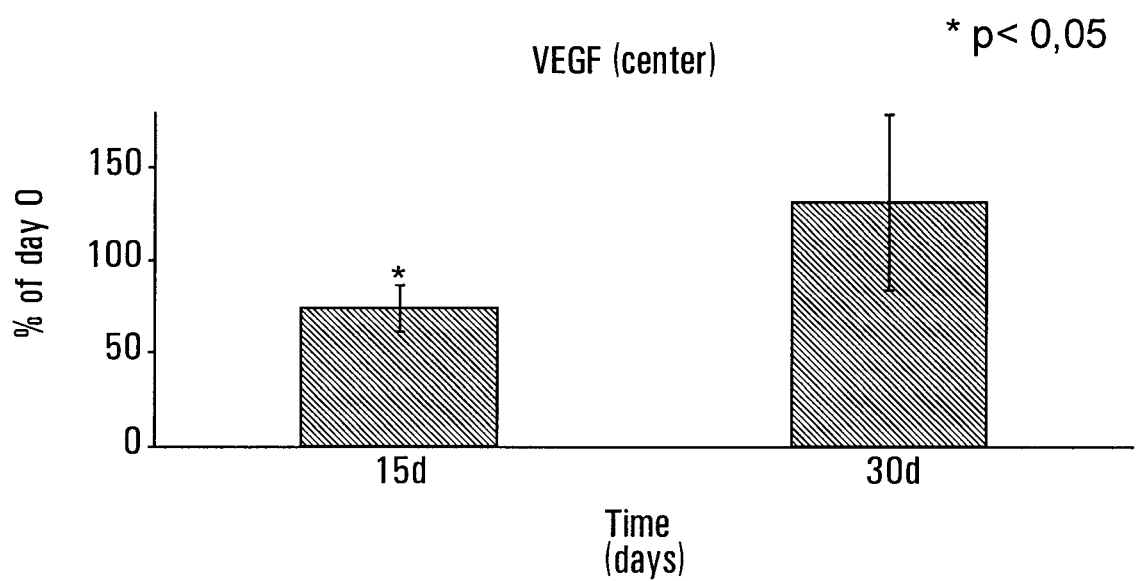

Example 15—Healing at the Periphery of the Wound is Delayed Compared to Healing at the Center of the Wound Punch biopsies were performed week 1 of the treatment with the biophotonic composition as defined herein, week 2 of treatment, week 4 of treatment, and week 20 of treatment prior to any study procedures with a round disposable punch biopsy ranging in diameter of 3 mm. Two samples were taken: one from the periphery of the wound and one from the center of the wound. Tissues were fixed with 70% ethanol (not in formalin) prior to paraffin embedding. Wound healing was assessed at the periphery of the wound and at the center of the wound using antibodies specific for TGFβ1 (FIGS. 22A and 23A, periphery of wound; and FIGS. 22B and 23B, center of wound); antibodies specific for IGF1R (FIGS. 24A and 25A, periphery of wound; and FIGS. 24B and 25B, center of wound), antibodies specific for MGF (FIGS. 26A and 27A, periphery of wound; and FIGS. 26B and 27B, center of wound); and antibodies specific for VEGF (FIGS. 28A and 29A, periphery of wound; and FIGS. 28B and 29B, center of wound). The data presented in FIGS. 22 to 29 thus show an increased presence of TGFβ1, IGF1R, MGF and VEGF at the center of the wound compared to along the periphery of the wound after 30 days of treatment with the biophotonic compositions as defined herein indicating a delay in healing at the periphery of the wound compared to at the center of the wound.

It should be appreciated that the invention is not limited to the particular embodiments described and illustrated herein but includes all modifications and variations falling within the scope of the invention as defined in the appended claims.

All documents referred to herein are hereby incorporated by reference into the present application.

The invention claimed is:

1. A method for stimulating repair of a Grade II chronic wound, or of a Grade III chronic wound, or both, to generate a closed wound without a hollow under a surface of the closed wound, comprising:
    applying topically a biophotonic composition to the Grade II chronic wound, or to the Grade III chronic wound, or to both; wherein the biophotonic composition comprises:
        at least a first chromophore; and
        a gelling agent present in an amount sufficient to gel the composition and render the biophotonic composition substantially resistant to leaching such that less than 15% by weight of the total chromophore amount leaches out of the biophotonic composition in use, and such that the biophotonic composition has a viscosity of between about 10,000 cP and about 50,000 cP; and
    illuminating the applied biophotonic composition with a light source emitting a light having a wavelength that overlaps with an absorption spectrum of the first chromophore and a power density of between about 50-150 mW/cm$^2$ at a distance of about 5 cm from the light source.

2. The method of claim 1, wherein the gelling agent is one or more of a cross-linked polymer, a hydrophilic material, a hygroscopic material or a hydrated polymer.

3. The method of claim 1, for further stimulating repair at the edge of the Grade II chronic wound, or of the Grade III chronic wound, or both.

4. The method of claim 3, wherein the stimulated repair is delayed at the edge compared to the wound base of the Grade II chronic wound, or of the Grade III chronic wound, or both.

5. The method of claim 4, wherein the stimulated repair is increased at the wound base compared to the edge of the Grade II chronic wound, or of the Grade III chronic wound, or both.

6. The method of claim 3, wherein stimulating repair comprises inducing expression of growth factors or cytokines or both.

7. The method of claim 6, wherein the induced growth factor expression is different at the wound base than at edge of the Grade II chronic wound, or of the Grade III chronic wound, or both.

8. The method of claim 3, wherein stimulating repair comprises attracting repair cell progenitors and/or repair cells to the centre of the Grade II chronic wound, or of the Grade III chronic wound, or both.

9. The method of claim 8, wherein repair cells comprise fibroblasts, keratinocytes or endothelial cells.

10. The method of claim 1, wherein the Grade II chronic wound, or the Grade III chronic wound, or both, are activated Grade II chronic wound, or activated Grade III chronic wound, or both.

11. The method of claim 1, wherein the healing of the Grade II chronic wound, or of the Grade III chronic wound, or of both comprises increasing collagen expression.

12. The method of claim 11, wherein the collagen is collagen I, collagen III and/or procollagen.

13. The method of claim 1, wherein the healing of the Grade II chronic wound, or of the Grade III chronic wound, or of both comprises inducing granulation in the absence of surgical trauma.

14. The method of claim 1, wherein the healing of the Grade II chronic wound, or of the Grade III chronic wound, or of both comprises at least one of inducing angiogenesis, epithelialization and remodelling.

15. The method of claim 1, wherein the light is visible non-coherent light.

16. The method of claim 1, wherein the applying and illuminating steps are performed at least once, twice or three times a week, for a period of 1 week to 24 weeks.

17. A method for stimulating collagen formation at a Grade II chronic wound, a Grade III chronic wound, or at both to generate a closed wound without a hollow under a surface of the closed wound comprising:
applying topically a biophotonic composition to the Grade II chronic wound, the Grade III chronic wound, or to both; wherein the biophotonic composition comprises:
at least a first chromophore; and
a gelling agent present in an amount sufficient to gel the composition and render the biophotonic composition substantially resistant to leaching such that less than 15% by weight of the total chromophore amount leaches out of the biophotonic composition in use, and such that the biophotonic composition has a viscosity of between about 10,000 cP and about 50,000 cP; and
illuminating the applied biophotonic composition with a light source emitting a light having a wavelength that overlaps with an absorption spectrum of the first chromophore and a power density of between about 50-150 mW/cm² at a distance of about 5 cm from the light source.

18. The method of claim 17, further comprising removing the biophotonic composition after illumination.

19. The method of claim 17, wherein the biophotonic composition is illuminated for 1 minute to 30 minutes.

20. A method for stimulating repair of a Grade II chronic wound, a Grade III chronic wound, or both, to generate a closed wound without a hollow under a surface of the closed wound, comprising:
topically applying to the Grade II chronic wound, the Grade III chronic wound, or to both a biophotonic composition followed by illumination of the biophotonic composition applied at the wound base with an actinic light source emitting a light having a power density of between about 50-150 mW/cm² at a distance of about 5 cm from the light source, wherein the biophotonic composition comprises:
at least a first chromophore; and
a gelling agent present in an amount sufficient to gel the composition and render the biophotonic composition substantially resistant to leaching such that less than 15% by weight of the total chromophore amount leaches out of the biophotonic composition in use, and such that the biophotonic composition has a viscosity of between about 10,000 cP and about 50,000 cP; and
wherein the method comprises the following schedule:
(a) a period of from 1 day to 24 weeks during which said biophotonic composition is topically applied to the Grade II chronic wound, the Grade III chronic wound, or to both, followed by
(b) a rest period of from 3 days to 30 days; and
(c) repeating at least (a) until wound closure.

21. The method of claim 20, wherein the period of (a) continues until a slow-down of the wound healing response is observed.

* * * * *